United States Patent
Bierman et al.

(10) Patent No.: US 9,884,169 B2
(45) Date of Patent: Feb. 6, 2018

(54) ACCESS DEVICE WITH VALVE

(75) Inventors: Steven F. Bierman, Del Mar, CA (US); Richard A. Pluth, San Diego, CA (US)

(73) Assignee: Access Scientific, LLC, San Diego, CA (US)

(*) Notice: Subject to any disclaimer, the term of this patent is extended or adjusted under 35 U.S.C. 154(b) by 79 days.

(21) Appl. No.: 14/238,832

(22) PCT Filed: Aug. 17, 2012

(86) PCT No.: PCT/US2012/051495
§ 371 (c)(1),
(2), (4) Date: Feb. 13, 2014

(87) PCT Pub. No.: WO2013/026045
PCT Pub. Date: Feb. 21, 2013

(65) Prior Publication Data
US 2014/0207069 A1    Jul. 24, 2014

Related U.S. Application Data

(60) Provisional application No. 61/524,645, filed on Aug. 17, 2011.

(51) Int. Cl.
*A61M 25/06*    (2006.01)
*A61M 39/22*    (2006.01)
(Continued)

(52) U.S. Cl.
CPC ........ *A61M 25/06* (2013.01); *A61M 25/0668* (2013.01); *A61M 39/22* (2013.01);
(Continued)

(58) Field of Classification Search
CPC .. A61M 25/06; A61M 39/22; A61M 25/0097; A61M 25/0693; A61M 29/00; A61M 2039/244; A61M 2025/0098
(Continued)

(56) References Cited

U.S. PATENT DOCUMENTS 3,565,074 A    2/1971    Foti et al.
4,068,659 A    1/1978    Moorehead
(Continued)

FOREIGN PATENT DOCUMENTS

EP    0139091    7/1984
EP    0502714    11/1995
(Continued)

OTHER PUBLICATIONS

Arrow Trauma Products No. TRM-C 12/00 11M, Arrow International, dated 2000.
(Continued)

*Primary Examiner* — Edelmira Bosques
(74) *Attorney, Agent, or Firm* — Knobbe Martens Olson & Bear, LLPx

(57) ABSTRACT

A splittable sheath includes a splittable sheath body, a splittable sheath hub, and a valve element. The sheath body comprises a generally flexible tubular structure, a proximal end, and a distal end. The sheath body defines a longitudinal axis and is splittable into two halves along a pre-determined line generally parallel to the longitudinal axis. The sheath hub extends from the proximal end of the sheath body and defines a longitudinal axis generally aligned with the longitudinal axis of the sheath body. The sheath body and sheath hub form an inner cavity along their respective longitudinal axes. The valve element includes a resilient plate and a sealing element. The resilient plate includes a distal portion extending radially inwardly from a side of the inner cavity.

28 Claims, 41 Drawing Sheets

(51) Int. Cl.
  *A61M 39/24* (2006.01)
  *A61M 25/00* (2006.01)
  *A61M 29/00* (2006.01)

(52) U.S. Cl.
  CPC ..... *A61M 25/0097* (2013.01); *A61M 25/0693* (2013.01); *A61M 29/00* (2013.01); *A61M 2025/0098* (2013.01); *A61M 2039/244* (2013.01)

(58) Field of Classification Search
  USPC .................................................. 604/167.03
  See application file for complete search history.

(56) References Cited

U.S. PATENT DOCUMENTS

| | | | |
|---|---|---|---|
| 4,205,675 A | 6/1980 | Vaillancourt | |
| 4,230,123 A | 10/1980 | Hawkins, Jr. | |
| 4,417,886 A | 11/1983 | Frankhouser et al. | |
| 4,525,157 A | 6/1985 | Vaillancourt | |
| 4,581,019 A | 4/1986 | Curelaru et al. | |
| 4,610,665 A | 9/1986 | Matsumoto et al. | |
| 4,629,450 A | 12/1986 | Susuki et al. | |
| 4,655,750 A | 4/1987 | Vaillancourt | |
| 4,661,300 A | 4/1987 | Daugherty | |
| 4,772,264 A | 9/1988 | Cragg | |
| 4,791,937 A | 12/1988 | Wang | |
| 4,850,975 A | 7/1989 | Furukawa | |
| 4,861,341 A | 8/1989 | Woodburn | |
| 4,869,259 A | 9/1989 | Elkins | |
| 4,894,052 A | 1/1990 | Crawford | |
| 4,961,729 A | 10/1990 | Vaillancourt | |
| 4,963,306 A | 10/1990 | Weldon | |
| 4,978,334 A | 12/1990 | Toye et al. | |
| 5,059,186 A | 10/1991 | Yamamoto et al. | |
| 5,066,284 A | 11/1991 | Mersch et al. | |
| 5,105,807 A | 4/1992 | Kahn et al. | |
| 5,108,374 A | 4/1992 | Lemieux | |
| 5,167,637 A | 12/1992 | Okada et al. | |
| 5,171,218 A | 12/1992 | Fonger et al. | |
| 5,242,410 A | 9/1993 | Melker | |
| 5,246,426 A | 9/1993 | Lewis et al. | |
| 5,250,038 A | 10/1993 | Melker et al. | |
| 5,295,969 A | 3/1994 | Fischell | |
| 5,295,970 A | 3/1994 | Clinton et al. | |
| 5,306,253 A | 4/1994 | Brimhall | |
| 5,312,355 A | 5/1994 | Lee | |
| 5,334,157 A | 8/1994 | Klein et al. | |
| 5,356,394 A | 10/1994 | Farley et al. | |
| 5,366,441 A | 11/1994 | Crawford | |
| 5,380,290 A | 1/1995 | Makower et al. | |
| 5,397,311 A | 3/1995 | Walker et al. | |
| 5,419,766 A | 5/1995 | Chang et al. | |
| 5,542,932 A | 8/1996 | Daugherty | |
| 5,578,083 A | 11/1996 | Laguette et al. | |
| 5,589,120 A | 12/1996 | Khan et al. | |
| 5,676,689 A | 10/1997 | Kensery et al. | |
| 5,688,249 A | 11/1997 | Chang et al. | |
| 5,704,914 A | 1/1998 | Stocking et al. | |
| 5,755,693 A | 5/1998 | Walker et al. | |
| 5,795,339 A | 8/1998 | Erskine | |
| 5,810,780 A | 9/1998 | Brimhall et al. | |
| 5,820,596 A | 10/1998 | Rosen et al. | |
| 5,820,606 A | 10/1998 | Davis | |
| 5,827,202 A | 10/1998 | Miraki et al. | |
| 5,830,190 A | 11/1998 | Howell | |
| 5,833,662 A | 11/1998 | Stevens | |
| 5,858,002 A | 1/1999 | Jesch | |
| 5,858,007 A | 1/1999 | Fagan et al. | |
| 5,873,854 A | 2/1999 | Wolvek | |
| 5,885,253 A | 3/1999 | Liu | |
| 5,910,132 A | 6/1999 | Schultz | |
| 5,935,110 A | 8/1999 | Brimhall | |
| 5,951,518 A | 9/1999 | Licata et al. | |
| 6,046,143 A | 4/2000 | Khan et al. | |
| 6,066,117 A * | 5/2000 | Fox | A61B 17/3462 137/847 |
| 6,074,377 A | 6/2000 | Sanfilippo | |
| 6,077,249 A * | 6/2000 | Dittrich | A61B 17/3498 137/522 |
| 6,080,141 A | 6/2000 | Castro et al. | |
| 6,083,207 A | 7/2000 | Heck | |
| 6,120,494 A | 9/2000 | Jonkman | |
| 6,159,182 A * | 12/2000 | Davis | A61B 17/3462 604/167.03 |
| 6,179,813 B1 | 1/2001 | Ballow et al. | |
| 6,277,100 B1 | 8/2001 | Raulerson | |
| 6,436,070 B1 | 8/2002 | Botich et al. | |
| 6,461,362 B1 | 10/2002 | Halseth et al. | |
| 6,524,277 B1 | 2/2003 | Chang | |
| 6,569,120 B1 | 5/2003 | Green et al. | |
| 6,607,511 B2 | 8/2003 | Halseth et al. | |
| 6,641,564 B1 | 11/2003 | Kraus | |
| 6,692,462 B2 | 2/2004 | Mackenzie et al. | |
| 6,712,789 B1 | 3/2004 | Lange et al. | |
| 6,726,659 B1 | 4/2004 | Stocking et al. | |
| 6,783,516 B2 * | 8/2004 | O'Heeron | A61B 17/3498 604/167.03 |
| 6,808,520 B1 | 10/2004 | Fourkas et al. | |
| 6,942,671 B1 | 9/2005 | Smith | |
| 6,994,693 B2 | 2/2006 | Tal | |
| 7,001,396 B2 | 2/2006 | Glazier et al. | |
| 7,025,746 B2 | 4/2006 | Tal | |
| 7,083,626 B2 | 8/2006 | Hart et al. | |
| 7,101,353 B2 | 9/2006 | Lui et al. | |
| 7,163,525 B2 | 1/2007 | Franer | |
| 7,192,433 B2 | 3/2007 | Osypka et al. | |
| 7,270,649 B2 | 9/2007 | Fitzgerald | |
| 7,556,617 B2 | 7/2009 | Voorhees, Jr. et al. | |
| 7,717,878 B2 | 5/2010 | Smith | |
| 7,722,567 B2 | 5/2010 | Tal | |
| 7,744,569 B2 | 6/2010 | Smith | |
| 7,922,696 B2 | 4/2011 | Tal et al. | |
| 7,972,307 B2 | 7/2011 | Kraus et al. | |
| 7,993,305 B2 | 8/2011 | Ye et al. | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,827,958 B2 | 9/2014 | Bierman et al. | |
| 9,566,087 B2 | 2/2017 | Bierman et al. | |
| 2002/0065373 A1 | 5/2002 | Krishnan | |
| 2002/0072712 A1 | 6/2002 | Nool et al. | |
| 2002/0087076 A1 | 7/2002 | Meguro et al. | |
| 2004/0092879 A1 | 5/2004 | Kraus et al. | |
| 2004/0171988 A1 | 9/2004 | Moretti | |
| 2004/0267202 A1 | 12/2004 | Potter | |
| 2006/0015039 A1 | 1/2006 | Cassidy et al. | |
| 2006/0149293 A1 | 7/2006 | King et al. | |
| 2007/0123825 A1 | 5/2007 | King et al. | |
| 2008/0004569 A1 | 1/2008 | McCrystle et al. | |
| 2008/0097386 A1 | 4/2008 | Osypka | |
| 2008/0234728 A1 * | 9/2008 | Starksen | A61B 17/064 606/228 |
| 2008/0262431 A1 | 10/2008 | Anderson et al. | |
| 2009/0018508 A1 | 1/2009 | Fisher et al. | |
| 2009/0036843 A1 | 2/2009 | Erskine | |
| 2009/0143737 A1 | 6/2009 | Kobayashi et al. | |
| 2009/0177163 A1 | 7/2009 | King et al. | |
| 2009/0221961 A1 | 9/2009 | Tal et al. | |
| 2009/0227843 A1 | 9/2009 | Smith et al. | |
| 2009/0259186 A1 | 10/2009 | Smith et al. | |
| 2010/0042049 A1 | 2/2010 | Leeflang et al. | |
| 2011/0021994 A1 | 1/2011 | Anderson et al. | |
| 2011/0202006 A1 | 8/2011 | Bierman et al. | |
| 2011/0218496 A1 | 9/2011 | Bierman | |
| 2011/0276002 A1 | 11/2011 | Bierman | |
| 2011/0319838 A1 | 12/2011 | Goral | |
| 2012/0065590 A1 | 3/2012 | Bierman et al. | |
| 2012/0316500 A1 | 12/2012 | Bierman et al. | |

(56) References Cited

U.S. PATENT DOCUMENTS

| | | | |
|---|---|---|---|
| 2014/0207069 A1 | 7/2014 | Bierman et al. | |
| 2014/0276432 A1 | 9/2014 | Bierman et al. | |
| 2015/0126930 A1 | 5/2015 | Bierman et al. | |

FOREIGN PATENT DOCUMENTS

| | | |
|---|---|---|
| EP | 0 904 023 | 3/1999 |
| EP | 0 904 023 | 7/2004 |
| JP | 08-336593 | 12/1996 |
| JP | 2001-190682 | 7/2001 |
| JP | 2002-172174 | 6/2002 |
| KR | 10-2005-0027359 | 3/2005 |
| WO | WO 1998/00195 | 1/1998 |
| WO | WO 2003/057272 | 7/2003 |
| WO | WO 2004/000407 | 12/2003 |
| WO | WO 2008/131289 | 10/2008 |
| WO | WO 2009/114833 | 9/2009 |
| WO | WO 2011/097639 | 8/2011 |
| WO | WO 2012/135761 | 10/2012 |
| WO | WO 2012/162677 | 11/2012 |
| WO | WO 2013/026045 | 2/2013 |

OTHER PUBLICATIONS

International Search Report and Written Opinion of PCT/US2010/034609, dated Jan. 18, 2011.
International Search Report and Written Opinion for PCT Application No. PCT/US2012/051495 filed Aug. 17, 2012, dated Nov. 16, 2012.
Oct. 1, 2014 International Search Report and Written Opinion of Application No. PCT/US2014/26803 filed on Mar. 13, 2014.
Oct. 29, 2012 Extended European Search Report for European Application No. 10775500.1 filed May 12, 2010.
U.S. Appl. No. 14/207,120, Vascular Access Device, filed Mar. 12, 2014.
U.S. Appl. No. 13/319,998, Access Device with Valve, filed Sep. 9, 2014.
U.S. Appl. No. 14/207,120, Vascular Access Device, filed Feb. 14, 2017.
U.S. Appl. No. 14/480,286, Access Device with Valve, filed Sep. 8, 2014.
U.S. Appl. No. 15/232,144, Vascular Access Device, filed Aug. 9, 2016.

* cited by examiner

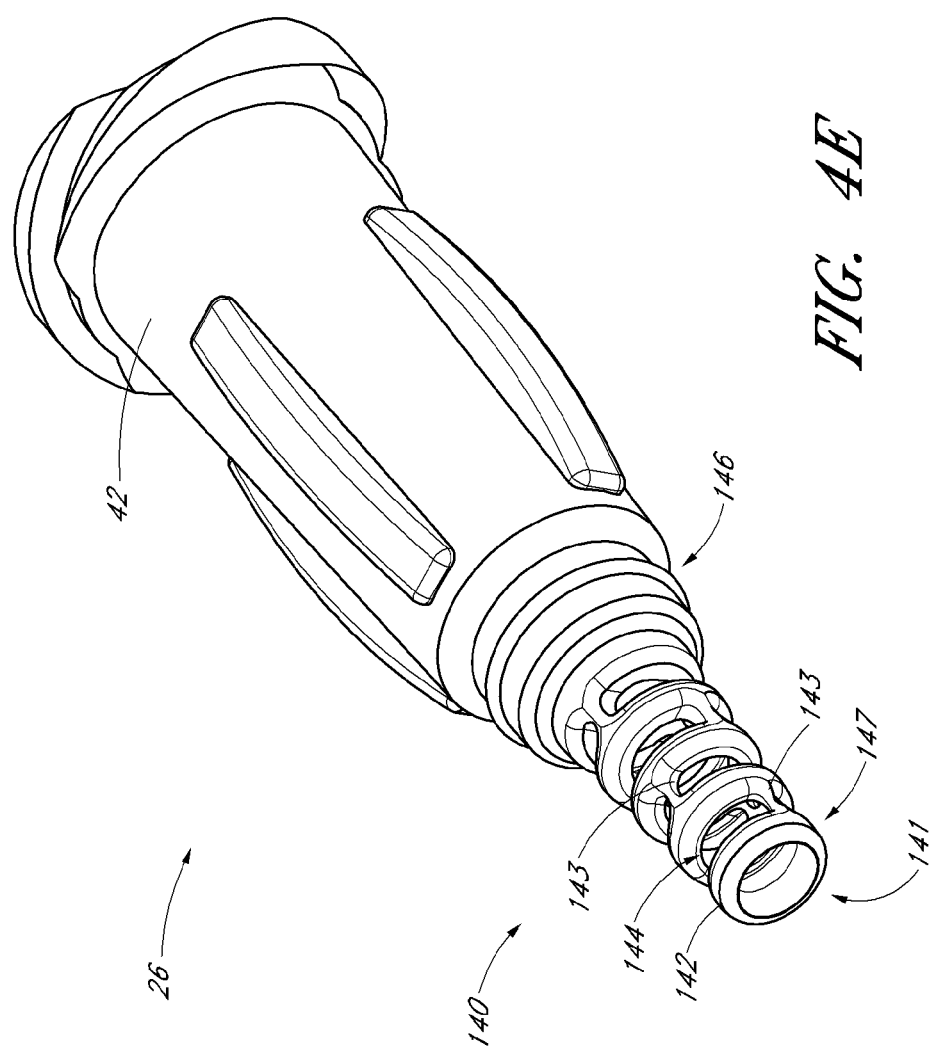

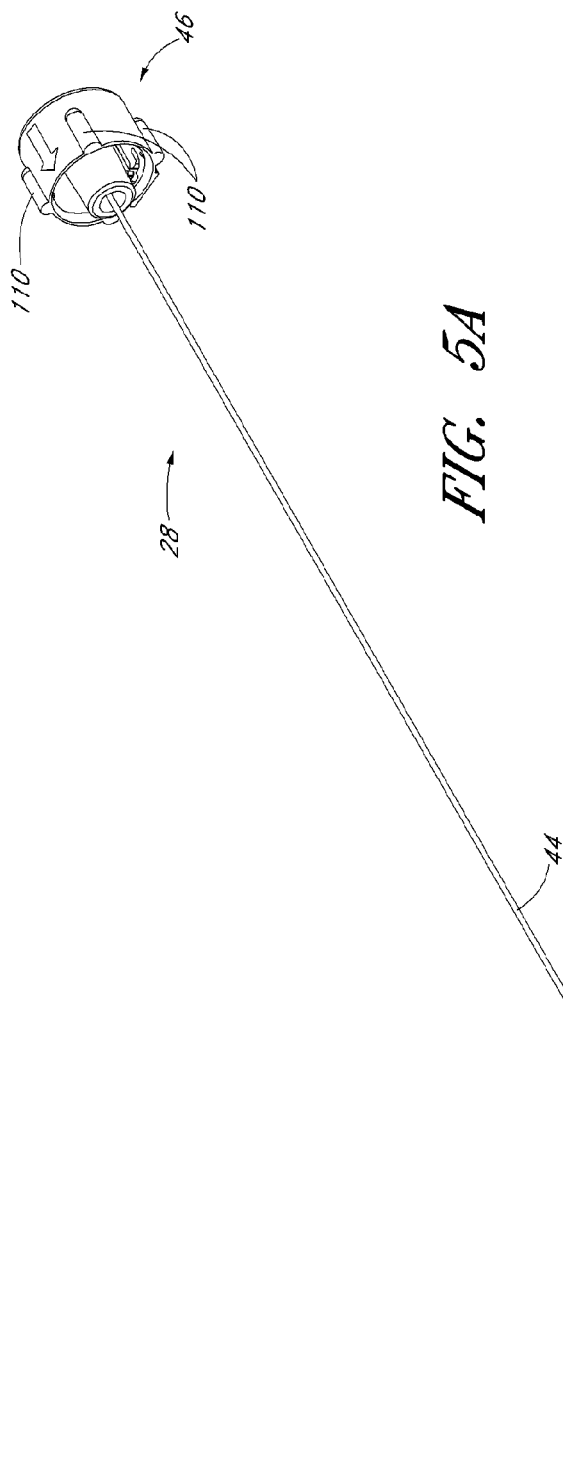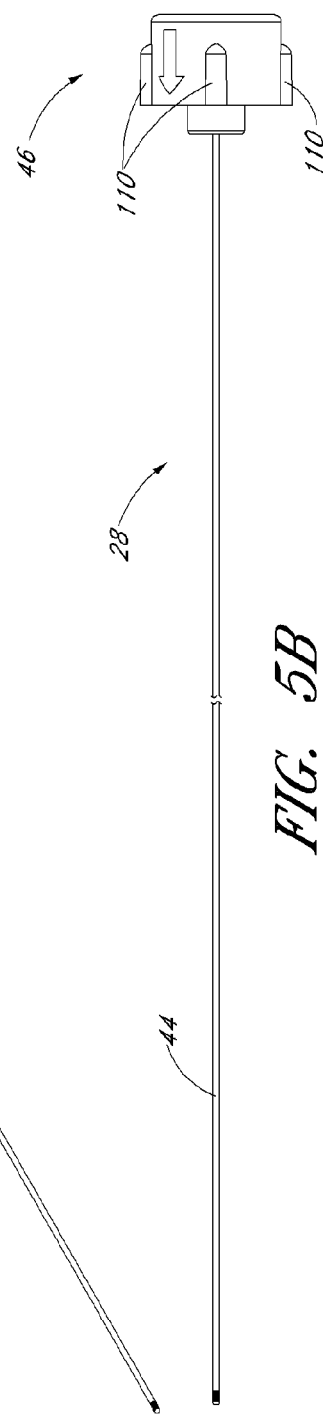
FIG. 5A
FIG. 5B

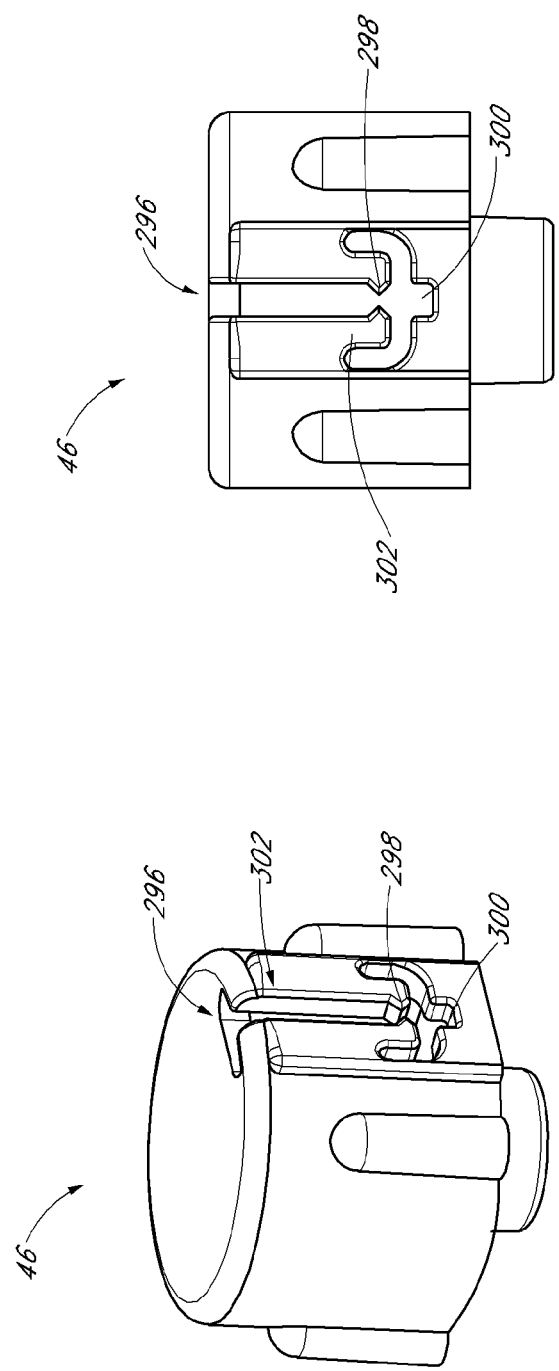

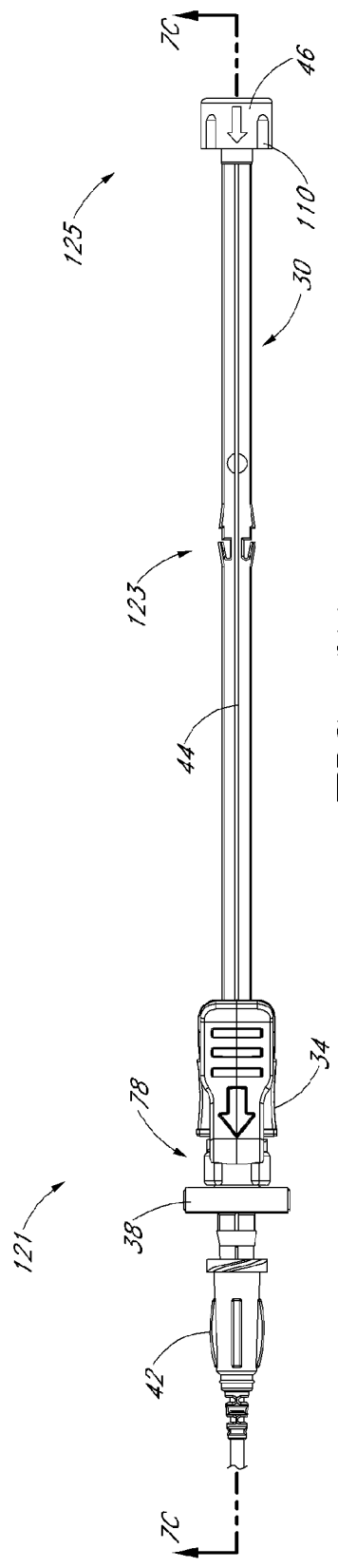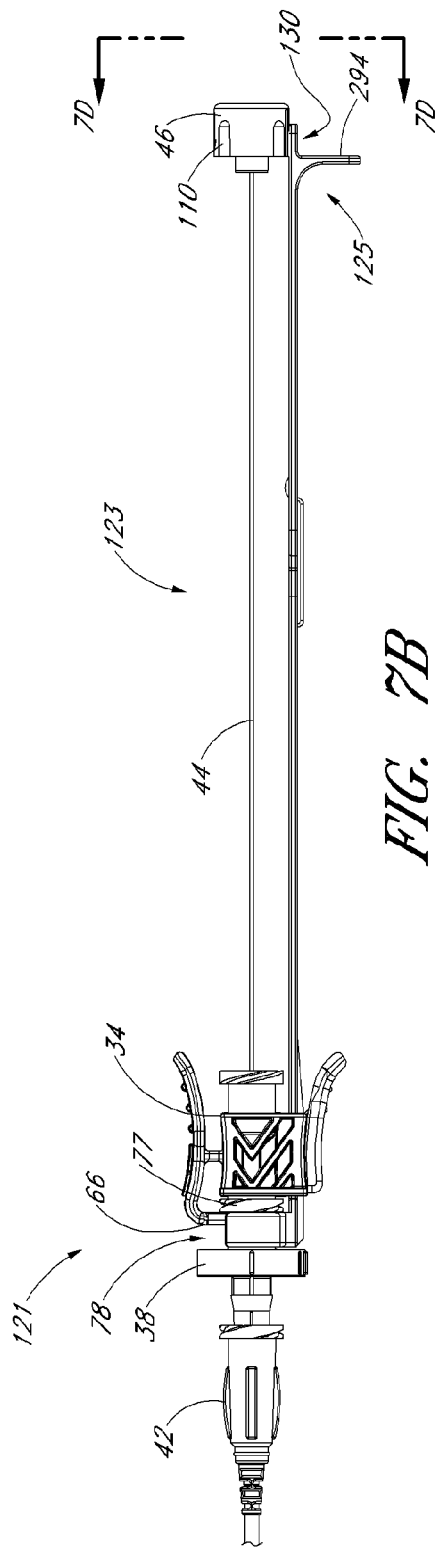

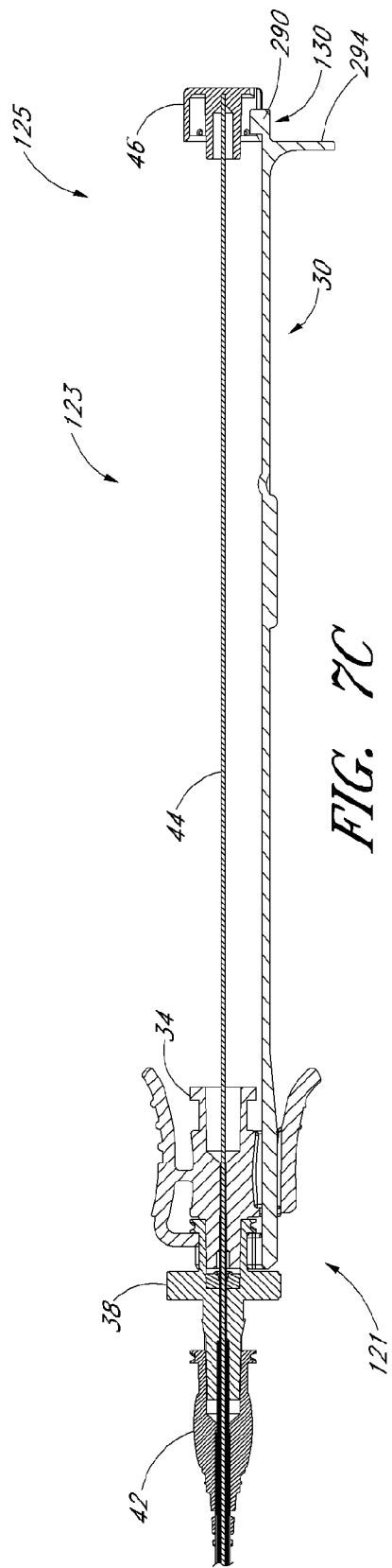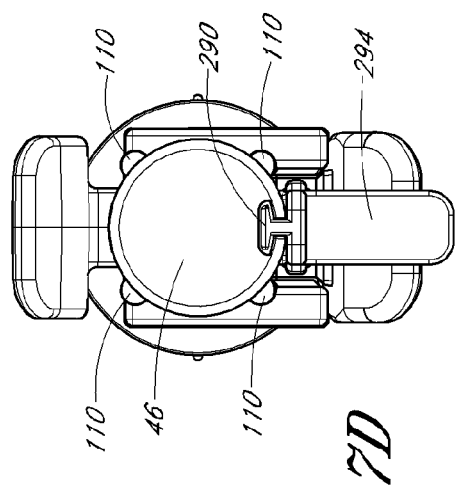
FIG. 7C
FIG. 7D

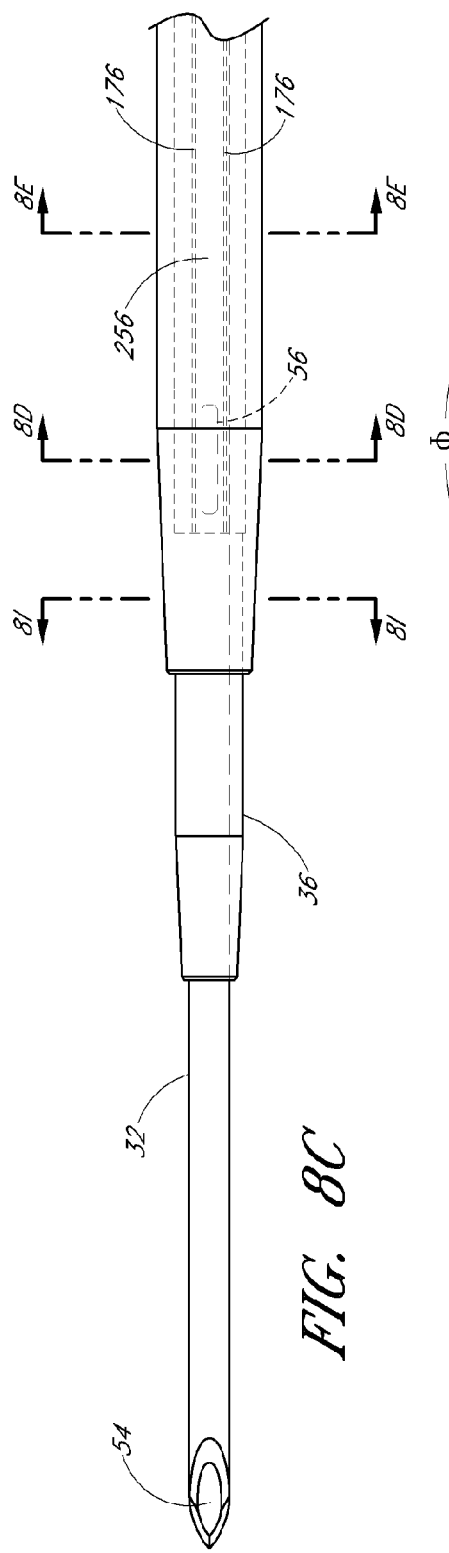
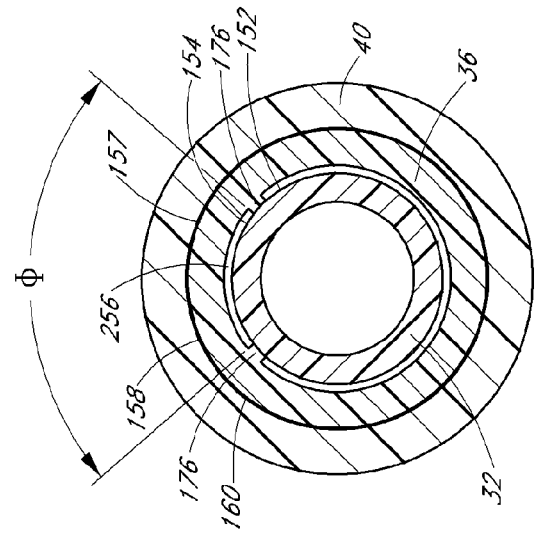
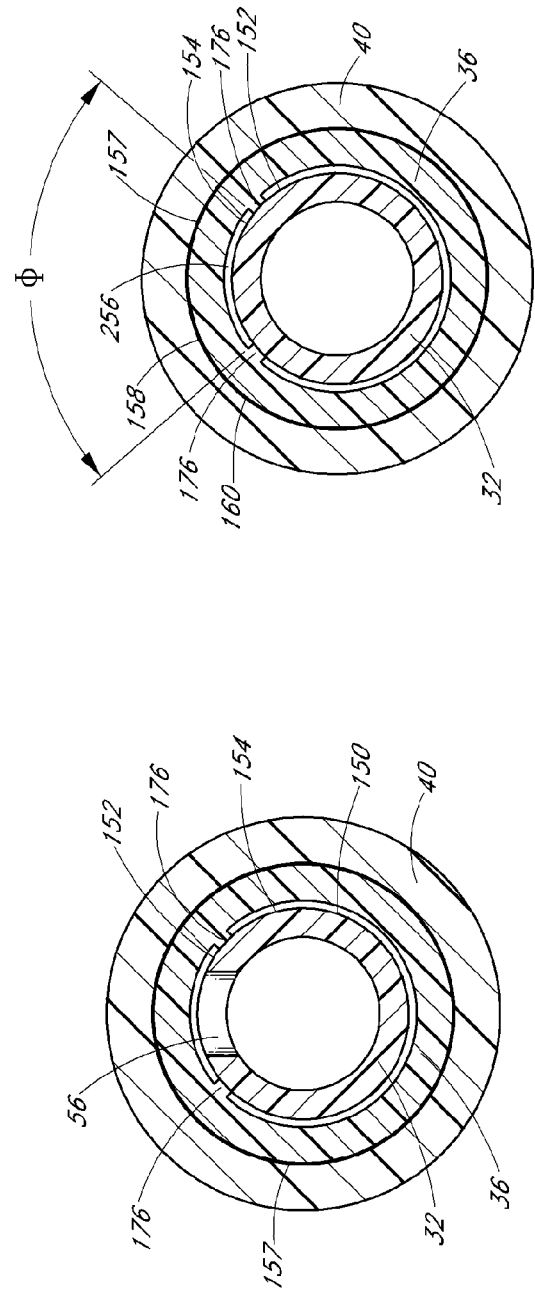

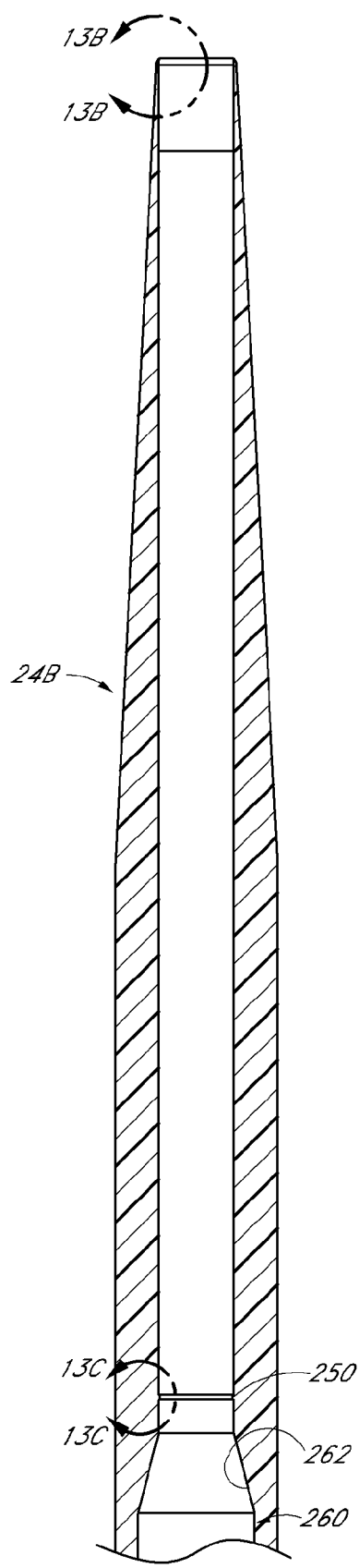
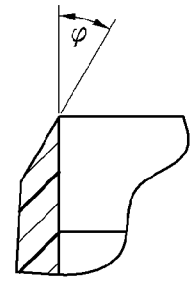
FIG. 13B
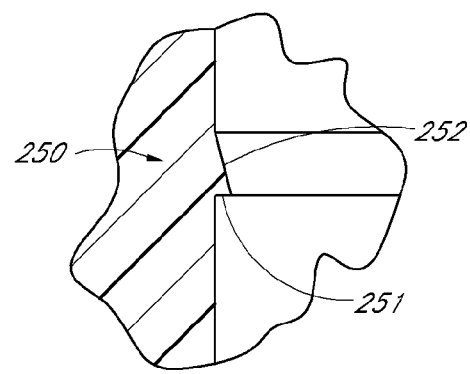
FIG. 13C
FIG. 13A

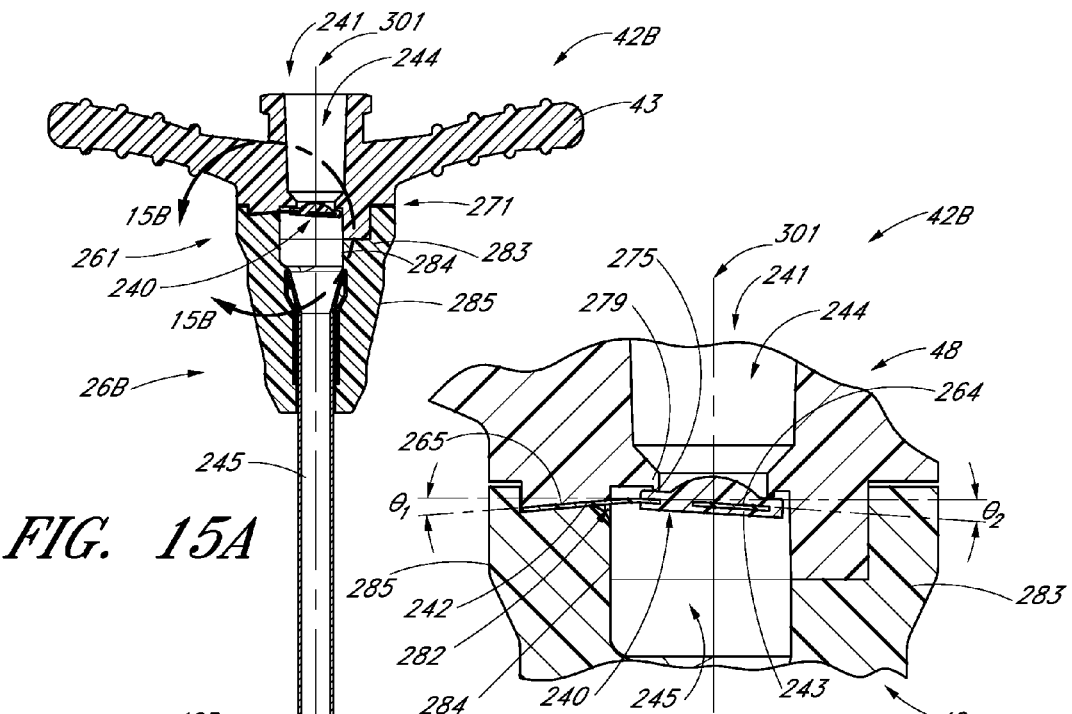
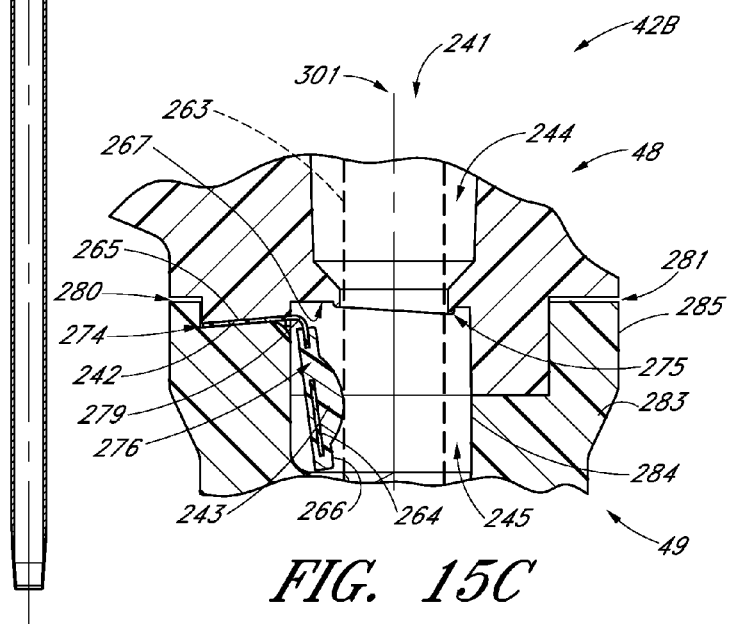
FIG. 15A
FIG. 15B
FIG. 15C

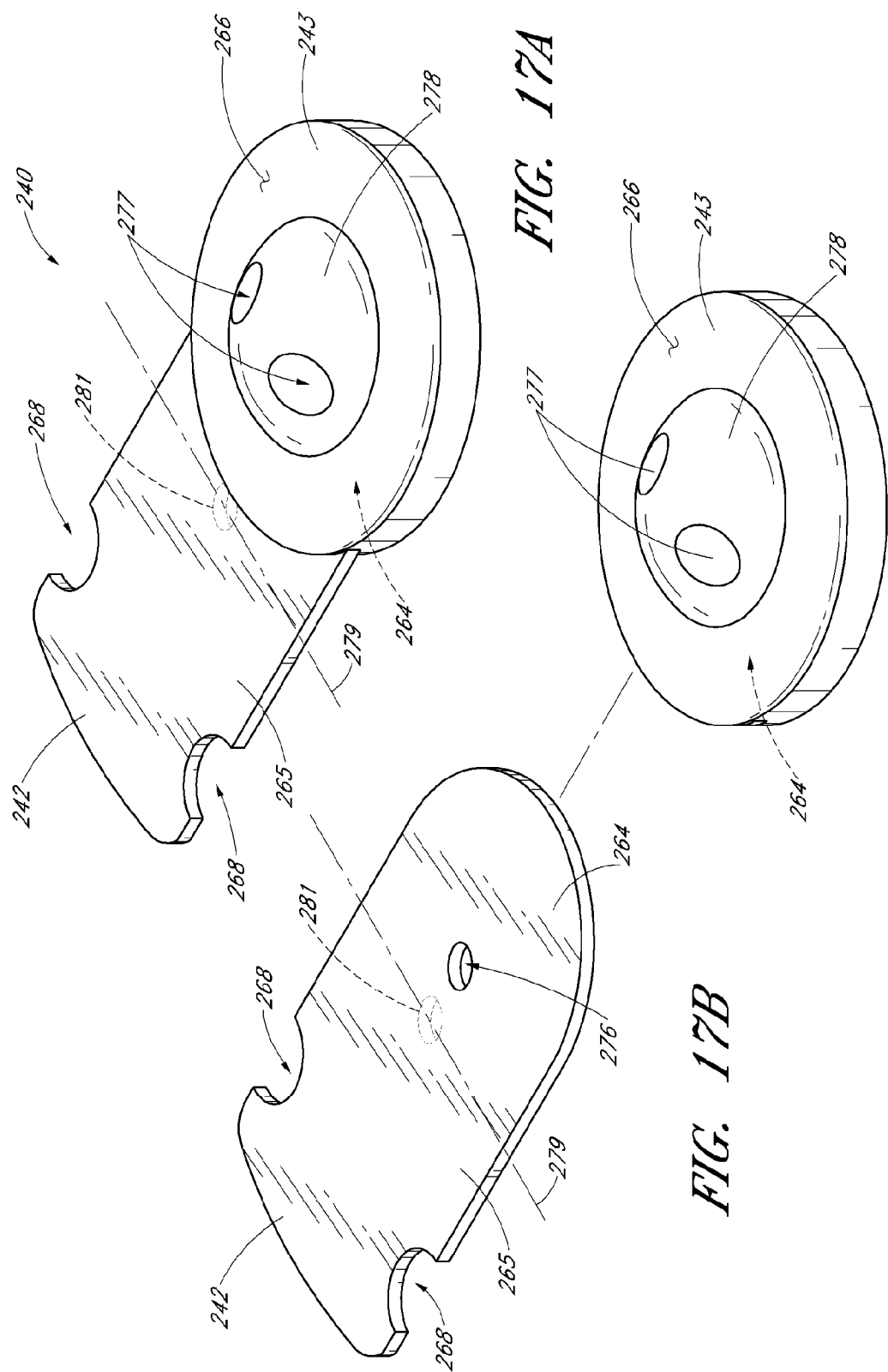

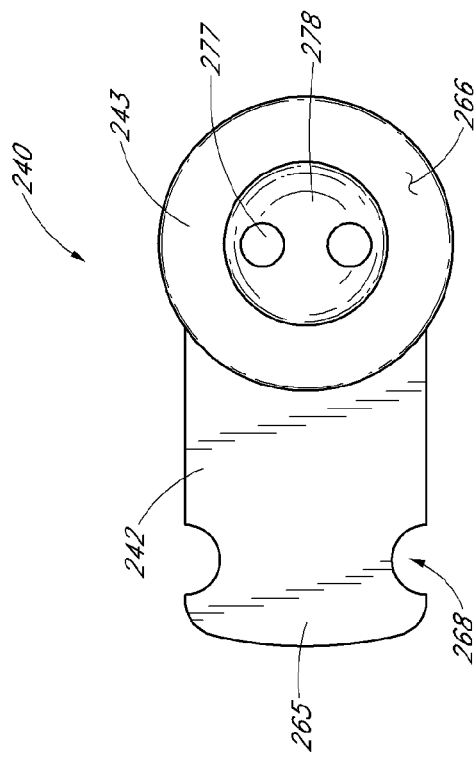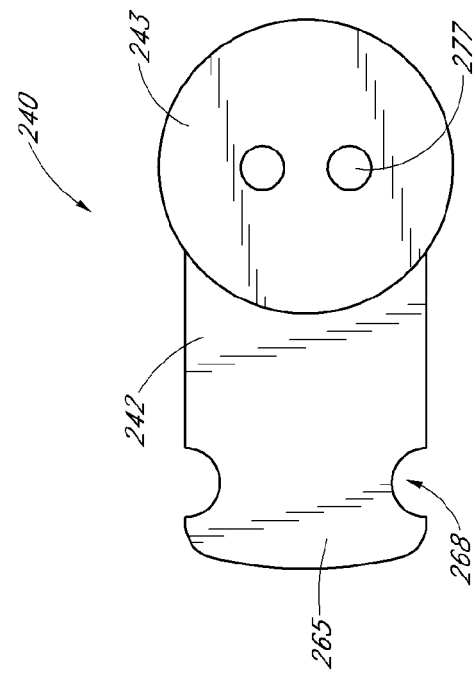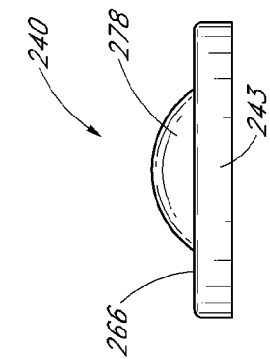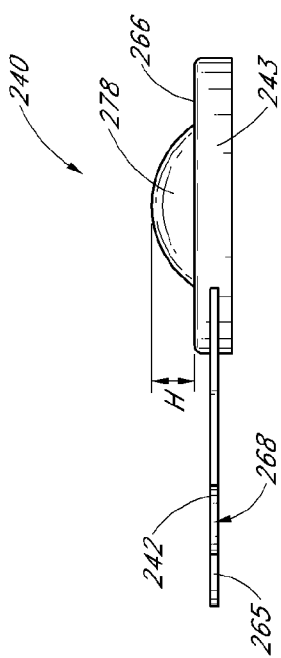

ACCESS DEVICE WITH VALVE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a National Phase Application of PCT International Application Number PCT/US2012/051495, filed Aug. 17, 2012, which claims priority to U.S. Provisional Patent Application No. 61/524,645, filed Aug. 17, 2011, each of which is hereby incorporated by reference in its entirety.

BACKGROUND

Field of the Invention

This invention is generally directed to access devices for introducing and/or delivering a medical article (such as, for example, a catheter, cannula, sheath, etc.) into a body space, such as, for example, an artery, vein, vessel, body cavity, or drainage site.

Description of the Related Art

A preferred non-surgical method for inserting a catheter or vascular sheath into a blood vessel involves the use of the Seldinger or a modified Seldinger technique, which includes an access needle that is inserted into a patient's blood vessel. A guidewire is inserted through the needle and into the vessel. The needle is removed, and a dilator and sheath in combination or separately are then inserted over the guidewire. The dilator and sheath, together or separately, are then inserted a short distance through the tissue into the vessel, after which the dilator and guidewire are removed and discarded. A catheter or other medical article may then be inserted through the sheath into the vessel to a desired location, or the sheath may simply be left in the vessel.

A number of vascular access devices are known. U.S. Pat. Nos. 4,241,019, 4,289,450, 4,756,230, 4,978,334, 5,124,544, 5,424,410, 5,312,355, 5,212,052, 5,558,132, 5,885,217, 6,120,494, 6,179,823, 6,210,332, 6,726,659 and 7,025,746 disclose examples of such devices. None of these devices, however, has the ease and safety of use that physicians and other healthcare providers would prefer.

SUMMARY

The described embodiments involve several features for an access device useful for the delivery of a catheter or sheath into a space within a patient's body, such as, for example, a blood vessel or drainage site. Without limiting the scope of this invention, its more prominent features will be discussed briefly. After considering this discussion, and particularly after reading the Detailed Description section below in combination with this section, one will understand how the features and aspects of these embodiments provide several advantages over prior access devices.

In one embodiment, a splittable sheath includes a splittable sheath body, a splittable sheath hub, and a valve element. The splittable sheath body can include a generally flexible tubular structure, a proximal end, and a distal end. The sheath body can define a longitudinal axis and can be splittable into two portions along a pre-determined line generally parallel to the longitudinal axis. The splittable sheath hub can extend from the proximal end of the sheath body and can define a longitudinal axis generally aligned with the longitudinal axis of the sheath body. The sheath body and sheath hub can form an inner cavity along their respective longitudinal axes. The valve element can include a resilient plate including a sealing portion extending radially inwardly from a side of the inner cavity. The valve element can include a sealing element including a first sealing surface supported by the resilient plate such that the sealing element is biased toward a position against a second sealing surface on at least one of the splittable sheath body and hub to substantially seal the inner cavity.

In one embodiment, an access device includes a needle, a dilator, a splittable sheath, and a valve element. The splittable sheath can include a splittable sheath body and a splittable sheath hub extending from a proximal end of the sheath body. The sheath body and sheath hub can form an inner cavity along a longitudinal axis defined by the sheath body and sheath hub. The valve element can include a resilient plate and a sealing element. The resilient plate can include a sealing portion extending radially inwardly from a side of the inner cavity. The sealing element can include a sealing surface and can be supported by the resilient plate. The sealing element can be biased toward a first position against a second sealing surface on at least one of the splittable sheath body and hub to substantially seal the inner cavity. The sealing element can be movable from the first position to a second position when at least one of the needle and dilator are extended through the cavity, without substantial contact between the at least one of the needle and dilator and the first sealing surface.

In one embodiment, an access device includes a valve element that includes a resilient plate and a sealing element. The resilient plate can be adapted to reside within an inner cavity of at least one of a splittable sheath body and hub. The sealing element can include a dome-like shaped raised portion and a sealing surface extending around a perimeter of the raised portion. The sealing element can be biased toward a position against a second sealing surface on at least one of a splittable sheath body and a hub to substantially seal an inner cavity of at least one of a splittable sheath body and a hub.

In one embodiment, a splittable sheath includes a splittable sheath body, a splittable sheath hub, and a valve element. The splittable sheath body can include a generally flexible tubular structure, a proximal end, and a distal end. The splittable sheath hub can extend from the proximal end of the sheath body. At least one of the sheath body and the sheath hub can be splittable into two portions along a pre-determined line generally parallel to a longitudinal axis defined by the at least one of the sheath body and the sheath hub. The sheath body and sheath hub can form an inner cavity. The valve element can include a resilient plate including a mounting portion and a sealing portion extending radially inwardly from a side of the inner cavity and the mounting portion. The valve element can include a sealing element supported by the resilient plate such that the sealing element is biased toward a position against the at least one of the splittable sheath body and hub to substantially seal the inner cavity. The resilient plate can be supported by a first of the two splittable sheath portions such that the valve element is separable from a second of the two splittable sheath portions.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the access device disclosed herein are described below with reference to the drawings of preferred embodiments, which are intended to illustrate and not to limit the invention. Additionally, from figure to figure, the same reference numerals have been used to designate the same components of an illustrated embodiment. Like components between the illustrated embodiments are similarly noted as the same reference numbers with a letter suffix to indicate another embodiment. The following is a brief description of each of the drawings.

FIG. 4E is an enlarged perspective view of a proximal portion of the sheath from FIG. 4A with a sheath body removed for clarity and including an embodiment of a relief element.

FIG. 5A is a perspective view of the guidewire section from FIG. 1A and shows a guidewire hub connected to a proximal end of a guidewire.

FIG. 5B is a plan view of the guidewire section of the embodiment depicted in FIG. 5A.

FIG. 5C is a perspective view of another embodiment of a guidewire hub.

FIG. 5D is a bottom view of the guidewire hub of FIG. 5C.

FIG. 7A is a plan view of the access device from FIG. 1A and shows the locking mechanism from FIG. 6D with the guidewire section locked to the track in the pre-loaded state.

FIG. 7B is a side view of the access device and locking mechanism from FIG. 7A.

FIG. 7C is a cross-sectional side view through the access device of FIG. 7A.

FIG. 7D is an enlarged end view of the access device from FIG. 7B.

FIG. 8C is an enlarged view of a portion of the embodiment depicted in FIG. 8B and illustrates a needle opening in hidden lines.

FIG. 8D is an enlarged cross-sectional view of a portion of the embodiment depicted in FIG. 8C and shows the needle opening or fenestration so as to allow fluid to flow from inside the needle to a channel formed between the needle and dilator.

FIG. 8E is an enlarged cross-sectional view of the embodiment depicted in FIG. 8C proximal to the needle opening along line 8E-8E.

FIG. 13A is a cross-sectional view of the distal portion of a dilator of FIG. 3A.

FIG. 13B is an enlarged view of a section of the dilator of FIG. 13A taken at 13A-13A.

FIG. 13C is an enlarged view of a section of the dilator of FIG. 13A taken at 13C-13C.

FIG. 15A is a side cross-sectional view of the sheath of FIG. 14A taken at 15A-15A.

FIGS. 15B-15C are enlarged views of a section of the sheath of FIG. 15A showing a valve element in a closed and opened position, respectively.

FIG. 17A is a side isometric view of an embodiment of a valve element of the sheath shown in FIGS. 14A-14B.

FIG. 17B is an exploded isometric view of the valve element shown in FIG. 17A.

FIG. 18 is a bottom view of the valve element shown in FIG. 17A.

FIG. 19 is a top view of the valve element shown in FIG. 17A.

FIG. 20 is a rear view of the valve element shown in FIG. 17A.

FIG. 21 is a side view of the valve element shown in FIG. 17A.

FIG. 22 is a front view of the valve element shown in FIG. 17A.

DETAILED DESCRIPTION

Figure 1A:
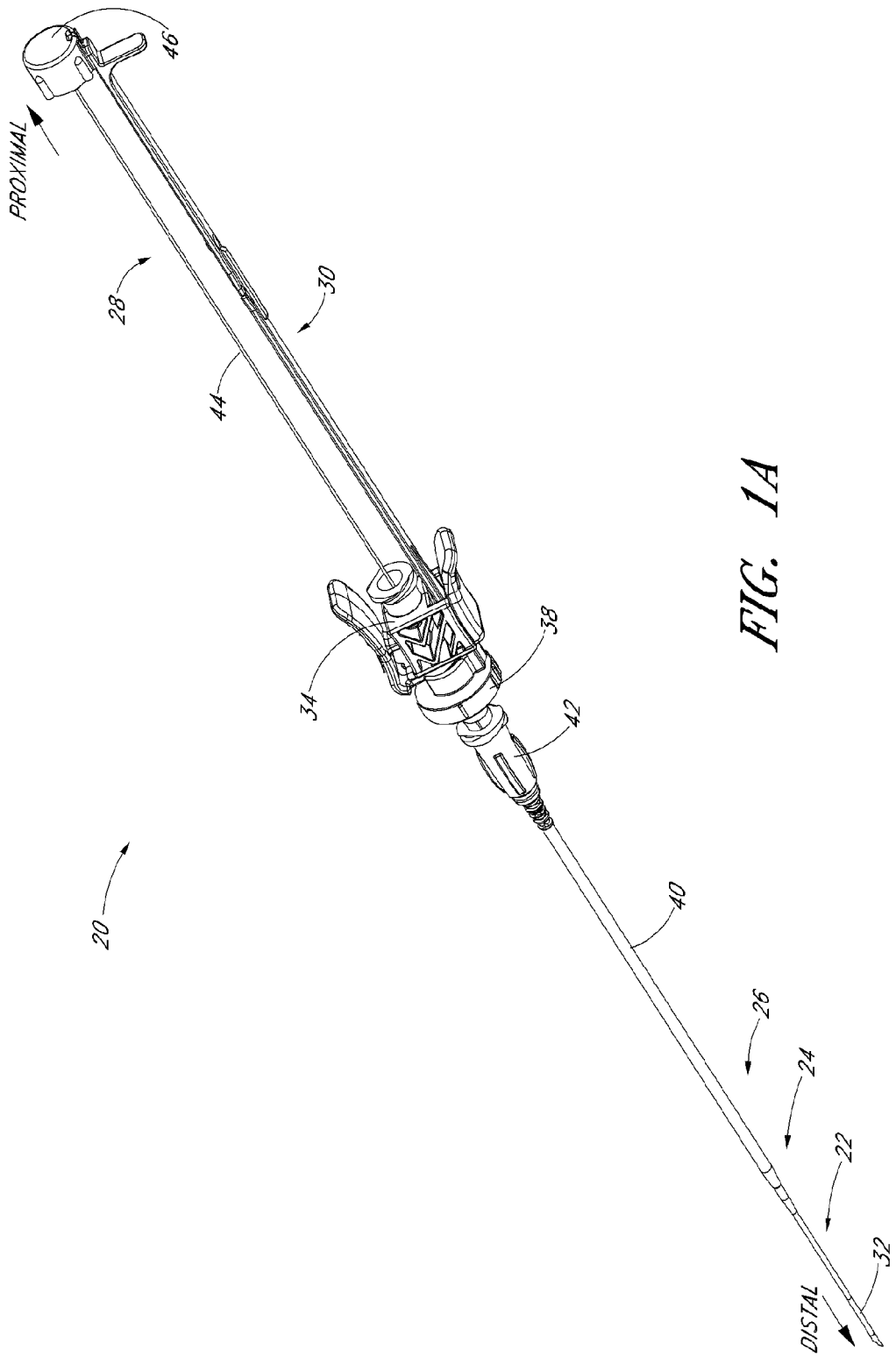
FIG. 1A is a perspective view of an embodiment of an access device showing a pre-loaded guidewire section coaxially aligned with a needle, a dilator, and a medical article.

The present disclosure provides an access device for the delivery of an article such as a medical article (e.g., catheter or sheath) to a space such as a blood vessel or drainage site. FIG. 1A illustrates an access device 20 that is configured to be inserted into a blood vessel (e.g., a vein or an artery) in accordance with a preferred embodiment of the present invention. While the access device is described below in this context (i.e., for vascular access), the access device also can be used to access and place a medical article (e.g., catheter or sheath) into other locations within a patient's body (e.g., a drainage site) and for other purposes (e.g., for draining an abscess).

The present embodiment of the access device is disclosed in the context of placing an exemplary single-piece, tubular medical article into a body space within a patient. Once placed, the tubular article can then be used to receive other medical articles (e.g., catheters, guidewires, etc.) to provide access into the body space and/or be used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood in light of the present disclosure that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access device disclosed herein can also be configured to directly or indirectly place central venous catheters, peripherally inserted central catheters, hemodialysis catheters, surgical drainage tubes, tear-away sheaths, multi-piece sheaths, PICC lines, IV lines, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

Figure 1B:
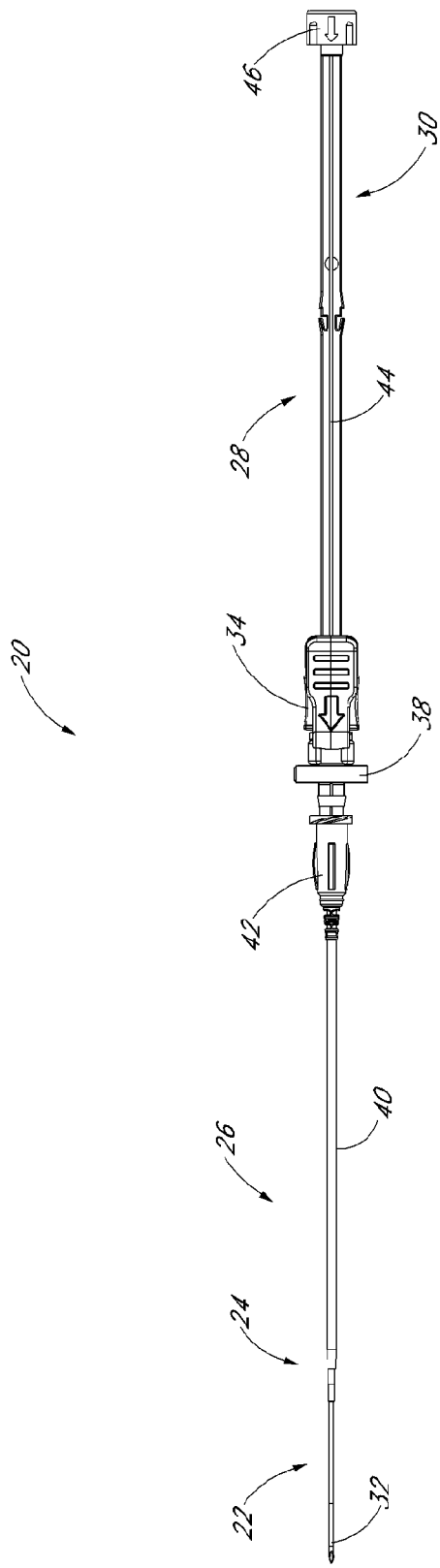
FIG. 1B is a plan view of the embodiment depicted in FIG. 1A.

FIGS. 1A and 1B illustrated a preferred embodiment of an access device 20. The access device 20 comprises a needle 22, a dilator 24, and a sheath 26. In the illustrated embodiment, the access device also includes a guidewire section 28 and a track 30. As best seen in FIG. 1B, the dilator 24 can be coaxially mounted on the needle 22, and the sheath 26 is coaxially mounted on the dilator 24. The telescoping nature of the access device's components can also be accomplished by arranging the components with their axes arranged substantially parallel rather than coaxially (e.g., a monorail-type design).

Each of these components includes a luminal fitting at a terminal end or transition (i.e., a hub) and elongated structure that extends from the fitting. Thus, in the illustrated embodiment, the needle 22 includes a needle body 32 that extends distally from the needle hub 34, the dilator 24 includes a dilator shaft 36 that extends distally from a dilator hub 38, and the sheath 26 includes a sheath body 40 that extends distally from a sheath hub 42. The guidewire section 28 comprises a guidewire 44 and preferably a guidewire hub or cap 46. In the illustrated embodiment, the guidewire hub 46 is disposed on the proximal end of the guidewire 44; however, in other applications, the hub 46 can be disposed at a location between the ends of the guidewire 44.

Figure 2A:
FIG. 2A is a plan view of the needle from FIG. 1A and shows a fenestration near a distal end.
Figure 2B:
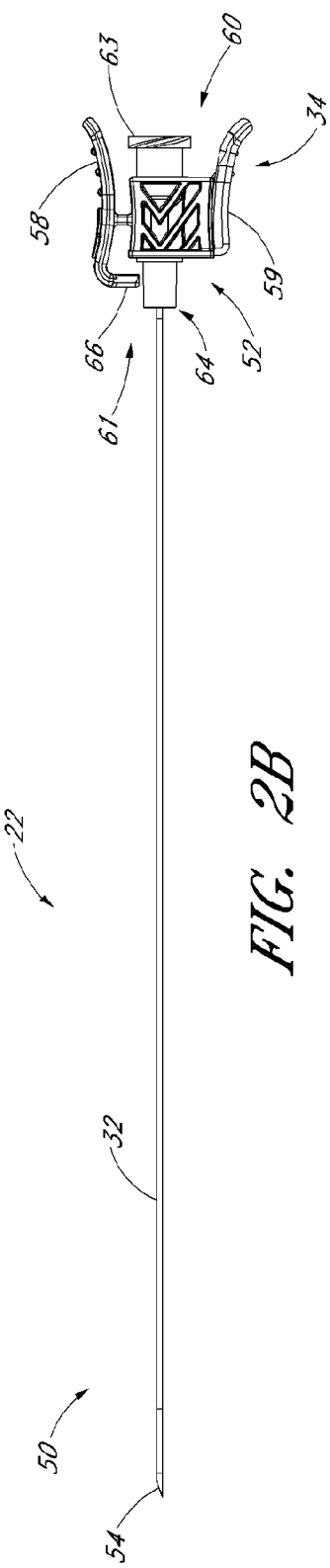
FIG. 2B is a side view of the needle from FIG. 1A and shows a handling portion near a proximal end.

FIGS. 2A-2G illustrate the needle body 32 and needle hub 34 of the needle 22, which are configured in accordance with an embodiment of the access device, in isolation from the other components of the access device 20. As best seen in FIGS. 2A and 2B, the needle hub 34 is disposed on a proximal end of the needle body 32. The needle body 32 terminates at a distal end near a distal portion 50 of the needle 22, and the needle hub 34 lies at a proximal portion 52 of the needle 22.

The needle body 32 preferably has an elongated tubular shape having a circular, constant-diameter inner bore and a circular, constant-diameter exterior surface. In other embodiments, however, the needle body 32 can have other bore and exterior shapes (such as, for example, but without limitation, an oval cross-sectional shape). The interior or exterior of the needle can also include grooves or channels. The grooves or channels may guide fluids within the needle bore either around or to certain structures of the needle 22 or within the needle 22 (e.g., around the guidewire). In some embodiments, the grooves or channels may assist in maintaining a desired orientation of the needle 22 with respect to the dilator.

The needle body 32 has a sufficiently long length to access a targeted subcutaneous body space and has a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the needle body 32 preferably has a length of 7 cm or greater, and more preferably has a length of 9 cm or greater, and most preferably has a length of 9 to 10 cm. The size of the needle preferably is 18 gauge or smaller, and more preferably between 18-28 gauge, and most preferably between 18-26 gauge for micro-puncture applications (e.g., peripheral IVs). For applications with a neonate, the length and gauge of the needle body 32 should be significantly shorter and smaller, for example preferably between 3-4 cm and between 26-28 gauge.

Figure 2C:
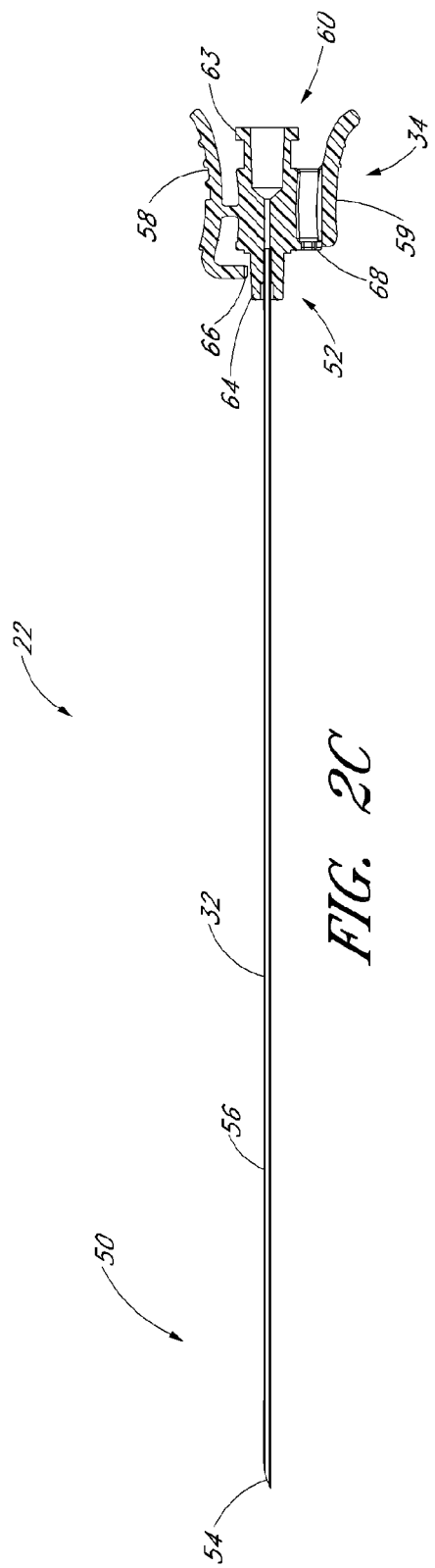
FIG. 2C is a cross-sectional view taken along the lines 2C-2C in FIG. 2A.
Figure 2D:
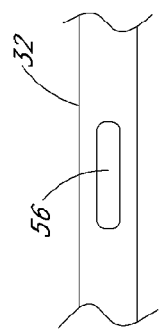
FIG. 2D is an enlarged plan view of a portion of the needle of FIG. 2A and shows the fenestration.

As best seen in FIGS. 2A and 2D, the needle body 32 can include a bevel tip 54 disposed on the distal portion 50. Further, in some embodiments the needle body 32 can include at least one fenestration or opening 56 near a distal end of the needle body 32. In some embodiments, the needle body 32 and/or the dilator shaft 36 may have multiple side fenestrations or openings. In embodiments wherein both the needle body 32 and/or the dilator shaft 36 have openings, some or all of these openings can be rotationally aligned.

The fenestration 56 extends, or provides a path, through the wall or side of the needle body 32. As described further herein, the fenestration 56 can allow for a fluid such as blood to flow between a portion of needle body 32 and a portion of dilator 24 (FIGS. 3A-3D) during the use of access device 20. The fenestration 56 can have a variety of shapes and orientations on the needle body 32. For example, the fenestration 56 illustrated in FIG. 2D has an oblong shape. However, the shape of the side opening 56 is not limited to the illustrated embodiment and may be round, oblong, square, or another shape, as shown, for example, in PCT International Patent Application No. PCT/US2011/024097, filed Feb. 8, 2011, hereby incorporated by reference in its entirety herein.

As is illustrated in FIGS. 2A and 2B, needle hub 34 can include one or more handling portions 58, 59 to provide a grasping region to manipulate the needle hub 34. For example, a physician or healthcare provider can place an index finger and thumb on the approximately opposed sides of the handling portions 58, 59 to stabilize the needle hub 34, relative to the dilator 24 and/or sheath 26. In the illustrated embodiment, as the dilator/sheath slides distally over the needle, the needle hub 34 slides relatively along the track 30 between a first position 121 and a second position 123 (example portions illustrated in FIG. 6A). The handling portions 58, 59 can be held when performing the insertion step (which will be described below). In addition, the handling portions 58, 59 can be used to stabilize the needle hub 34 while rotating the dilator hub 38. Furthermore, the handling portions 58, 59 can be used by a physician or healthcare provider as an aid to grasp the access device 20 when the needle hub 34 is disposed at any position along the track 30. In some embodiments, either or both of the handling portions 58, 59 can include one or more optional latch elements to couple the needle hub 34 to another component of access device 20, as described further below.

The one or more handling portions 58, 59 can be formed integrally or separately from the remainder of needle hub 34. For example, it may be beneficial to separately form handling portion 58 and/or 59 from the remainder of needle hub 34, to facilitate mounting of the remainder of needle hub 34 to track 30 (see, e.g., FIGS. 1A and 6A), in a first assembly step, and mounting of handling portion 58 and/or 59 to the remainder of needle hub 34 in a second assembly step. For example, referring to FIGS. 2G and 1A, the handling portion 59, along with the remainder of the needle hub 34, can be configured to span entirely around the track 30 when mounted to the track 30. Thus, for example, the needle hub 34 can be substantially prevented from removal from the track 30 unless the handling portion 59 is removed. Advantageously, in some embodiments the handling portion 59 that does not include the latch element 66 can be added after mounting to the track 30, such that the other handling portion 58, which may include the latch element 66, can be pivotally formed integrally with other portions of the needle hub 34.

Figures 10A, 10B:
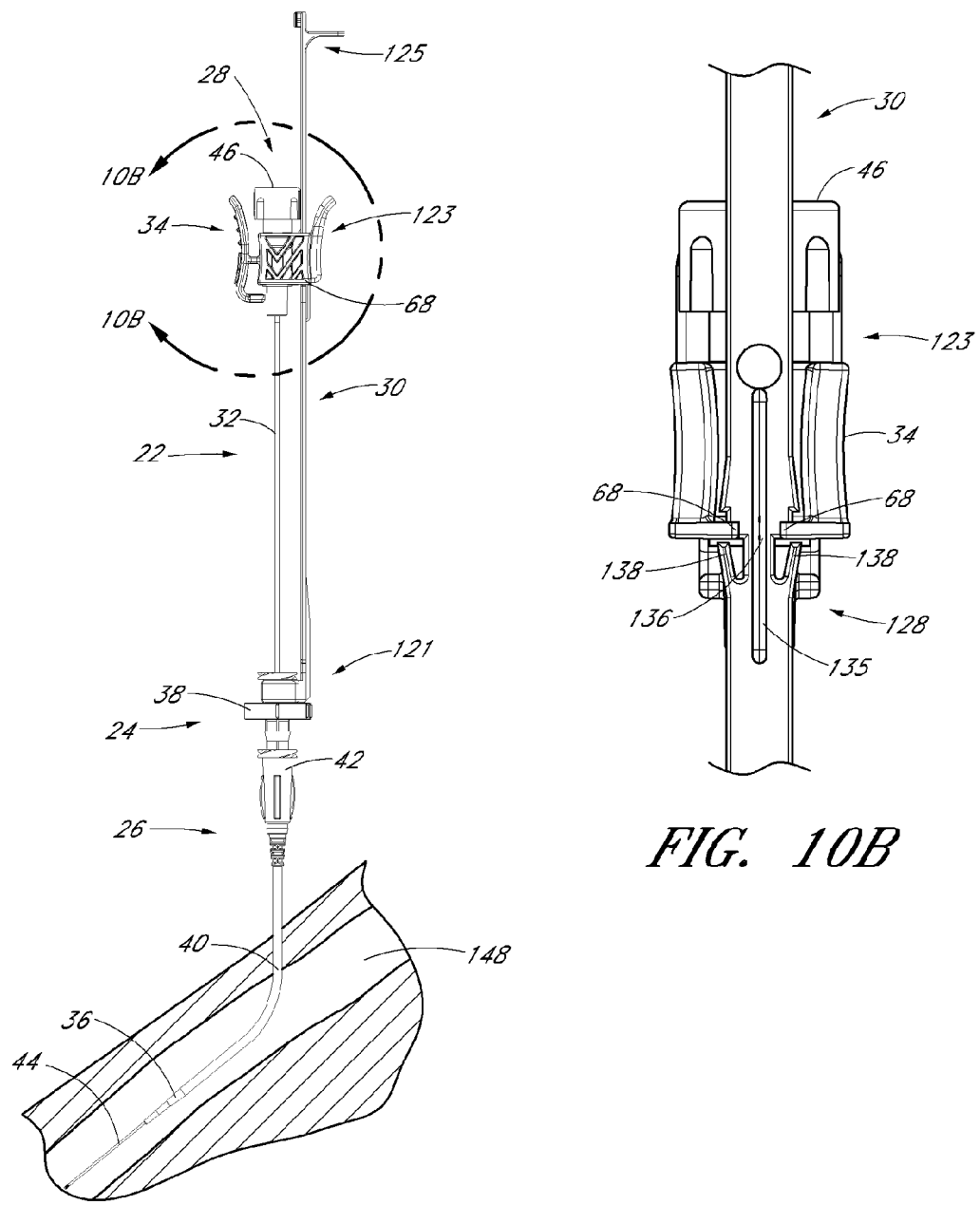
FIG. 10A is a side view of the embodiment depicted in FIG. 1A illustrating the dilator and sheath being advanced distally relative to the needle body from the position illustrated in FIG. 9A.
FIG. 10B is an enlarged bottom view of the embodiment depicted in FIG. 10A focusing on the area where the needle hub is locked to the track when the needle hub is in the second position.

The one or more handling portions 58, 59 can be releasably or permanently attached to the remainder of needle hub 34, to control the ease with which needle hub 34 is disengaged from track 30. For example, handling portions 58, 59 can be releasably attachable to the remainder of needle hub 34, to allow the disassembly of handling portion(s) 58, 59 from the remainder of needle hub 34 in a first disassembly step, allowing needle hub 34 to be dismounted from track 30. Conversely, handling portions 58, 59 can be permanently attachable to the remainder of needle hub 34, to prevent the removal of needle hub 34 from track 30 after the initial assembly process. Preventing needle hub 34 from being removed from track 30 prevents the reuse of access device 20, which could cause infection. Further, preventing needle hub 34 from being removed from track 30 can more reliably retain the needle in the second position 123, as depicted in FIGS. 10A, 10B and further described below, reducing the possibility of accidental needle stick.

The one or more handling portions 58, 59 can be disposed at a circumferential location around the needle hub 34 that is aligned with the circumferential locations of the bevel 54 on the needle tip and/or one of the at least one opening or fenestration 56 in the needle.

In the illustrated embodiment, the handling portion 58 is indexed with the bevel 54 and fenestration 56. Additionally, as shown most clearly in FIG. 2A, needle hub 34 can include color coding, words, or other indicia, such as an arrow, to indicate to the operator the orientation of the bevel tip 54 or the fenestration 56 of needle body 32 relative to the dilator 24 or the sheath section 26. During use, the physician or healthcare provider can determine the orientation of the beveled needle tip (and the fenestration 56) by noting the orientation of the exposed handling portion 58 even though the bevel is inside the vessel and the fenestration is covered by the sheath and/or dilator. For example, in the illustrated embodiment, an orientation of the handling portion 58 away from the patient coincides with a bevel up orientation of the needle tip within the vessel. The illustrated fenestration 56 is also on the same side as the handling portion 58, as seen in FIG. 2C.

FIG. 2D is an enlarged view of the side opening or fenestration 56 in the needle body 32. The one or more fenestration 56 provides a path through the side of the needle body 32. The fenestration 56 illustrated in FIG. 2D has an oblong shape. The shape of the side opening 56, however, is not limited to the illustrated embodiment and may be round, oblong, square, or another shape.

Referring to FIGS. 2A-2C and 2E-2G, the needle hub 34 can include locking structures at the proximal portion 60 and distal portion 61 of the needle hub 34. These locking structures may be a luer-type, thread-type, latch-type, other types of connections, or a combination thereof.

The locking structure on the proximal portion 52 of the needle hub 34 can allow the physician or healthcare provider to secure (e.g., releasably secure) another medical article to the proximal end 60 of the needle hub 34. For example, the needle hub 34 in the illustrated embodiment includes an annular flange or lip 63. The lip 63 is threaded to allow the needle hub 34 to attach to other medical articles with a corresponding threaded locking feature. Additionally, a physician or healthcare provider may attach a syringe or monitoring equipment to the locking structure on the proximal end to perform other procedures as desired. The needle hub 34 can also include a septum at its proximal end and/or a side port if these features are desirably for a particular application.

Figure 6A:
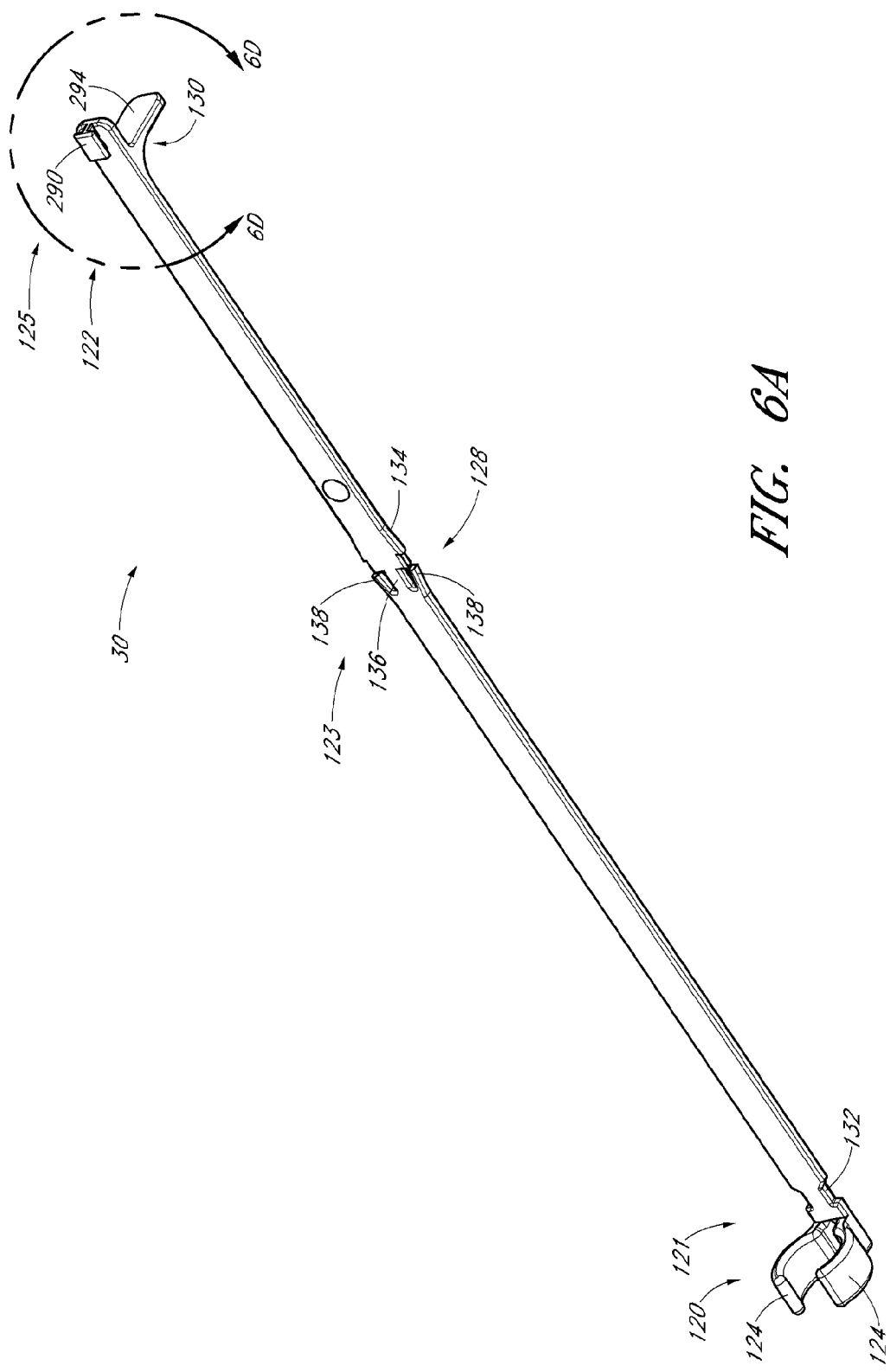
FIG. 6A is a perspective view of a track from FIG. 1A.

The locking structure on the distal portion 61 of the needle hub 34 can allow the physician or healthcare provider, for example, to lock the needle hub 34 to a medical article such as the dilator hub 38 (see, e.g., FIGS. 1A-1B) when the needle hub 34 is in the first position 121 (see, e.g., FIG. 6A). Referring again to the illustrated embodiment in FIGS. 2A-2C and 2E-2G, the locking structure includes a latch element 66 coupled to handling portion 58. Handling portion 58 can be pivotably coupled to the remainder of needle hub 34, to allow latch element to releasably engage and secure to a corresponding portion of the dilator hub 38, such as a lip 77 (FIG. 7B).

As such, the latch element 66 releasably locks the needle hub 34 to the dilator hub 38. The locking structure allows the healthcare provider to advance the needle into a patient while grasping one of the needle hub 34 and the dilator hub 38, or both. In some embodiments, the portions of the dilator hub 38 onto which the latch element 66 engages can include one or more flats to inhibit rotation of the needle hub 34 relative to the dilator hub 38. An embodiment of a dilator hub 38 which includes a flat 33 positioned on an annular groove 33 that can engage with latch element 66 and inhibit rotation of the needle hub 34 is shown in FIG. 3E. In some embodiments, the flats can inhibit such rotation after a certain degree of relative rotation (e.g., 180 degrees) between the needle hub 21 and the dilator hub 32.

In certain embodiments, the latch element 66 is configured to provide a bias towards the center of the needle hub 34. Preferably, the bias prevents the secured part (e.g., the dilator hub 38) from slipping or disengaging from latch element 66. More preferably, the bias of latch element 66 can be overcome by applying pressure to handling element 58, to release latch element 66. To apply the appropriate releasing pressure, a physician or healthcare provider may, for example, place an index finger and thumb on the opposed sides of handling elements 58, 59 and apply squeezing pressure to overcome the hinge bias.

Handling portions 58, 59 and locking portions/latch element 66 can comprise any of a number of different shapes and are not limited to the particular embodiments disclosed herein. For example, PCT International Patent Application No. PCT/US2011/024097, filed Feb. 8, 2011, hereby incorporated by reference in its entirety herein, discloses a radially-extending fin and a rotational hook-shaped latch element on a needle hub that can engage with corresponding openings on a dilator hub that can be used to facilitate the handling of the embodiments of the access device described herein. U.S. Patent Application Publication No. 2008-0294111, filed Jan. 24, 2008, hereby incorporated by reference in its entirety herein, discloses various lock mechanisms and clips that can be implemented to secure various components of the access device described herein.

As explained below in greater detail, the guidewire 44 is introduced through a hollow and tapered portion 62 of the needle hub 34, through the needle body 32, and into a punctured vessel. Advantageously, the tapered portion 62 can guide the guidewire 44 toward the bore of the needle 22. Further, in some embodiments this tapered portion 62 can provide a female luer connection. The guidewire 44 allows the healthcare provider to guide the dilator 24 and sheath 26 into the vessel.

Figure 2F:
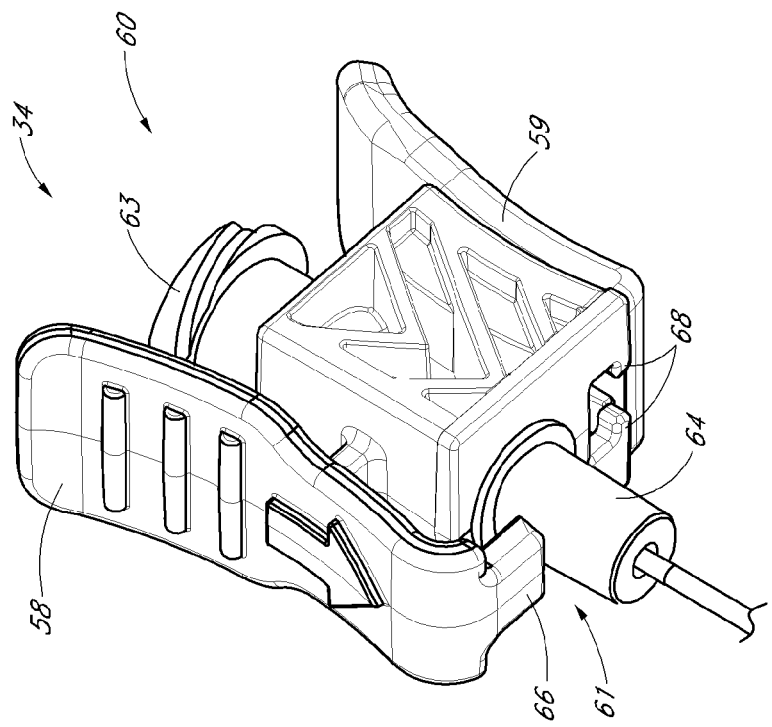
FIG. 2F is an enlarged perspective view of a needle hub of the needle of FIG. 2A.
Figure 2E:
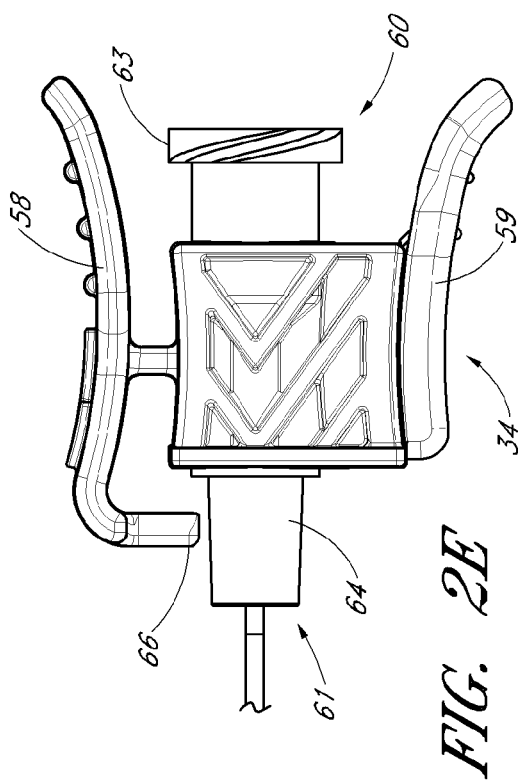
FIG. 2E is an enlarged side view of a needle hub of the needle of FIG. 2A.
Figure 2G:
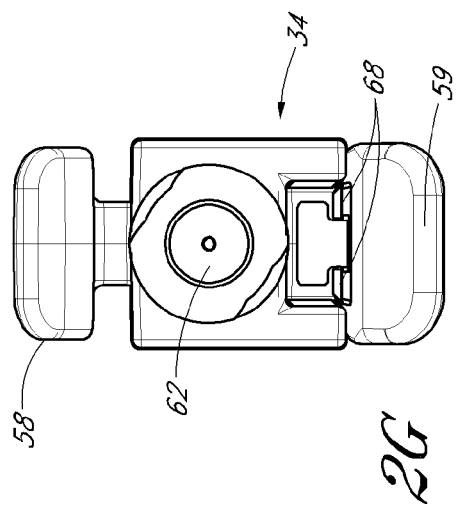
FIG. 2G is an enlarged proximal end view of the needle hub of the needle of FIG. 2A.

Referring to FIGS. 2C, 2F and 2G, the needle hub 34 may also comprise two tangs 68 that allow the needle hub 34 to slide along the track 30 between the first position 121 and the second position 123 (FIG. 6A). While in the preferred embodiment the two tangs 68 of the needle hub 34 are engaged with the track 30 between the first position 121 and the second position 123, in other embodiments the needle hub 34 is only engaged with the track 30 over a portion of the length of the track 30 between the first position 121 and the second position 123. The sliding interconnection between the track 30 and the needle hub 34 also can be accomplished using other cooperating structures (e.g., a corresponding pin and tail of a dovetail connection).

The needle 22 can comprise any of a variety of materials known in the art. In some embodiments, one or more portions of needle 22 can comprise a material, or can comprise a treatment or coating of a material to provide additional functionality to needle 22. For example, needle 22 can comprise one or more portions comprising materials with certain optical properties to facilitate the use of access device 20. PCT International Patent Application No. PCT/US2011/024097, filed Feb. 8, 2011, previously incorporated by reference in its entirety herein, discloses embodiments of a needle that include an echogenic portion and a contrast portion, either or both of which can be implemented with the needle or other components of the access device embodiments described herein.

Figure 3A:
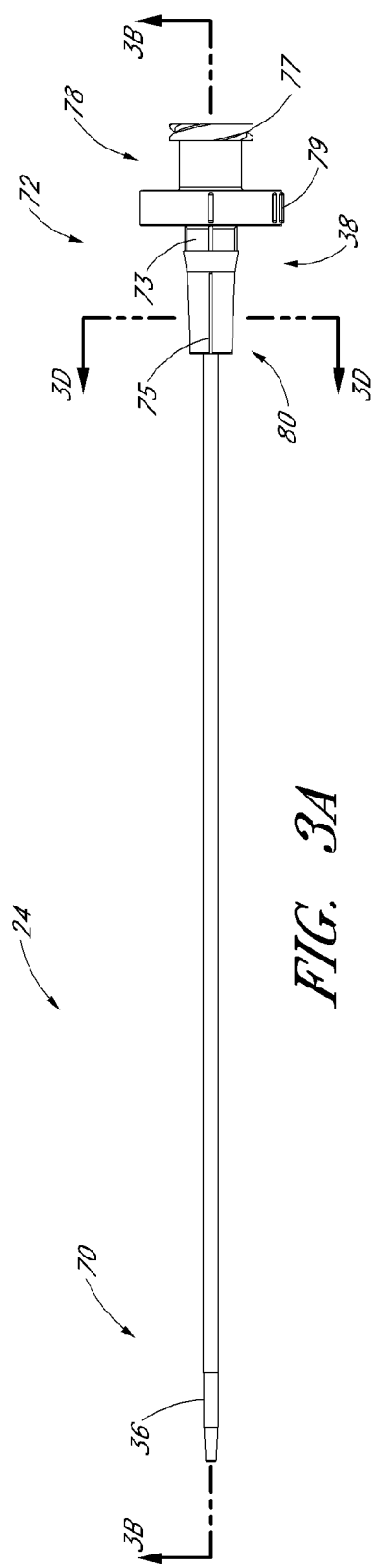
FIG. 3A is a plan view of the dilator from FIG. 1A.
Figure 3B:
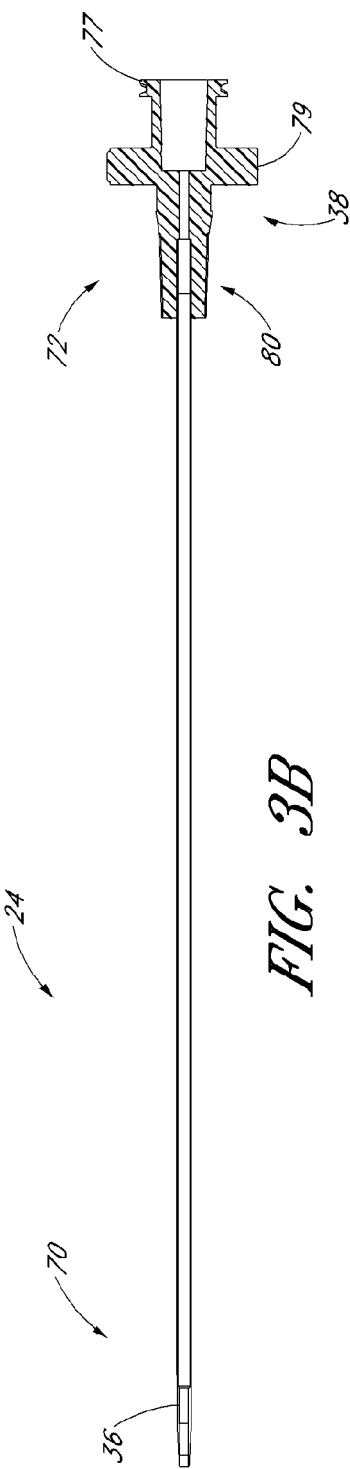
FIG. 3B is a cross-sectional view taken along the lines 3B-3B in FIG. 3A.

FIG. 3A is a plan view of the dilator 24 of the embodiment depicted in FIG. 1A. FIG. 3B is a cross-sectional view of the dilator 24 of the embodiment depicted in FIG. 3A, taken along line 3B-3B. As shown in FIGS. 3A and 3B, the illustrated dilator 24 comprises a dilator shaft 36, a dilator hub 38, a distal region 70, and a proximal region 72.

The dilator hub 38 may include locking structures to secure the dilator hub 38 to another portion of access device 20. Each locking structure may be a luer-type, thread-type, latch-type, other types of connections, or a combination thereof. In the illustrated embodiment, the dilator hub 38 comprises a first luer connection 78, a second luer connection 80, a lip 77, and a base 79. The first luer connection 78 is configured to engage with the needle hub 34 on the needle 22 illustrated in FIGS. 2A-2E (see also FIG. 7B). The second luer connection 80 is disposed distal to the first luer connection 78. In some embodiments, the second luer connection 80 (e.g., a male luer slip connector) can be configured to engage with the sheath hub 42 (e.g., a female luer slip connector) on the sheath 26 illustrated in FIGS. 1A-1B (see also FIG. 7B). It will be understood that orientation of the male-female lure slip connectors on these components can be reversed, and/or that additional or alternative locking structure can be implemented, such as latch element 66 (FIGS. 2E-2F; 7B) or the other latching and locking structures described herein.

For embodiments that have a channel formed between the needle and dilator 24, optical properties such as the color of the needle 22 and/or the dilator 24 may be selected to enhance the contrast between the blood or other fluid and the needle 22 and/or dilator 24. During blood flash, for example, and as described further herein, blood is observed flowing between the dilator 24 and the needle 22 to confirm proper placement of the needle in a blood vessel. To increase the visibility of the fluid as the fluid flows between the needle 22 and dilator 24, the dilator 24 is preferably manufactured from a clear or at least somewhat transparent material with the needle 22 having a color that contrasts with the color of the fluid. For example, the needle 22 may have a white color to enhance its contrast with red blood. Other colors of needle 22 could be employed depending on the color of the fluid and the degree of contrast desired. Further, in some embodiments only a portion of the needle in the region of the blood flash can have the contrasting color with the remainder having a different color.

Figure 3C:
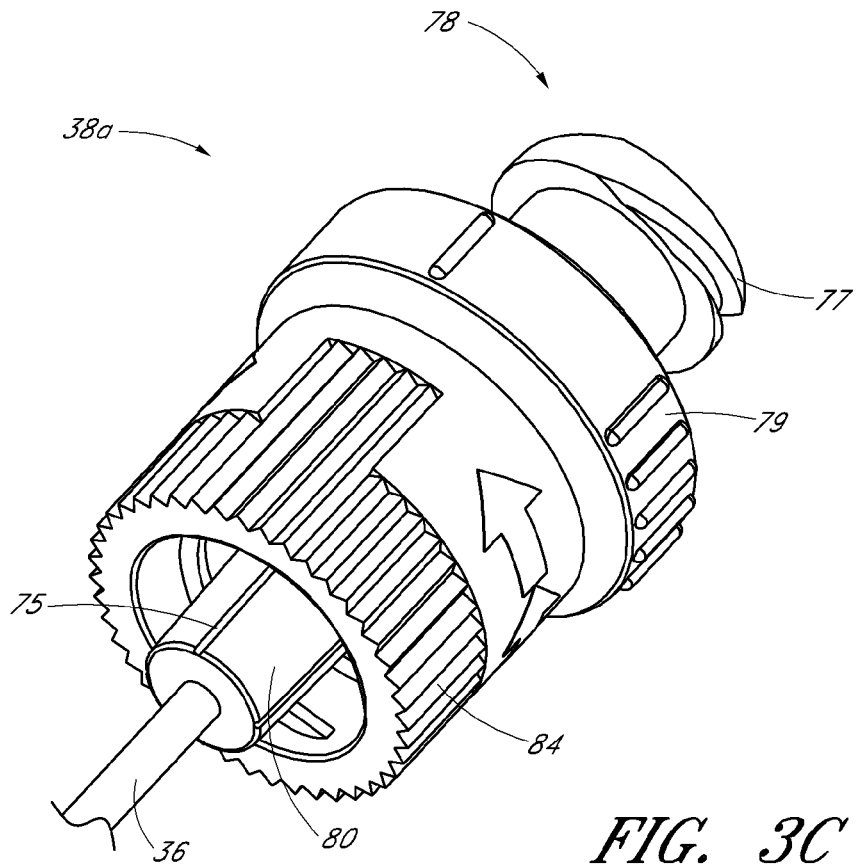
FIG. 3C is a perspective view of another embodiment of the dilator hub that includes a locking spin nut configured to secure to a sheath that has a corresponding screw thread.
Figure 3D:
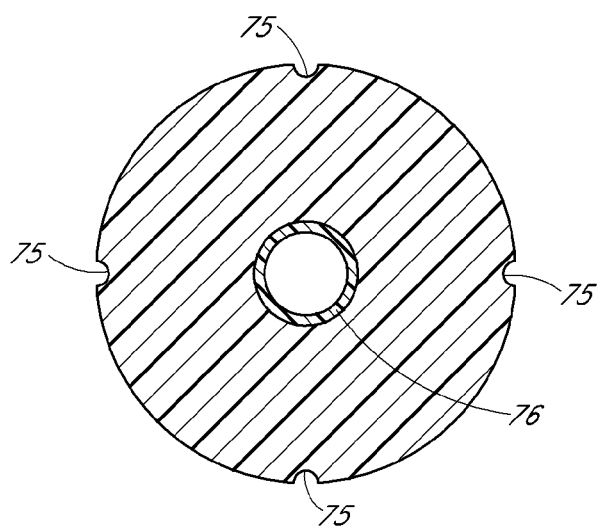
FIG. 3D is a cross-sectional view taken along the lines 3D-3D in FIG. 3A and shows the grooves equally spaced about the circumference of the luer surface.
Figure 3E:
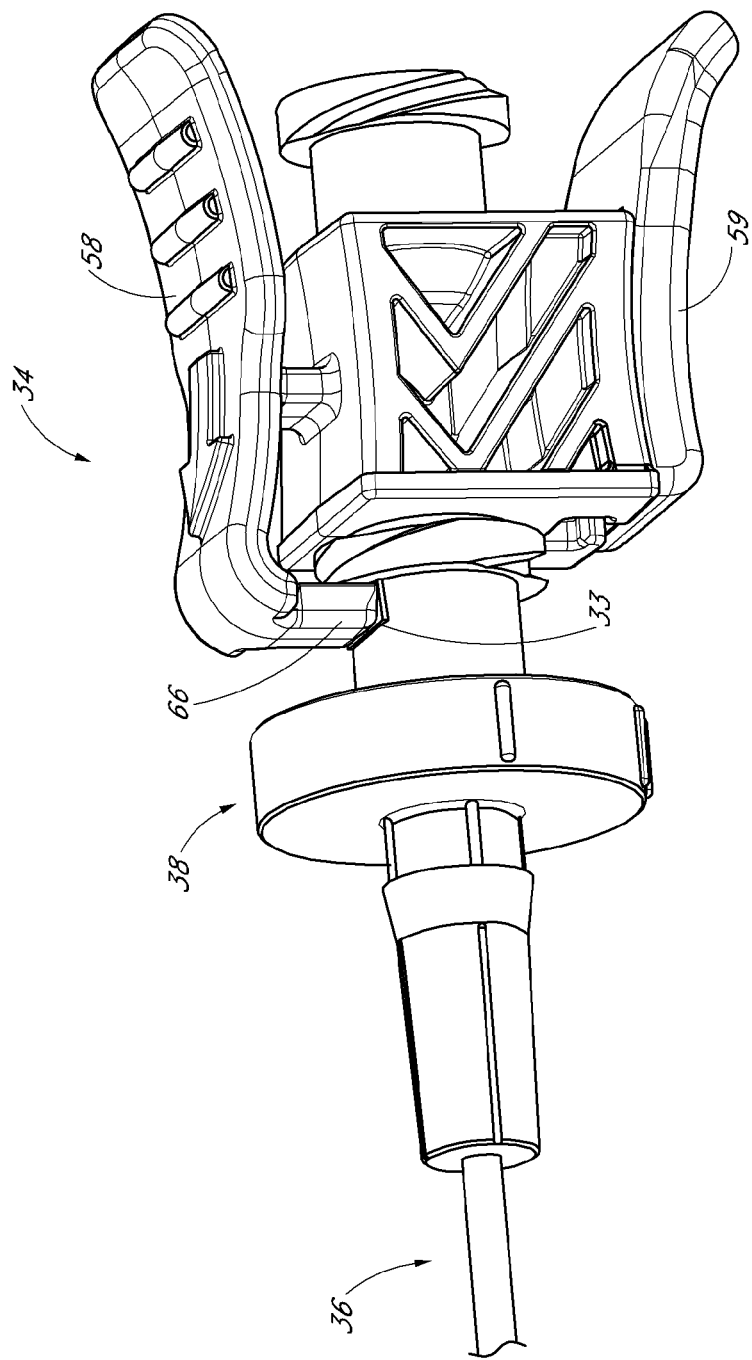
FIG. 3E is a perspective view of another embodiment of the dilator hub that includes a flat configured to engage with a latch element.

FIG. 3C is an enlarged perspective view of another embodiment of a dilator hub 38A. The dilator hub 38A is similar to the dilator hub 38 illustrated in FIG. 3A except that the dilator hub 38A further includes a spin nut or collar 84. The proximal end of the spin nut 84 rotates about an annular groove 73 in the dilator hub 38 (see, e.g., FIG. 3A). Once disposed within the annular groove 73, the spin nut 84 is inhibited from moving in the distal direction but is free to rotate about the dilator hub 38A. The spin nut 84 can have an interengaging element that locks to a corresponding interengaging element on the sheath 26. In the illustrated embodiment, the spin nut 84 includes an internal thread which engages with an external thread on the sheath hub 42 on the sheath 26 illustrated in FIG. 1A.

In some embodiments, the dilator shaft 36 may be configured with one or more fenestrations and/or channels to form a blood flash chamber disposed between a portion of a dilator and a sheath. The dilator shaft 36 can comprise one or more vents, such as grooves 75 (FIGS. 3A, 3D), to provide venting during blood flash. Examples of such a dilator shaft with one or more fenestrations, channels, and/or vents that can be implemented with elements described herein, are disclosed in PCT International Patent Application No. PCT/US2011/024097, filed Feb. 8, 2011, previously incorporated by reference in its entirety herein.

Figures 4A, 4B, 4C:
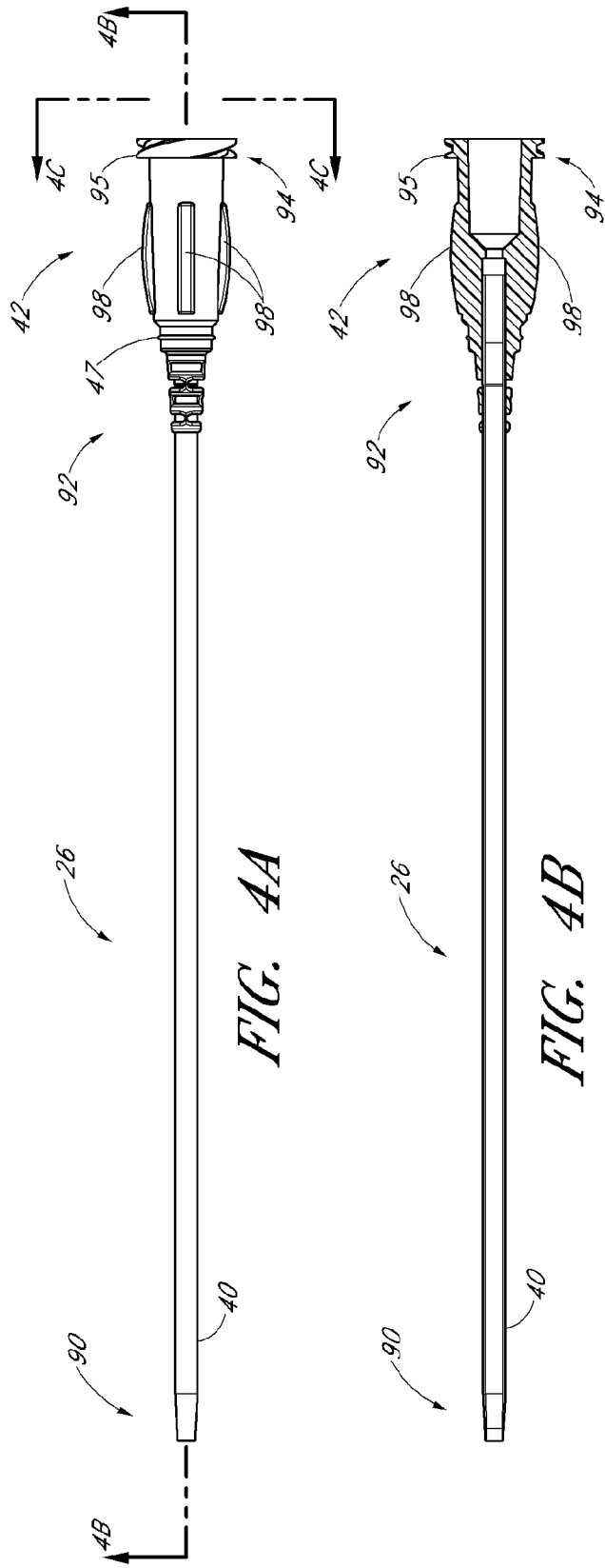
FIG. 4A is a plan view of the sheath from FIG. 1A and shows a sheath hub connected to a proximal end of a sheath.
FIG. 4B is a cross-sectional view of the sheath from FIG. 4A taken along the lines 4B-4B in FIG. 4A.
FIG. 4C is an enlarged end view of the sheath from FIG. 4A.
Figure 4D:
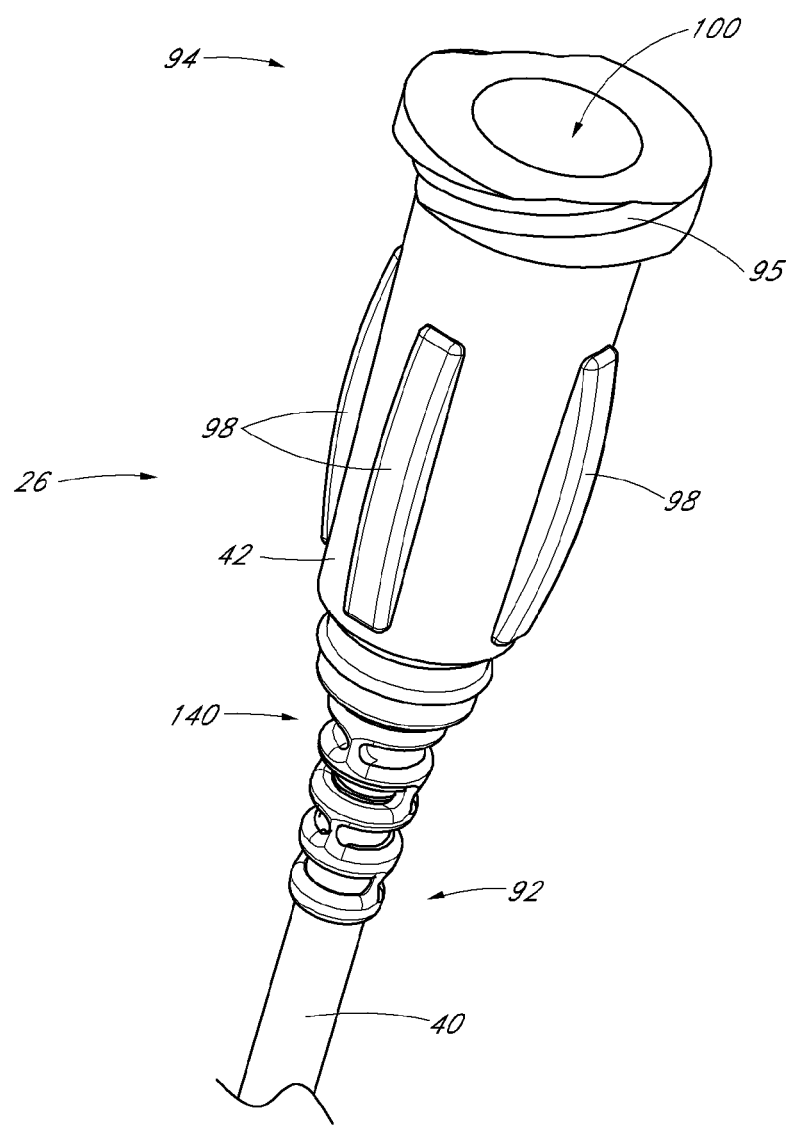
FIG. 4D is an enlarged perspective view of a proximal portion of the sheath from FIG. 4A.

FIG. 4A is a plan view of the sheath 26 of the embodiment depicted in FIG. 1A. FIG. 4B is a cross-sectional view of the sheath 26 of the embodiment depicted in FIG. 4A, taken along line 4B-4B. FIG. 4C is an enlarged proximal end view of the sheath 26 of FIG. 4A. FIG. 4D is an enlarged perspective view of the sheath hub 42 of the sheath 26 of FIG. 4A. As shown in FIGS. 4A-4D, the sheath 26 may comprise a sheath body 40, a sheath hub 42, a distal portion 90, and a proximal region 92. The sheath body 40 may be made partially or completely from clear, translucent, transparent, or semi-opaque material. The sheath body 40 can also include one or more radio opaque markers, such as, for example, barium sulfate stripes. In a preferred embodiment, the sheath includes two such radio opaque stripes disposed on diametrically opposite sides of the body 40.

The sheath body 40 may be a single piece sheath through which a catheter or other medical article (e.g., a guidewire) is inserted into the vessel. In such an embodiment, the sheath body 40 forms a conduit for insertion of the catheter or other medical article (e.g., a guidewire). In addition to providing a conduit, the sheath or a portion of the sheath can form a lumen that is in addition to the lumen(s) of the catheter. For example, an equivalent to a triple lumen catheter can be formed by inserting a dual lumen catheter through the sheath body 40 with the sheath body 40 itself forming a third lumen.

The sheath hub 42 may include an engagement or locking structure, such as a lock member 94 that mates or engages sheath hub 42 with a corresponding structure. For example, the lock member 94 can be a luer connection 94 which can be configured to engage with the second luer connection 80 of the dilator hub 38. In some embodiments, the sheath hub 42 can comprise a lip 95. The lip 95 can include threads or other attaching structure to allow the sheath hub 42 to attach to other medical articles with a corresponding locking feature. Locking member 94 and/or lip 95 can be configured to engage with spin nut or collar 84 disposed on dilator hub 38, described further herein and shown in FIG. 3C. In embodiments where both a luer connection 94 and a lip 95 are utilized, the sheath hub 42 can be more reliably attached by two independent forms of connection.

The sheath hub 42, preferably is designed so that the locking mechanism or second luer connection 80 of the dilator hub 38 (e.g., FIG. 3A) can enter the sheath hub 42 substantially unobstructed. However, in use, once the sheath hub 42 is placed at a desired location over the dilator shaft 36, the physician or healthcare provider can push, pull, or twist the sheath hub 42 and possibly disengage or engage the locking member 94 with a corresponding connector on another medical article. The locking member 94 is not limited to a luer connection, and can be, for example, a protruding bump, dent, press fit, snap fit, etc., that creates a mechanical fit so that the dilator hub 38 and the sheath hub 42 are releasably interlocked. Preferably, the locked position can be disengaged or engaged by pulling, squeezing, pushing or twisting the dilator hub 38 relative to the sheath hub 42.

The sheath hub 42 preferably comprises one or more surface features to allow the physician or healthcare provider to easily grasp or manipulate the sheath 26 and/or access device 20. For example, sheath hub 42 can include flatted portions to form, for example, a squared grip. In the illustrated embodiment, the sheath hub 42 includes ridges 98 for grasping by a user.

Figure 4F:
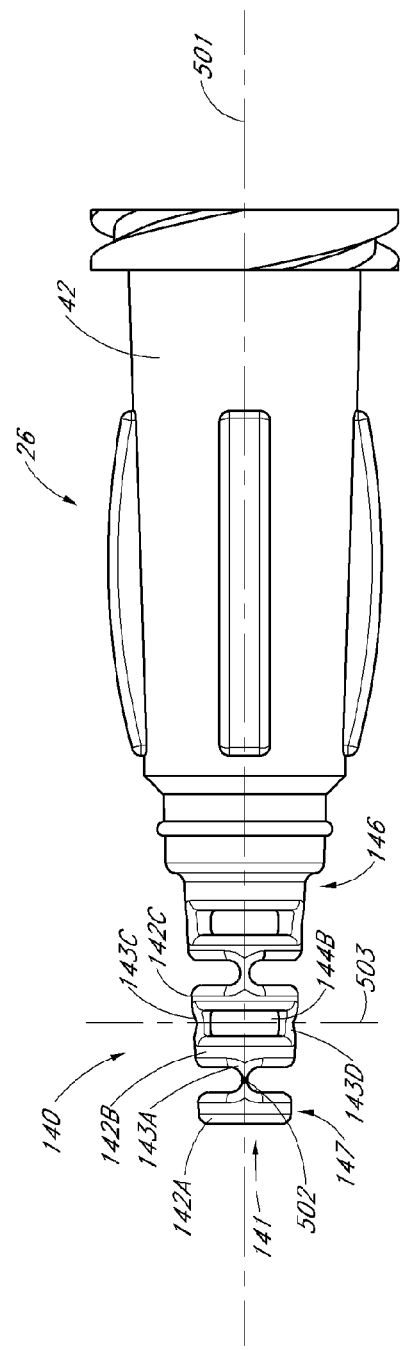
FIG. 4F is an enlarged side view of the proximal portion of the sheath from FIG. 4E.
Figure 4G:
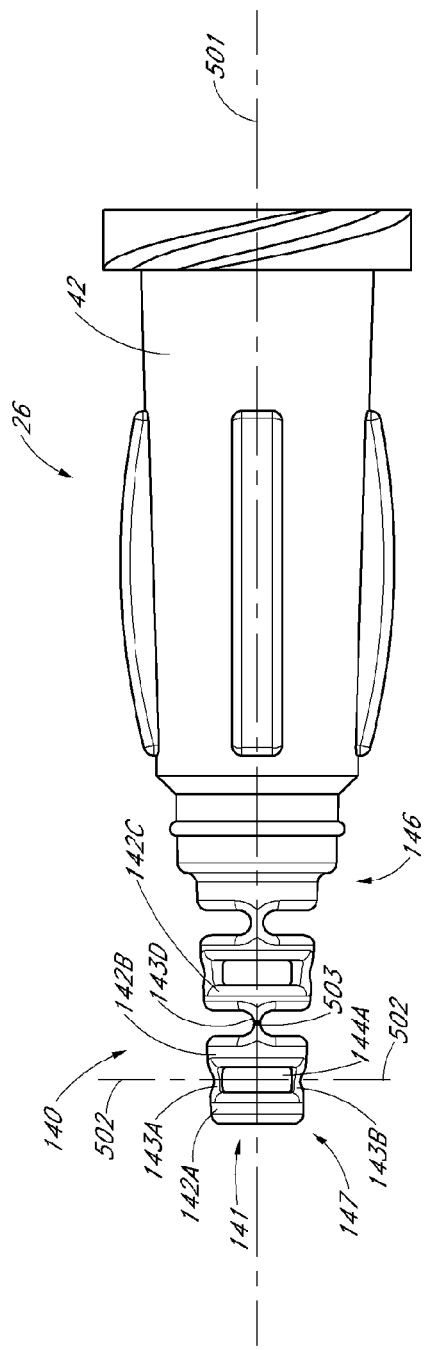
FIG. 4G is an enlarged plan view of the proximal portion of the sheath from FIG. 4E.

Referring to FIG. 4A, the sheath hub 42 can include an optional ridge 47, toward a distal end of the hub 42, to facilitate gripping of the hub 42. Ridge 47 can also receive and secure a cylindrical cover, as described further below (FIGS. 4J-4L).

FIG. 4E is an enlarged, partial perspective view of the sheath 26 from FIG. 4A, with the sheath body 40 not shown for clarity. FIGS. 4F and 4G are partial side and plan views, respectively, of the sheath 26 from FIG. 4E.

During or after the insertion of sheath 26 into a patient, sheath body 40 can overflex, kink, and/or permanently deform, which can reduce or inhibit the functionality of access device 20. Sheath body 40 can be susceptible to such kinking or permanent deformation, for example, at the interface between sheath body 40 and the sheath hub 42, or at portions upstream or downstream of the interface between sheath body 40 and the sheath hub 42. A kink or permanent deformation can inhibit the flow of fluid, such as blood or medicine, through sheath body 40. Additionally, if access device 20 is used, for example, for IV lines, PICC lines, and other higher pressure applications, the proximal end of sheath body 40 can move erratically in a "whipping" motion as the pressurized fluid flows through sheath 26. To reduce the likelihood of such kinking or permanent deformation within sheath body 40, and/or to reduce the likelihood of such whipping during the deployment of access device 20, in some embodiments, sheath 26 can include various materials and an optional relief element that can provide support to sheath 26. In some embodiments, bending forces within the device can be transferred to a kink-resistant relief element.

FIGS. 4D-4G illustrate an embodiment of an optional relief element 140 implemented with sheath 26. Relief element 140 can extend from the sheath hub 42 (e.g., a distal portion of the sheath hub 42). Relief element 140 can be disposed about proximal portion 92 of the sheath body 40, to provide support to the proximal portion 92 of the sheath body 40 when the proximal portion 92 flexes with respect to the sheath hub 42.

Relief element 140 can include a channel 141 through which sheath body 40 can at least partially extend through. Channel 141 can be sized to maintain a clearance fit, or preferably, a close or interference fit with sheath body 40, to provide the aforementioned support to proximal portion 92. Relief element 140 is shown with at least a portion completely encircling or enclosing a portion of sheath body 40 for illustrative purposes only. In some embodiments, relief element 140 comprises an arc-like or crescent-shaped axial cross section that does not completely surround sheath body 40, while still providing the aforementioned support to sheath body 40.

Relief element 140 can include a variety of shapes and structures to provide additional support to sheath body 40 while still providing some flexibility thereto. For example, relief element 140 can include a substantially hollow elongated member, comprising an approximately rectangular or cylindrical tubular shape, configured with a wall thickness and material that provide some support and flexibility. Relief element 140 can be configured with a substantially continuous or unbroken surface, or can include gaps, apertures, recessions, or other structure extending partially or completely through its surface to provide additional flexibility. Relief element 140 can include various support structures partially or completely surrounding channel 141, such as circumferential or longitudinal (axial) ribs, struts, and the like.

Referring to FIGS. 4D-4G, relief element 140 can include a plurality of ribs 142 spaced along and/or around (e.g., partially or completely around) channel 141. Ribs 142 can extend along a portion or all of the length or perimeter (e.g., circumference) of relief element 140 (channel 141). The plurality of ribs 142 can be spaced axially or circumferentially along a portion or all of the length or circumference of relief element 140 (channel 141). In the illustrated embodiment, ribs 142 extend circumferentially around channel 141, and are spaced axially with respect to channel 141 to form relief element 140. Adjacent ribs within the plurality of ribs 142 can be spaced at irregular intervals, and are shown being spaced at regular intervals for illustrative purposes.

Relief element 140 can include a plurality of struts 143 connected to ribs 142, to provide additional support to ribs 142. In the illustrated embodiment, struts 142 are circumferentially spaced around channel 141, and extend axially between adjacent ribs 142. However, in embodiments including ribs that extend axially and are spaced circumferentially with respect to each other, the struts can extend circumferentially and can be spaced axially between adjacent ribs. Additionally, although two struts 143 are shown extending between any two adjacent ribs 142, the relief element 140 is not limited as such, and one or more struts can extend between any two adjacent ribs. Additionally, the struts and/or ribs, while shown extending axially and circumferentially, can be oriented at any of a variety of angles with respect to each other and/or with respect to channel 141 while forming relief element 140. For example, one or more ribs and/or struts can extend both circumferentially and longitudinally around channel 141, to form a spiral or helical shape. Further, as shown, the struts 143 can be provided in an alternating, discontinuous pattern, which can further enhance resistance to kinking.

The cross-sectional shape of relief element 140 (and channel 141) can be substantially constant, or can vary along its longitudinal axis. For example, the longitudinal cross-section of the sidewalls of relief element 140 can substantially match the exterior of the sheath body 40, which may be constant or varying. For example, the sidewalls of the relief element may then be greater at a proximal portion 146 than a distal portion 147 of relief element 140. Such an embodiment allows proximal portion 146 of relief element 140 to provide greater support to the proximal portion 92 of sheath body 40, while allowing greater flexibility to sheath body 40 at the interface between distal portion 147 of relief element 140. As such, relief element 140 can comprise a substantially cylindrical or a substantially frustro-conical shape.

Ribs 142 and/or struts 143 can be supported around channel 141 to form relief element 140 in a variety of ways. For example, in the aforementioned embodiments shown in FIGS. 4D-4G, ribs 142 and struts 143 can be self supporting, to form one or more openings, cells, apertures or gaps 144 extending between grouped adjacent ribs 142 and struts 143. Gaps 144 can provide flexibility to relief element 140, while ribs 142 and struts 143 provide support.

Referring to FIGS. 4F and 4G, relief element 140 can include one or more struts that are circumferentially offset from each other. For example, relief element 140 can include a first adjacent pair of ribs, such as ribs 142A and 142B, and a second adjacent pair of ribs, such as ribs 142B and 142C. As such, the first adjacent pair of ribs and the second adjacent pair of ribs can include a common rib 142B. A first set of struts 143A and 143B can extend between the first adjacent pair of ribs 142A and 142B. Struts 143A and 143B can be circumferentially offset from each other with respect to an axis 501 extending longitudinally through sheath hub 42. Struts 143A and 143B can be circumferentially offset by any of a number of angles, although here, struts 143A and 143B are offset by approximately 180 degrees, and are thus approximately opposed to each other and collinear on a transverse axis 502 extending through relief element 140.

Struts 143A and 143B can be approximately collinear to allow ribs 142A and 142B to flex with respect to each other about axis 502 (e.g., within gap 144A), without kinking relief element 142.

Similarly, a second set of struts 143C and 143D can extend between the second adjacent pair of ribs 142B and 142C. Struts 143C and 143D can be circumferentially offset from each other with respect to axis 501. Struts 143C and 143D can be circumferentially offset with respect to each other and with respect to struts 143A and 143B by any of a number of angles. Here, struts 143C and 143D are offset by approximately 180 degrees with respect to each other, and are thus approximately opposed to each other and collinear on a transverse axis 503 extending through relief element 140. Struts 143C and 143D can be approximately collinear to allow ribs 142B and 142C to flex with respect to each other about axis 503 (e.g., within gap 144B), without kinking relief element 142.

Additionally, struts 143C and 143D can be circumferentially offset with respect to struts 143A and 143B about axis 501, at any of a number of different angles (e.g., 90 degrees). Thus, axes 502 and 503 can be circumferentially offset from each other, to allow flexing of various sets of adjacent ribs (e.g., ribs 142A/142B and 142B/142C) in various directions. These embodiments of relief element 140 can both provide support and flexibility to relief element 140 and/or a sheath body, while reducing kinking thereof. For example, when struts 143A and 143B flex about axis 502, struts 143C and 143D provide axial support to relief element 140. Conversely, when struts 143C and 143D flex about axis 503, struts 143A and 143B provide axial support to relief element 140. It will be understood that the first and second adjacent pair of ribs as described herein can be configured with or without a common rib, (such as rib 142B). For example, the first adjacent pair of ribs can include ribs 142A and 142B, and the second pair of adjacent ribs can include rib 142C and a fourth rib. In such an embodiment, one or more of the aforementioned struts can be configured to extend between ribs 142A and 142B, 142B and 142C, and/or 142C and the fourth rib, in any of the aforementioned strut orientations.

The embodiments of the relief elements shown in FIGS. 4D-4G can be configured without additional support structure (as shown). However, in some embodiments, some, most, all, or at least a portion of the relief elements described herein, such as ribs 142 and/or struts 143 of relief element 140 can be attached to, surrounded or covered by, and/or supported by an additional structure, such as one or more optional tubular sleeves, covers, or similar structure. Such sleeves, covers, and the like, can be integrally formed with (e.g., and can comprise a portion of) the relief element, or can be separately formed (e.g., a removable sleeve) from the relief element.

Figure 4I:
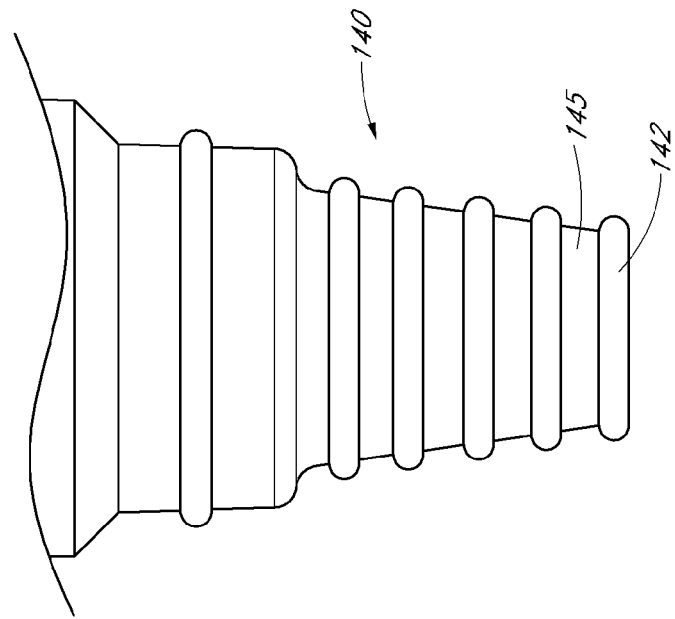
FIG. 4I is an enlarged plan view of another embodiment of a sheath including a relief element.
Figure 4H:
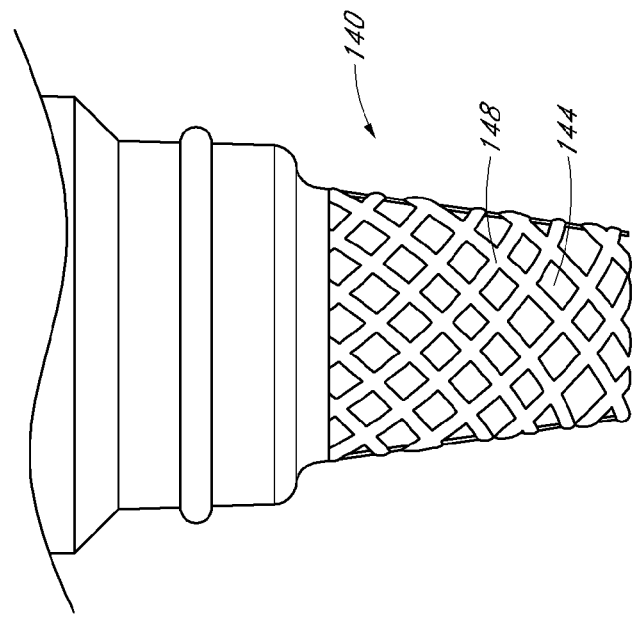
FIG. 4H is an enlarged plan view of another embodiment of a sheath including a relief element.
Figure 4J:
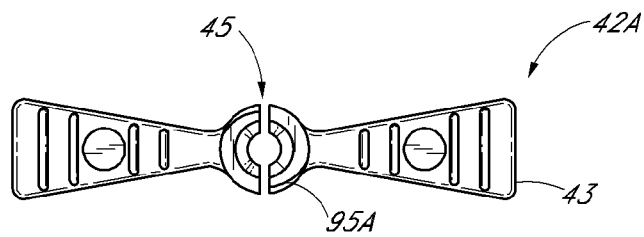
FIG. 4J is a proximal end view of another embodiment of a sheath.
Figure 4K:
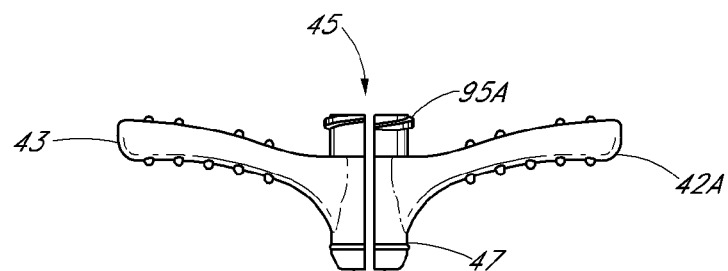
FIG. 4K is a plan view of the sheath of FIG. 4J.
Figure 4L:
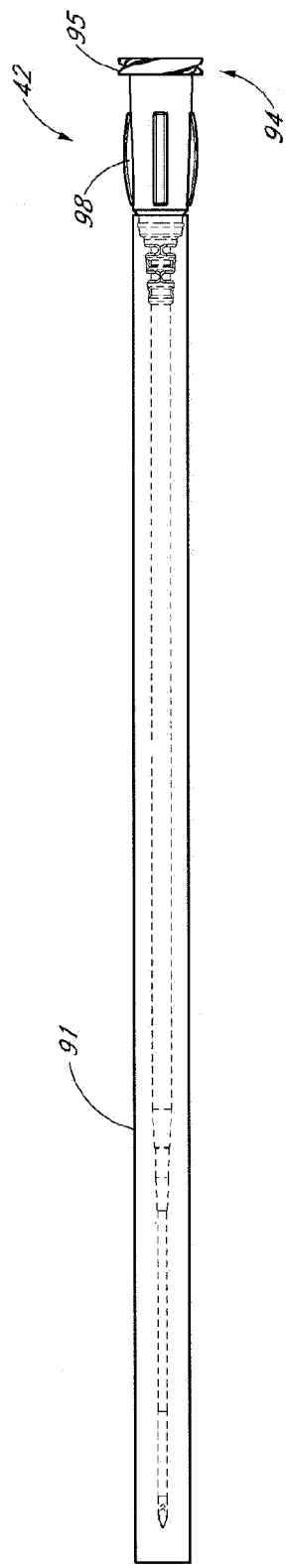
FIG. 4L is a side view of a cover for the sheath of FIG. 4A.

FIG. 4I illustrates an embodiment of relief element 140 that includes a sleeve 145 on which a plurality of ribs 142 and/or struts 143 are attached and/or supported. In some embodiments, such as that shown in FIG. 4H, relief element 140 can comprise a screened or mesh-like structure 148 with a plurality of apertures 144 extending therethrough, formed by generally continuous ribs and struts, without the aforementioned alternating features.

In some embodiments, the optional cylindrical or tubular covers or sleeves described herein can be configured to cover some, most, all, or at least a portion of relief element 140, or other portions of the sheaths described herein. For example, a tubular cover or sleeve may be employed to prevent blood or other fluid from entering regions within or between ribs 142, apertures 144, and/or struts 143. In some embodiments, the wall of the tubular cover or sleeve can be sufficiently thin and/or the cover or sleeve can comprise a material with sufficient flexibility, to cover a portion of relief element 140 without significantly reducing the aforementioned flexibility of relief element 140. In some embodiments, the tubular cover or sleeve can include a material with a modulus of elasticity that is greater than the modulus of elasticity used for the remainder of relief element 140.

The tubular covers or sleeves described herein can be employed with an access device that does not include a relief element. The tubular covers or sleeves can be configured to cover other portions of the access devices described herein. In some embodiments, the tubular covers or sleeves can be configured to cover and extend over a portion of both the sheath body and sheath hub, and preferably, such that the transition between these two components is covered. Such embodiments can protect and prevent contamination at this transition between the sheath body and sheath hub.

In some embodiments, the tubular cover or sleeve can be coated with and/or include a material with medicinal or therapeutic properties, such as an anti-bacterial material, anti-microbial material, and the like. For example, the tubular cover or sleeve can comprise silver and/or a silver compound for its anti-bacterial properties. In some embodiments, the tubular cover or sleeve can comprise a thermoplastic elastomer or other suitable material, for example, that simulate and/or provide the flexibility and durability of a natural material such as natural rubber, while providing longer life in various temperature environments. For example, the tubular cover or sleeve can comprise a mixture of ethylene-propylene-diene monomer copolymer (EPDM) and polypropylene. In some embodiments, the tubular cover or sleeve can comprise an EPDM and polypropylene mix of approximately 60 parts EPDM with 40 parts polypropylene, such as Santoprene®, manufactured by Exxon Mobil.

Figure 4M:
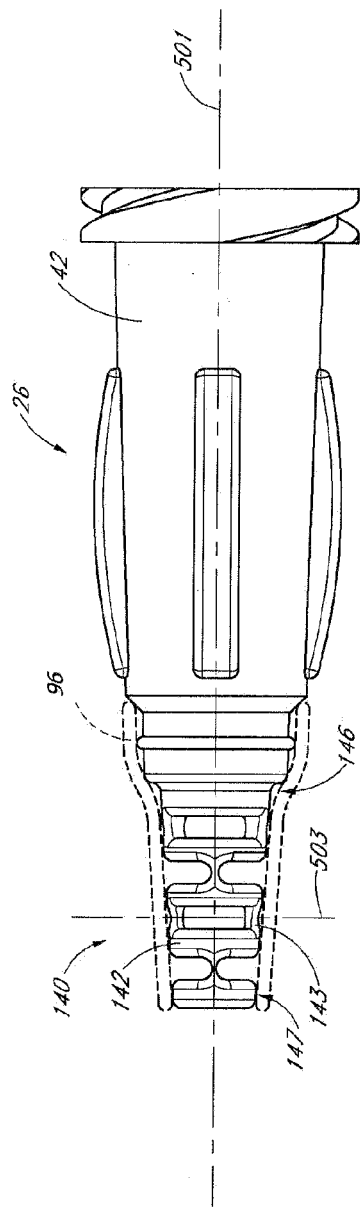
FIG. 4M is a side view of a cover for a portion of a sheath.

FIG. 4M illustrates an embodiment of a cover or sleeve 96. Cover 96 can include any of the features described generally herein with respect to the covers and sleeves. Preferably, sleeve 96 is configured to conform to a portion or substantially the entirety of relief element 140 (e.g., its outer surface) to prevent the aforementioned fluid from entering the regions between ribs 142, apertures 144, and/or struts 143. In some embodiments, cover 96 can provide support when relief element 140 is bent. Although the depicted sleeve 96 is depicted as covering only the relief element, in other embodiments the sleeve 96 can be modified to cover a greater portion of the device, such as other ridges, apertures, or other features on the sheath hub 42. In some embodiments, the sleeve 96 can extend past the distal end of the relief element, to cover a portion or substantially the entirety of the sheath body 40. In some embodiments, the sleeve 96 can extend past the proximal end of the relief element, to a portion of substantially the entirety of the sheath hub 42. Additionally, the cover 96 can be configured to cover portions or substantially the entirety of other embodiments of the relief elements described herein, and is not limited to use only with the relief element 140 shown in FIG. 4M. Additionally, as described above, the cover 96 can be employed to cover other portions of the sheaths or other portions of the access devices that include or do not include the relief element 40. The cover 96 can be configured to cover or extend over a portion of the sheath hub 42 and sheath body 40, in embodiments with or without the relief element 40. In some embodiments, the cover 96 can be configured to cover at least a transition between the sheath hub 42 and sheath body 40, such as a transition 97 shown in FIG. 4D, with or without the relief element 40.

Relief element 140 can comprise any of the materials described herein for sheath 40, and can be integrally formed with or separate from sheath body 40 and/or sheath hub 42.

Further, in some embodiments the sheath 26 can be a splittable sheath. For example, it may be advantageous to remove a portion or the entire sheath body 40 depending on the type of catheter or medical article that is to be inserted into the vessel after employing the access device 20. For example, after the catheter or other medical article is inserted into the vessel, a portion of the sheath body 40 can be separated or peeled-away and removed to reduce clutter at the access site. A peel-away sheath can include perforations, serrations, skives, or other structures, or include other materials (e.g., PTFE with bismuth) to allow the physician or healthcare provider to remove easily a portion or the entire sheath body 40.

In some embodiments, the sheath hub 42 may comprise radially extending wings or handle structures to allow for easy release and removal of the sheath body 40 from other parts of the access device 20. In some applications, the wings are sized to provide the healthcare provider with leverage for breaking apart the sheath hub 42. The sheath hub 42 and/or the sheath body 40 may comprise two or more portions (e.g. halves) connected by a thin (e.g., frangible) membrane. The membrane can be sized to hold the two or more portions of the sheath hub 42 and/or sheath body 40 together until the healthcare provider decides to remove the sheath hub 42 and/or sheath body 40 from the access device. The healthcare provider manipulates the wings to break the membrane and sever one or more portions of the sheath hub 42 into separate or partially separated pieces.

An example of such a sheath is depicted in FIGS. 4J and 4K, with some similarities to the previous sheaths described herein. Sheath 26A can be implemented with other components of access device 20. In the illustrated embodiment, the sheath 26A is a splittable or severable sheath. As depicted, the sheath hub 42A can have two or more tabs 43 that can be gripped by a user. Tabs 43 can have any of a number of different shapes and/or surface features to facilitate them being gripped, and are not limited to the substantially T-shape shown. Tabs 43 are separable, to allow the splittable sheath 40A to separate along one or more split lines, such as a predetermined split or separation line 45. The split line 45 can extend through either or both the sheath hub 42A and the sheath body 40A. The split line(s) can extend generally parallel to one or more longitudinal axes defined by the sheath body 40A and/or sheath hub 42A, but in some embodiments, the split line(s) can extend substantially non-parallel. As illustrated, splitting the sheath 26A along the split line 45 can separate the sheath 26A into two or more symmetrical or asymmetrical portions (e.g., halves). The sheath 26A can include similar additional features described herein for sheath 26. In some embodiments, sheath 26A can include similar features that are also configured to be separable into one or more portions along split line 45. For example, sheath 26A can have a separable lip 95A, allowing engagement of sheath 26A with other elements described above, such as the dilator 24, while allowing separation along split line 45. Additional embodiments of a splittable sheath body and/or hub that can be employed with sheath 26A are shown and described, for example, in FIGS. 23A-23B, and the corresponding supporting text (e.g., paragraphs [0223]-[0227]), of PCT International Patent Application No. PCT/US2010/034609, filed May 12, 2010, hereby incorporated by reference in its entirety herein.

The sheath hub 42A can additionally include the ridge 47 toward a distal end of the hub. The ridge 47 can facilitate gripping of the hub 42A. In some embodiments, the ridge 47 can receive a tubular or cylindrical cover that can extend over portions of the sheath, dilator, and needle (e.g., to protect the distal, tips, or other portions thereof), and engage with (e.g., press onto) the ridge 47. Ridge 47 can hold the cover in place through any of a number of engagement methods, such as a press or snap fit. An embodiment of a cover 91 that can be used to cover one or more portions of sheath 26A, needle 22, and/or dilator 24 is shown in FIG. 4L. It will be understood that cover 91 and ridge 47 are optional, are not limited to use with the splittable sheath 42A of FIGS. 4J and 4K, and can be implemented in any of the other embodiments of sheaths described herein, such as those shown in FIGS. 4A-4I, 4M. Additionally, cover 91 does not require ridge 47, and can be secured (e.g., releasably secured) using a number of different attachment structures. In some embodiments, cover 91 can be configured to cover a portion of needle 22, such the tip of needle 22. For example, cover 91 can cover the tip of needle 22 while access device 10 is packaged and shipped, and removed and discarded prior to use of access device 10.

FIG. 5A is a perspective view of the guidewire section 28 of the embodiment depicted in FIG. 1A. FIG. 5B is a plan view of the guidewire section 28 depicted in FIG. 5A, which preferably includes the guidewire hub 46. The guidewire hub 46 can comprise one or more surface features to allow the physician or healthcare provider to easily grasp or manipulate the guidewire hub 46 and/or access device 20. In the illustrated embodiment, the guidewire hub 46 comprises one or more ridges 110. In a pre-loaded state, the guidewire hub 46 can engage with a locking mechanism 130 on the track 30 when the guidewire hub 46 is in a third position 125, described further herein (example third position illustrated in FIG. 6A).

Figure 6B:
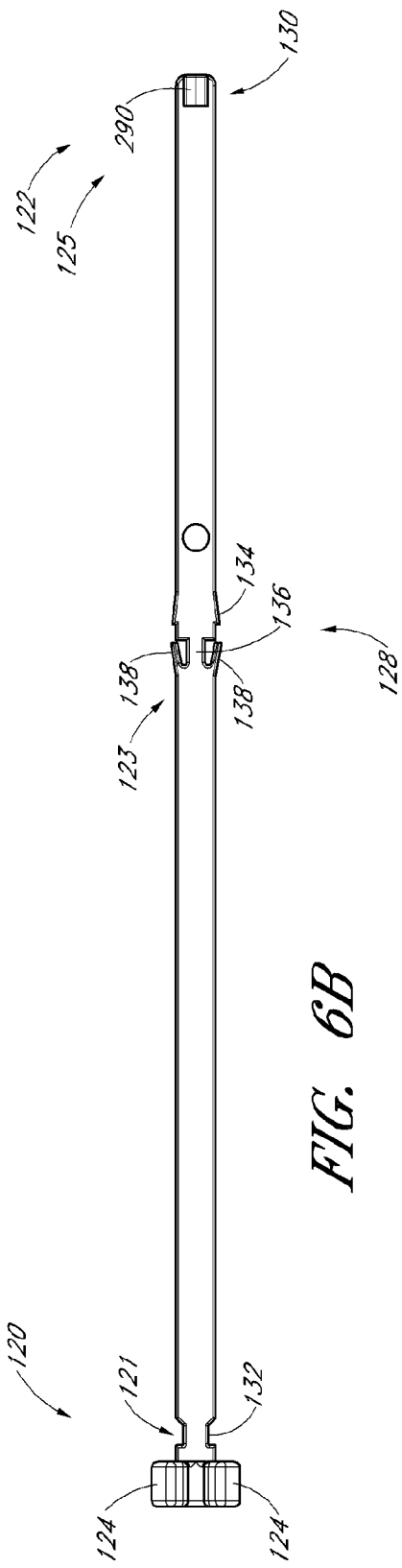
FIG. 6B is a plan view of the track in FIG. 6A and shows a locking mechanism for locking the needle relative to the dilator.
Figure 6C:
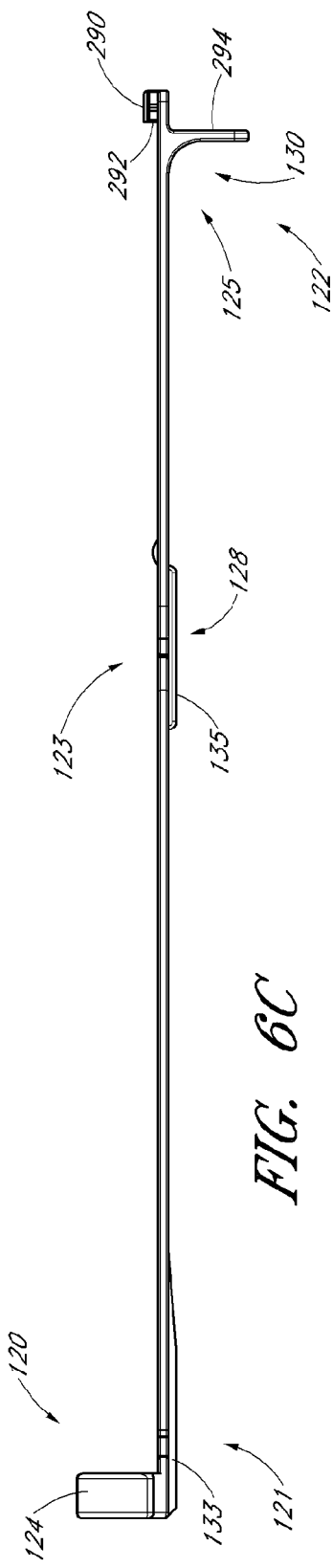
FIG. 6C is a side view of the track in FIG. 6B.
Figure 6D:
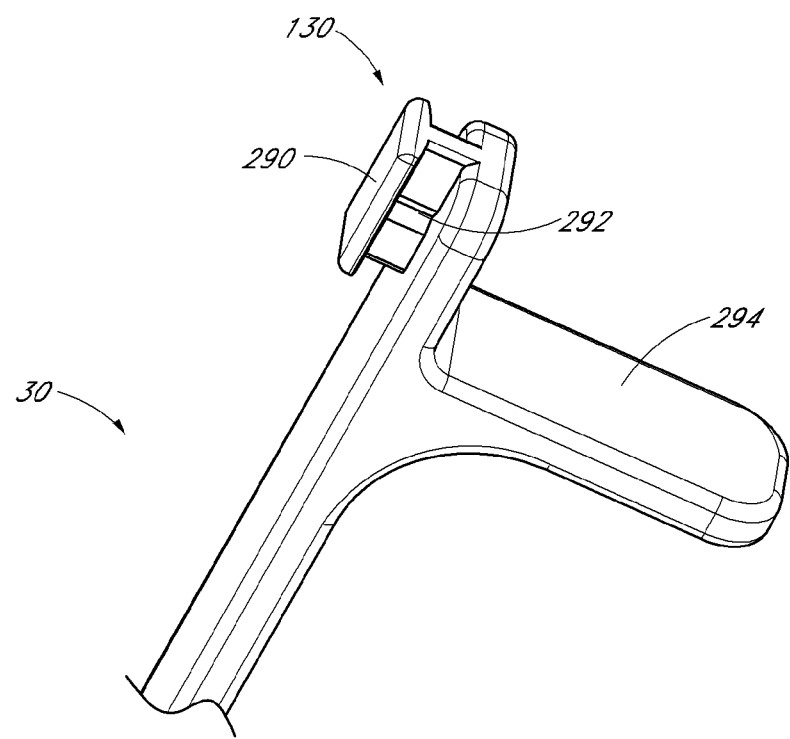
FIG. 6D an enlarged perspective view of the locking mechanism from FIG. 6B.

FIGS. 5C and 5D illustrate a perspective and bottom view, respectively, of an embodiment of guidewire hub 46. Guidewire hub 46 can have structure corresponding to a coupling section 290 on track 30 (FIGS. 6A-6D) to releasably connect hub 46 to track 30. As depicted, the guidewire hub 46 can include a receiving section 296 that can be in the form of a recess. The recess can have a T-shaped cross-section at a proximal end that can engage with the coupling section 290, as best depicted in FIG. 6D. Section 296 can comprise two tines 302 that terminate with latch projections 298, positioned further within the recess of the receiving section 296. Referring to FIGS. 5C, 5D and 6D, latch projections 298 on the guidewire hub 46 can be configured to receive the base of the coupling section 290 of the track 30. In some embodiments, coupling section 290 can comprise latch recesses 292 that can interact (e.g. engage) with projections 298 on the receiving section 296 to form a reversible snap-fit between the track 30 and the guidewire hub 46. In some embodiments, the tines 302 can include bending portions (configured with a thinner cross-sectional shape, or formed from a flexible material), that allow the tines 302 to flex (e.g., laterally), to facilitate the snap-fit. Further, the receiving section 296 can include an end portion or recess 300 in-line with the provided path provided for the coupling section 290 between the tines, such that when the latch recesses 292 and projections 298 interengage, a remaining portion of the coupling section 290 (e.g., an end portion) can also enter the end recess 300. Thus, the connection between the track 30 and hub 46 can be further stabilized.

In some embodiments, the guidewire 44 may form a close fit with the inside diameter of the needle body so as to provide a self-aspirating function when retracted. For example, an outside diameter of the guidewire 44 may be selected to form a close fit with the needle along the length of the guide wire or along only a portion of the guidewire 44.

In some embodiments, a section of the distal end of the guidewire can have a reduced diameter in comparison to other sections of the guidewire. The size and/or shape of such reduced diameter section can be selected to permit fluid to pass to the fenestration 56 in the needle body even when the guidewire has been advanced beyond the distal tip of the needle. The reduced diameter section of the guidewire does not need to be configured at the distal-most end of the guidewire, and can be positioned proximal to the tip or distal-most end of the guidewire.

The distal-most end of the guidewire may comprise a curved or rounded head to prevent puncturing tissue during insertion. In some embodiments, the guidewire can comprise a spring-like or other flexible, resilient member near the tip or distal head of the guidewire, to facilitate its insertion into a patient's internal lumen or cavity.

FIG. 6A is a perspective view of the track 30 of the embodiment depicted in FIG. 1A. FIG. 6B is a plan view of the track 30 illustrated in FIG. 6A. FIG. 6C is a side view of the track 30 illustrated in FIG. 6A. As shown in FIGS. 6A-6C, the track 30 in the illustrated embodiment comprises a distal portion 120, a proximal portion 122, a distal locking member 124 that connects the track to the dilator hub 38 (FIG. 3A), a locking mechanism 128 that inhibits further proximal and distal movement of the needle hub 34 once the needle hub 34 is slid from the first position 121 to the second position 123 along the track 30, and a locking mechanism 130 that allows the guidewire hub 46 to attach to the track 30 when the guidewire hub is in the pre-loaded state or third position 125. Preferably, the track is made of polycarbonate material; however, as explained below, other materials can be used.

The track 30 may further include a track section 132 of reduced width as shown most clearly in FIGS. 6A and 6B. The reduced width facilitates assembly of the needle hub to the track 30 (e.g., the engagement of tangs 68 (FIG. 2F) to track 30). The illustrated embodiment includes a reinforcement element, or rib 133 on the distal portion 120 of the track 30. The rib 133 provides additional structural reinforcement between the distal locking member 124 and the remainder of the track 30.

As illustrated in FIG. 1A, the distal locking member 124 connects to the dilator 24 and allows the track 30 to extend proximally from the dilator 24. For example, the locking member 124 can comprise two curved arms 124 that connect to the dilator hub 38 between the dilator hub lip 77 and the dilator hub base 79. The locking member 124 limits movement of the track 30 in a distal or proximal direction relative to the dilator hub 38 but allows the track 30 to rotate freely around the dilator hub 38.

As best shown in FIGS. 6A and 6B, the locking mechanism 128 is formed by varying the width of the track in the region of the second position 123. For example, the illustrated embodiment includes a track section 134 of increasing width in the distal direction, a track section 136 of reduced width distal to the track section 134 of increasing width, and two finger elements 138. The two finger elements 138 project from the distal end of the track section 136 toward the proximal end of the track 30 and flare away from the longitudinal axis of the track 30. Track 30 can also comprise a rib or support structure 135, similar to rib 133, that can span and reinforce locking mechanism 128.

FIG. 6D is an enlarged view of a portion of the embodiment depicted in FIG. 6B. As depicted, the third position 125 can include the releasable coupling or locking mechanism 130 that can engage with the guidewire hub 46 (e.g., FIGS. 5A-5D). The locking mechanism 130 is formed by a clip, clasp or other structure that engages with a portion of the guidewire hub or with a portion of the track 30 when the guidewire hub is in the third position. Some or all of the engagement structure may be part of the track 30, be part of the guidewire hub, or be split between the track 30 and guidewire hub.

The coupling mechanism 130 can include a coupling section 290 formed from a T-shaped projection extending from the track 30. The T-shaped projection can additionally include two latch recesses 292, on each side of its base, generally toward a distal end of the coupling section 290. Coupling section 290 and latch recesses 292 can engage with corresponding components on guidewire hub 46, such as receiving section 296 and projections 298, respectively, as described further above (FIGS. 5C and 5D).

In some embodiments, the track 30 can include a grip projection 294. The grip projection 294 can extend downward from the track 30, opposite from the coupling section 290. As depicted, the grip projection 294 can be generally circular, but other structures and shapes are possible. Grip projection 294 can include ridges or other surface features to assist in its grasp by a user. Advantageously, the grip projection 294 can allow an operator of the access device to hold the proximal end of the track 30 in a pistol-type grip. For example, a ring finger or middle finger can be positioned around the grip projection 294 to contact it on the distal side. The thumb of the same hand can then be placed on the proximal end of a guidewire hub 46 when hub 46 is coupled to track 30 in the third position 125. The thumb can then easily apply pressure to move the hub 46 off of the coupling section 290 and out of the third position 125. Further, similar grip projections can be applied to other elements, such as a needle. Applying a grip projection to the needle can, for example, allow a needle to be easily gripped and moved along a track as described herein In the illustrated embodiment, the locking mechanism between the needle hub and the dilator resides on the proximal side of the dilator hub. In other embodiments, however, the locking mechanism can be disposed at other locations as well. In some embodiments, the locking mechanism can comprise a stop or additional supporting structure to further support and/or control the movement of a hub or other component on track 30.

FIG. 7A is an enlarged plan view of the access device of the embodiment depicted in FIG. 1A pre-loaded with the guidewire. FIG. 7B is a side view of the embodiment depicted in FIG. 7A. FIG. 7C is a cross-sectional view of the embodiment depicted in FIG. 7A. FIG. 7D is a proximal end view of the access device 20 of FIG. 7B viewed along line 7D-7D. In this pre-loaded state, the guidewire hub 46 is locked to the track 30 when the guidewire hub 46 is located in a third position 125. In this position, the guidewire hub 46 can be secured to the track 30 with locking mechanism 130. In the depicted embodiment, the locking mechanism 130 can arrest unintended rotational and axial movement of the guidewire 44 at least in the proximal direction when the guidewire hub 46 is in the third position 125. Further, movement in the distal direction can be resisted until a user, such as a healthcare provider, disengages the guidewire hub 46 from the track 30 to allow distal movement of the guidewire through the access device 20. Notably, as discussed further herein, other elements can attach to the track 30 such as the dilator hub 38, and further elements can attach thereto. Thus, securement of the guidewire 40 to the track 30 can further arrest the guidewire to other elements of the access device 20.

In the preloaded-state illustrated in FIGS. 7A-7C, the needle hub 34 is locked to the dilator hub 38 when the needle hub 34 is in the first position 121. In embodiments with both needle and dilator fenestrations, in the locked position, the openings or fenestrations in the needle and dilator are in register or in alignment with each other. When locked, the needle 22 and the dilator 24 are inhibited from at least unintentional rotational and axial movement relative to each other. Further, as discussed herein, the dilator 24 (e.g., by way of its hub 38) can attach to the track 30. Thus, locking between the needle hub 34 and the dilator hub 38 can secure the needle 22 to other elements of the access device.

In the pre-loaded state, the dilator hub 38 is secured to the sheath hub 42. This can inhibit at least unintentional rotational and axial movement between the dilator 24 and the sheath 26. In embodiments where the sheath hub 42 and the dilator 24 have only a luer slip connection, the dilator 24 and sheath hub 42 may rotate relative to each other. However, such rotation (and other movement) can be still be resisted, for example, by optional frictional forces in the luer slip connection. Further, the sheath hub 42 can at times be fixed to other elements of the access device 20, such as the guidewire 40, in manners similar to those described above.

Figures 8A, 8B:
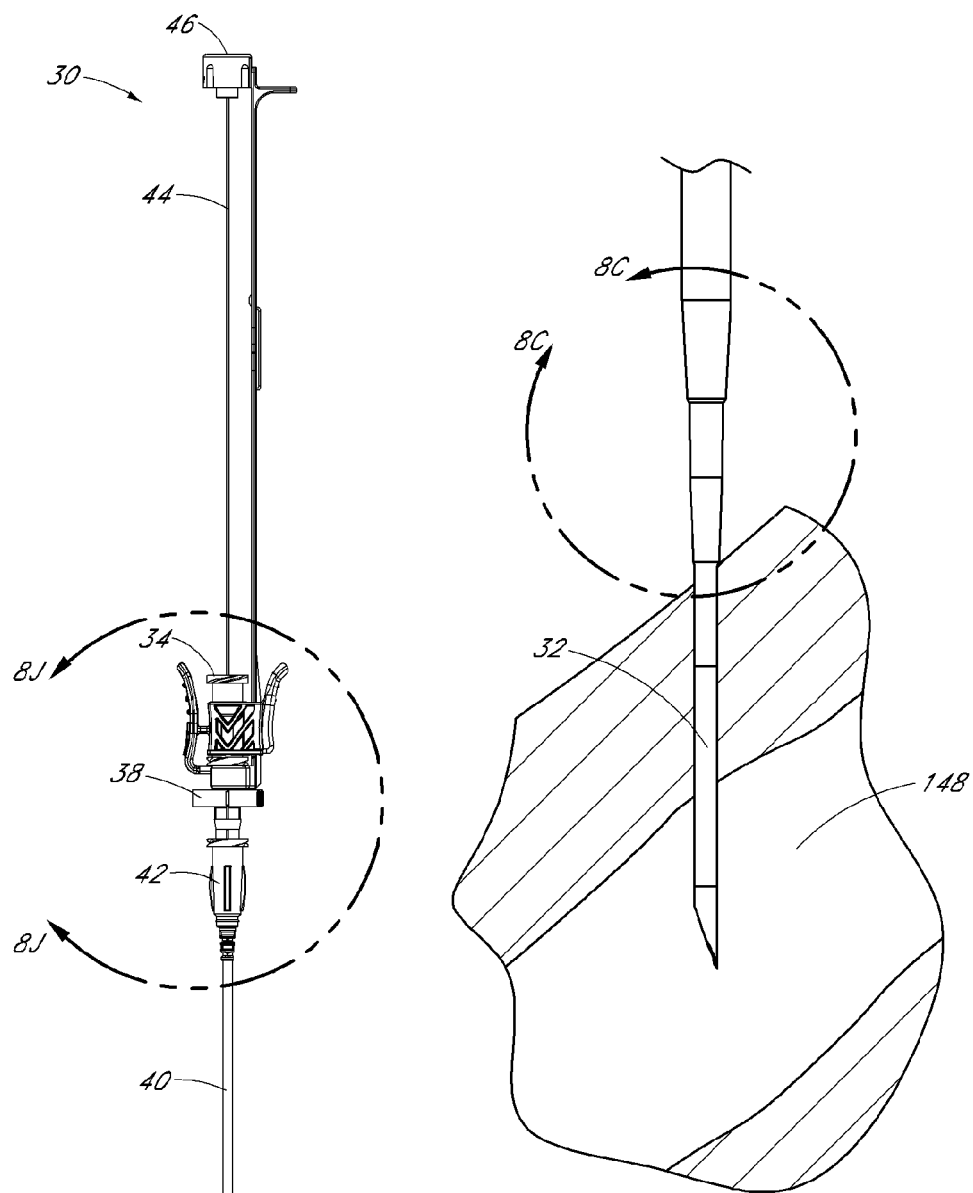
FIG. 8A is a plan view of the embodiment depicted in FIG. 1A illustrating the insertion of the distal end of the access device into a patient.
FIG. 8B is an enlarged view of the embodiment depicted in FIG. 8A focusing on the area of the access device adjacent to the patient.

FIG. 8A is a plan view of the embodiment depicted in FIG. 1A that illustrates an operational step of one method of using the access device 20. FIG. 8B is an enlarged plan view of the portion of the embodiment illustrated in FIG. 8A which is circled by line 8B-8B. FIGS. 8A and 8B depict the needle body 32 of the access device 20 inserted into a vessel 148, such as a vein or artery. While the described method refers to vascular access, the access device 20 also can be used to access and place a catheter or sheath into other locations within a patient's body (e.g., for draining an abscess) and for other purposes.

FIG. 8C is an enlarged plan view of the portion of the embodiment illustrated in FIG. 8B which is circled by line 8C-8C. FIG. 8D is an enlarged cross-sectional view of the embodiment depicted in FIG. 8C along line 8D-8D. FIG. 8E is an enlarged cross-sectional view of the embodiment depicted in FIG. 8C along line 8E-8E. FIGS. 8C-8E illustrate an embodiment of this mode of the access device, wherein a channel is formed between the needle and the dilator, to allow, for example, blood to flow during a blood flash. Referring to FIGS. 8C-8E, the needle body 32 includes one or more fenestrations 56 that allow blood to flow through the sidewall of the needle body 32 and into a space between the needle body 32 and the dilator shaft 36. One or more optional ridges 176 (e.g., two ridges 176 extending from the dilator shaft 36 are shown in the illustrated embodiment) can extend between the needle body 32 and the dilator shaft 36. The ridges 176 can define the sides of at least one channel 256 extending along a length of the needle body 32. In some embodiments additional channels 256 can be formed with additional ridges or other features. In some embodiments, the ridges 176 can include longitudinal gaps, to allow circumferential or transverse flow between adjacent channels formed by the ridges 176. In other embodiments channels 256 can be formed with a protruding ridge, or without a protruding ridge such as with a depression(s) or with a concentric gap. Channel 256 can be formed with protruding ridges (as shown) or non-protruding recessed grooves or flowpaths on the inner surface of the dilator shaft 36 and/or the outer surface of the needle body 32. Channel 256 can be formed without protruding ridges and/or grooves, and can simply comprise the annular space formed between needle body 32 and dilator shaft 36. Although the channel 256 is depicted as straight, it can also form other patterns such as a helix or another shape wrapping about the access device. Further, where multiple channels are present they can form intersecting helices, parallel helices, or other patterns. In other embodiments, a distance between the needle body 32 and a dilator shaft 36 (e.g. where the inner diameter of the dilator shaft exceeds the outer diameter of the needle body) can generally define a space, or a generally annular space, similar to the space created by the channels 256.

Figure 8F:
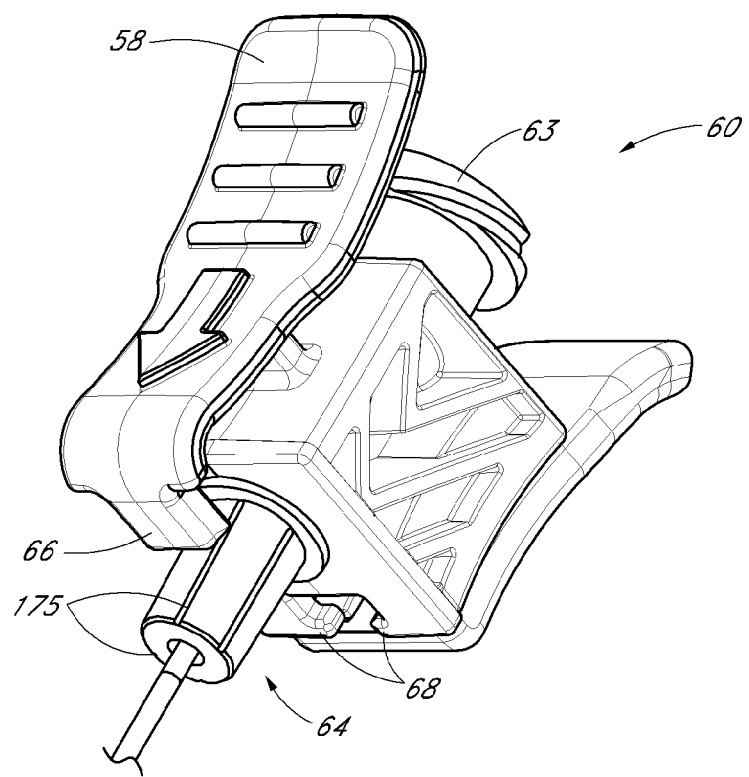
FIG. 8F is an enlarged perspective view of a needle hub configured to form part of the needle depicted in FIG. 8A.
Figure 8G:
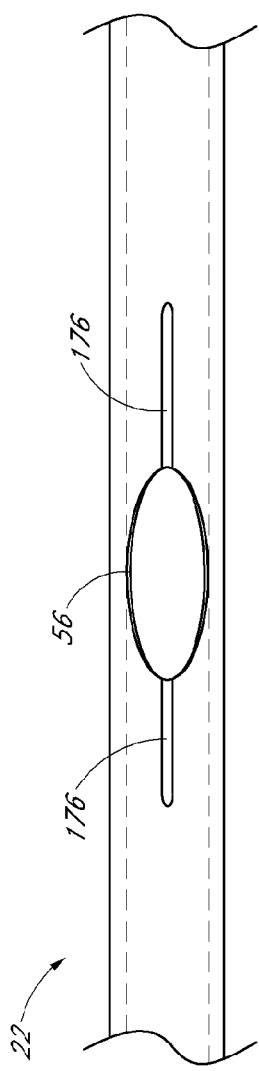
FIG. 8G is a plan view of a distal portion of another embodiment of a needle, with interior features in phantom.
Figure 8G:
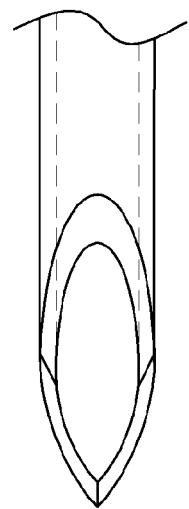
Figure 8H:
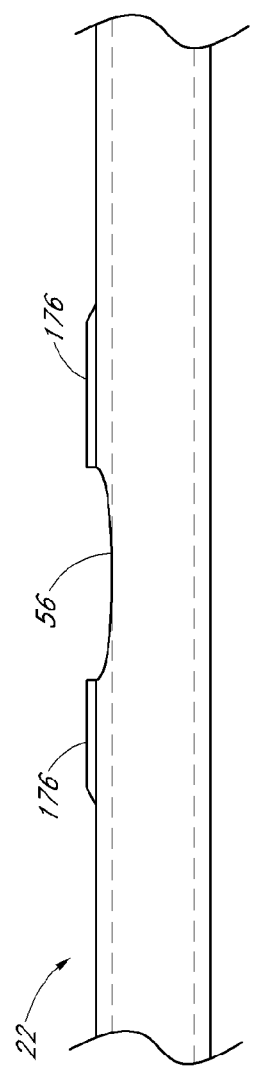
FIG. 8H is a side view of the needle of FIG. 8G.
Figure 8H:
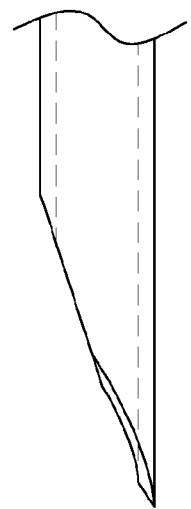

As best shown in FIG. 8F, the needle hub 34 can include one or more venting grooves 175. As depicted, the venting grooves 175 are on the luer connection 64, but in other embodiments they can be located on the needle body 32, on the dilator shaft 36, pass through the needle hub 34, pass through dilator hub 38, or take some other path. The venting grooves 175 can provide communication between the channels 256 (or similar spaces; FIGS. 8C-8D) and the ambient atmosphere. The luer connection 64 can be configured to cooperate with the dilator hub 38 to form a substantially liquid tight seal, such that a substance can only escape through the venting grooves 175. In embodiments where the venting grooves 175 do not extend radially, a generally radially extending side 180 of the needle hub 34 can be configured to rest far enough apart from a corresponding face 200 of the dilator hub 38 to allow air to pass between them, from the venting grooves 175.

In some embodiments, the venting grooves 175 can form a passage sufficiently small in cross-sectional area to allow the escape of gases (e.g., air) to the ambient atmosphere while hindering the escape to the ambient atmosphere of body liquids (e.g., red blood cells) with high molecular sizes, viscosities, or surface tensions. Further, in some embodiments multiple such passages can be provided, allowing adequate air ventilation despite small cross-sectional passages.

In other embodiments, the small cross-sectional area of the passage can be provided between two opposing surfaces of the dilator hub 38 and the needle hub 34. For example, at least a portion of the venting groove 175 on the needle hub 34 can be configured to receive a generally correspondingly shaped venting surface on the dilator hub 38 without entirely blocking the venting groove. The resulting passage between the surfaces of the needle hub 34 and the dilator hub 38 thus define at least a region of relatively small cross-sectional area to permit air flow but restrict the flow of bodily fluids.

While the venting structure is depicted as grooves 175 in the illustrated embodiment, other structures can perform similar functions. For example, a single reduced space location between the needle body 32 and the dilator body 34 can permit the escape of air while inhibiting the flow of blood proximally beyond the reduced space location. Similarly, a labyrinth passage can be disposed between the ambient atmosphere and the flash-back space (the space between the needle and dilator), such that gases can escape relatively quickly, but fluids would advance through the passage to slowly to escape during use of the access device 20.

In other embodiments, one or more of the venting grooves 175 can be filled at least in part by a porous material that permits gases to flow through the material but inhibits the passage of a body fluid (e.g., blood). Such material can be integrally formed into the needle hub 34 or dilator hub 38 such that the material and the hubs are unitary. The material can then comprise any portion of the length of the venting grooves 175. In other embodiments the material can be placed into the venting grooves 175 or a receptacle in communication with the groove(s). When the material is placed into the groove 175, the groove can include a receiving portion such as a groove notch configured to receive the porous material, such as that disclosed in PCT International Patent Application No. PCT/US2011/024097, filed Feb. 8, 2011, previously incorporated by reference in its entirety herein. One or more of the vent passages in other embodiments can be entirely formed by such porous material. Suitable porous materials include, but are not limited to a porous polymer such as HDPE, UHMWPE, PP, PTFE, PVDF, EVA, PE, Nylon, and PU, of pore size approximately 2.5 microns. In further embodiments, a combination of pore volume and pore size can be chosen to allow passage of gases (such as air) but inhibit the passage of body fluids (such as blood).

In further embodiments, the venting passages can be tubes defined solely by either the needle hub 34 or the dilator hub 38. For example, the channel 256 can lead to an opening in the needle hub 34. This opening can include any of the characteristics discussed above to control the passage of gases and fluids. The opening can thus allow the escape of gases (e.g. air) through the needle hub 34 to the ambient atmosphere while inhibiting the passage of body fluids (e.g. blood). In other embodiments, a similar venting passage can be a tube defined solely by the dilator hub 38. It will be clear from the disclosure herein that a variety of passages (e.g. venting grooves 175, tubes, porous material, etc.) can be used to allow the escape of gases (e.g. air) to the ambient atmosphere while inhibiting the escape of body fluids (e.g. blood).

In another embodiment, the venting passages can be within the dilator shaft 36 and the sheath body 40. For example, a venting hole or a patch of venting material can be provided in each of the dilator shaft 36 and the sheath body 40. In some embodiments these venting structures can overlap, allowing gases to pass directly from one to the other. In other embodiments, these venting structures can be positioned some distance away from each other, in which case a channel or groove similar to those in FIG. 8F can be provided between the dilator shaft 36 and the sheath body 40 to bring the venting structures into communication. These venting structures can be provided proximal from the fenestration 56 in the needle body 32.

The dilator shaft 36 in this embodiment can have no fenestration and can be generally continuous. The dilator shaft 36 can thus radially close the channel 256 (or similar space). In similar embodiments the same functionality can be accomplished with ridges in the dilator shaft 36 cooperating with an otherwise generally continuous needle 32 including a fenestration 56. The dilator shaft 36 can be formed of a translucent material in the entirety, or alternatively be translucent in at least the region adjacent the channel 256. The sheath body 40 can be similarly formed of a translucent material. In other embodiments, the material of the dilator shaft 36 or the sheath body 40 can be transparent instead of only translucent. In further embodiments, the material can be only partially translucent both spatially and temporally. Spatially, the material of the dilator shaft 36 and/or the sheath body 40 can be translucent near the channel 256, allowing visual confirmation of e.g. blood flash-back. Temporally, the visual characteristics of the material can change upon entry of a body fluid (e.g. due to temperature change or molecular interaction). The material can thus become translucent upon entry of a body fluid, or in other embodiments change color or provide some other visual indication.

In other embodiments, the channel 256 can be formed by having one complete ridge on the inner surface of the sheath and one complete ridge on the outer surface of the dilator. In other embodiments, the inner surface of the sheath can have two ridges that run 50% of the length of the channel 256 and the outer surface of the dilator can have two ridges that run the remaining 50% of the channel 256.

The sheath body 40, as noted previously, is preferably made partially or completely from clear, semi-opaque, translucent, or transparent material so that when blood flows into the needle body 32, (1) through the needle side opening 56, and (2) into a channel 256, the physician or healthcare provider can see the blood through the sheath body 40 and the dilator 24. In some modes, the channel 256 is formed between the needle body 32 and the dilator shaft 36 and defined by one or more ridges 176 on the needle body 32. In some modes, the channel 256 is formed within a wall of the dilator shaft 36 with the dilator shaft 36 preferably comprising a transparent material. Blood will indicate to the physician or healthcare provider that the bevel tip 54 of the needle body 32 has punctured a vessel 148.

The channel 256 can have an axial length that is almost coextensive with the length of the sheath 26 and/or dilator 24. In other embodiments, the channel 256 can be significantly smaller than the elongated channel 256 just described. For example, but without limitation, the channel 256 can be disposed within a distal, mid and/or proximal portion(s) of the dilator shaft 36. The channel 256 alternatively can have a linear, curved or spiral shape along an axial length of the dilator shaft 36 or can be formed by a plurality of such shapes. The channel 256 may have various thicknesses and span angles. The thickness of the channel 256 can range from almost close to zero to 0.010 inches. Preferably, the channel 256 has a thickness of about 0.0005 to about 0.003 inches. More preferably, the channel 256 can have a thickness of about 0.001 inches to about 0.002 inches. The channel 256 can have a span angle Φ about the axis of the dilator 24 of about 30 degrees to about 210 degrees or more, but preferably less than 360 degrees. More preferably, the channel 256 can have a span angle Φ of about 60 to 150. In the illustrated embodiment, the channel 256 spans 120 degrees. The thickness and span angle Φ can be chosen so as to optimize the capillary action that occurs within the channel 256 as fluid (e.g., whole blood) enters the channel 256 as may further be selected based on the expected pressure in the body cavity and viscosity of the liquid. Various graphs of test data illustrating how quickly a fluid is drawn up the surfaces of a channel within an access device are disclosed in PCT International Patent Application No. PCT/US2011/024097, filed Feb. 8, 2011, previously incorporated by reference in its entirety herein.

The shape of the channel 256 described above and the resulting capillary action was optimized for use with whole blood as opposed to other fluids having a different viscosity than whole blood (e.g. leukocytes, pus, urine, plasma). However, the shape of the channel 256 is not limited to the disclosed shape and may be optimized for draining other liquids, such as pus. Further, the shape of the channel 256 described above was optimized for peripherally located vessels where the pressure in the vessel enhances the capillary action and resulting blood flash as well as for vessels located in the regions where the pressure may be low. For example, in the thorax region of the body, the expected pressure in the veins may be lower than in a peripherally located vein when the patient breathes. A different size of the channel for use of the access device 20 in other regions of the body may be employed taking into account the expected pressure within the vessel or body cavity.

The access device described herein can include one or more surface coatings or treatments applied to one or more of its surfaces. For example, in some embodiments, a surface treatment or coating can be applied to one or more of the interior of the dilator shaft 36 (e.g., inner surface 152), the exterior of the needle 32 (e.g., outer surface 154), the inner surface of the needle body 32, an outer-surface 160 of the dilator shaft 36, an inner surface 158 of the sheath body 40, an outer surface of the sheath body 40 and/or the guidewire 44. These surfaces can be coated with a surface treatment individually, or in combination with each other, depending on the desired effect. A variety of surface coatings or treatments can be implemented, such as surfactants, lubricious coatings, and/or coatings with desired hydrophilic and/or hydrophobic properties.

In some embodiments, it may be preferable to coat both the outer surface 154 of the needle body 32 and an inner surface 152 of the dilator shaft 36 with a surfactant or other material that promotes or enhances progression of a body fluid through the channel 256. In the aforementioned embodiments that include a channel positioned between a dilator shaft and a sheath body, the surfactant or other flow-enhancing material can be supplied on the inner surface of the sheath and the outer surface of the dilator. However, in some embodiments it may be preferable to only coat one of these two surfaces. For example, the flow-enhancing material can be applied solely to the outer surface of the needle, solely to the inner surface of the dilator, or solely to the inner surface of the needle. A surfactant or other flow-enhancing material can ease the passage of a fluid through spaces within the access device, accelerating flashback and facilitating the progression of blood through the needle, dilator, and/or sheath. One example of a surfactant that can be used is Lutrol 68™, commercially available from BASF™; other surfactants can also be used. In some embodiments, a hydrophilic material can be implemented to provide similar enhanced capillary action.

Using the aforementioned surfactant, hydrophilic material, and/or other flow-enhancing material allows smaller needles, dilators, and/or sheaths to be used while still allowing blood to travel through said pieces with sufficient speed to indicate to an operator that the needle has entered the vessel or drainage site. Notably, in most embodiments a body fluid will pass through the needle, and thus in most embodiments it can be desirable to apply a surfactant or other flow-enhancing material to the interior surface of the needle.

In some embodiments, a lubricious coating or surface treatment, such as some hydrophilic substances, can be applied to the outer surface of the sheath 26 to act as a lubricant to ease insertion of the sheath 26 into a patient. Such lubricious coatings can be implemented individually, or in combination with the aforementioned flow-enhancing materials, and can be used on the same or different components of the access devices described herein. For example, lubricants or lubricous coatings can be used on the exterior of the sheath 26 and/or the outer surface of the sheath can be formed of a lubricous material. Additionally, the sheath 26 can be coated or formed with agents (e.g., heparin), which elute from the sheath, to facilitate the clinical application of the access device 20. In one example, the outer surface of the sheath 26 can include a coating of silicone, such as Dow Corning 360 Medical Fluid, 12,5000 CST™, commercially available from Dow Corning.

Additional or alternative surface treatments or coatings can be used, for example, to slow or inhibit flashback and fluid flow within one or more components of the access device. Such flow-inhibiting substances (e.g., suppressors or decelerants) can be implemented individually, or in combination with the aforementioned flow-enhancing materials and/or lubricious materials, and can be used on the same or different components of the access devices described herein. For example, a flow-inhibiting coating may be implemented to prevent the access device from falsely indicating a blood flash through contact with capillaries prior to the access device entering an artery or vein. Some hydrophobic substances can implemented to act as a flow-inhibiting coating.

In some embodiments, sheath 26 (e.g., sheath body 40) can comprise a material with sufficient flexibility to facilitate the insertion of sheath 26 into a patient. In some embodiments, sheath body 40 can comprise a material that varies in flexibility, depending on the environment to which it is exposed. For example, sheath body 40 can comprise a material that varies in flexibility and/or rigidity based upon the temperature to which sheath body 40 is exposed. In a preferred embodiment, sheath body 40 comprises a material that softens to exhibit a reduced rigidity and/or increased flexibility upon exposure to heat, e.g., a temperature increase. For example, sheath body 40 can comprise a material that softens to exhibit reduced rigidity and/or increased flexibility in response to contact with a patient or in-vivo insertion into a patient. In some embodiments, the material can exhibit such reduced rigidity and increased flexibility in response to an increase in temperature falling within a range of approximately 2-20 degrees Celsius. In some embodiments, the material can exhibit such reduced rigidity based upon a change in temperature of approximately 11-17.5 degrees C. In some embodiments, the material can exhibit such reduced rigidity and increased flexibility in response to a change in temperature from approximate room temperature (ranging from approximately 20-25 degrees Celsius) to the body temperature of a patient (ranging from approximately 30-45 degrees Celsius, including 35-40 degrees Celsius for humans and animals, including but not limited to canines, felines, equines, bovines, ovines, porcines, and other domestic and wild animals including mammals).

In a yet more preferred embodiment, the sheath body 40 comprises a urethane polycarbonate, or another form of urethane, or another plastic or non-plastic material that provides similar properties (such as a similar durometer, modulus of elasticity, modulus of rigidity (shear modulus), water absorption, melt flow, chemical resistance, and/or bulk modulus). In some embodiments, the sheath body 40 comprises ether-free polyurethane elastomers. In some embodiments, during the insertion of sheath body 40 into a patient, sheath body 40 can absorb heat from the body of a patient or from other heat sources, and in response, reduce its rigidity. Such reduced rigidity can increase comfort to the patient, and/or reduce the likelihood of injury or tissue damage to the patient during the insertion and use of sheath 26. For example, when a fluid is injected through a substantially rigid tube, the tube can respond to this pressure by creating an oscillatory whipping motion. Reducing the rigidity of the sheath body 40 can reduce the strength of such motion during injection or other fluid transfers. Examples of bio-compatible materials that can be used for sheath 26 (e.g., sheath body 40), and that can include one or more of the properties described herein, such as increased flexibility upon exposure to heat, are manufactured by AdvanSource Biomaterials Corp. (e.g., ChronoFlex C®) and Lubrizol (e.g., Carbothane TPU®).

Figure 8I:
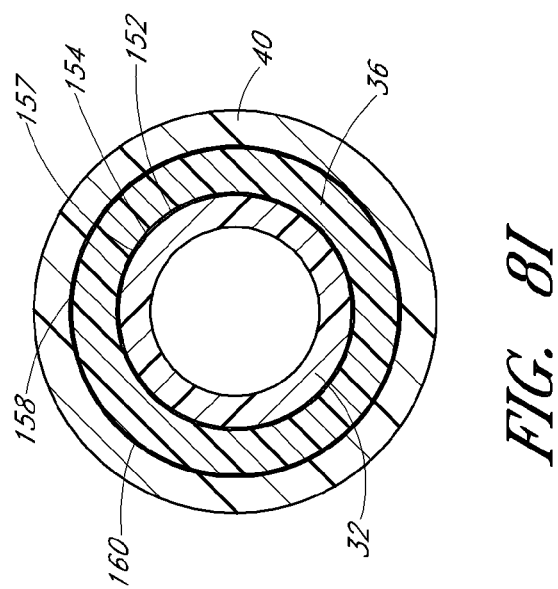
FIG. 8I is an enlarged cross-sectional view of the embodiment depicted in FIG. 8C distal to the needle opening along line 8I-8I.

FIG. 8I is a cross sectional view of the embodiment depicted in FIG. 8C along a line 8I-8I distal of fenestration 56. In this region of the illustrated access device 20, the sheath body 40 is coaxially positioned to minimize an annular space 157 between the needle body 32 and the dilator shaft 36 while still allowing relative movement of the needle body 32 and the dilator shaft 36. The inner surface 152 of the dilator shaft 36 need not, though it can, lie directly against the outer-surface 154 of the needle body 32. The annular interface 157 between the outer-surface 154 of the needle body 32 and the inner surface 152 of the sheath dilator shaft 36 may be reduced in this region to inhibit the distal flow of blood or its constituents (or other fluids) from the opening 56 in the needle body 32.

Continuing to refer to FIG. 8I, the dilator shaft 36 can have an inner diameter d1 in a portion distal from the fenestration 56 (FIG. 8C). Further, needle body 32 can have an outer diameter d2. In some embodiments, d1 can be less than d2; this can provide a number of advantages. For example, the interference fit of the dilator shaft 36 on the needle body 32 can put the dilator shaft 36 under a radial or hoop load. This loading can increase the strength of the dilator shaft 36 in an axial direction. The increased strength tends to reduce flaring, crimping or buckling of the material at the distal tip of the dilator when inserting the dilator through tissue (e.g., skin, muscle and/or vascular wall). For example, as the needle body 32 and dilator shaft 36 pass through skin (without the use of a skin nick) the dilator can withstand axial forces that may otherwise deform the distal tip of the dilator. In some embodiments, this could cause a dilator to bunch, fold, or curl upon itself, increasing its cross-sectional area at said bunch or fold and inhibiting its functionality as a dilator. In other words, the deformed dilator becomes too difficult to insert into the patient. Providing the dilator with a smaller inner diameter d1 can increase the strength of the dilator, inhibiting the occurrence of such deformations. Advantageous ranges of the inner diameter of a dilator shaft with respect to the outer diameter of a needle are disclosed in PCT International Patent Application No. PCT/US2011/024097, filed Feb. 8, 2011, previously incorporated by reference in its entirety herein.

Figures 9A, 9B:
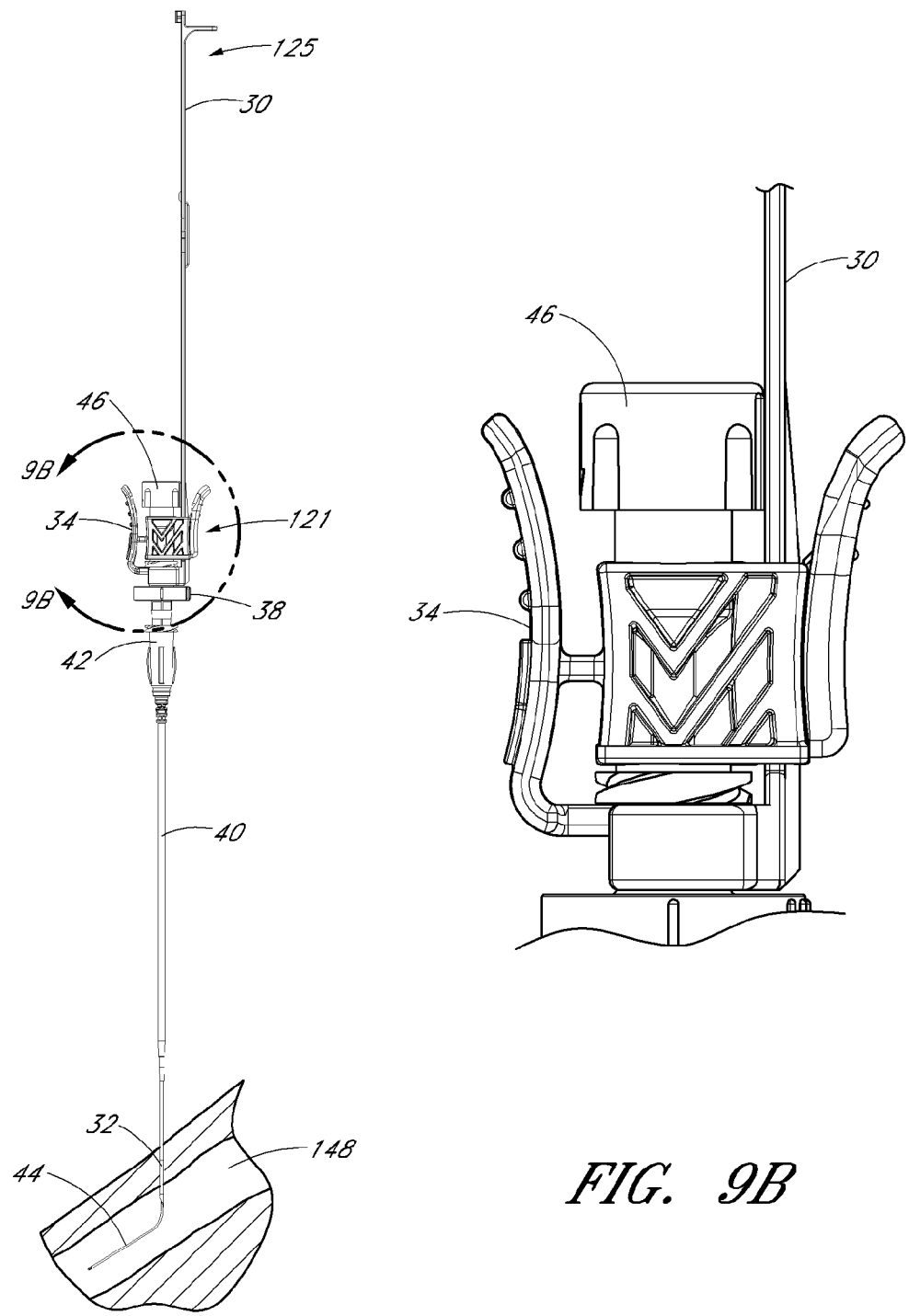
FIG. 9A is a side view of the embodiment depicted in FIG. 1A illustrating the guidewire advanced from the needle tip in a distal direction.
FIG. 9B is an enlarged view of the embodiment depicted in FIG. 9A focusing on the area where the guidewire hub is locked to the needle hub when the needle hub is in the first position.

FIG. 9A is a side view of the embodiment depicted in FIG. 1A that illustrates a further operational step of the access device 20. FIG. 9A depicts the guidewire 44 of the access device 20 advanced in a distal direction into a vessel 148. This can be achieved by advancing guidewire hub 46 from the third position 125 in a distal direction. The guidewire hub 46 is then locked to the needle hub 34 when the needle hub 34 is in the first position 121.

Figure 9C:
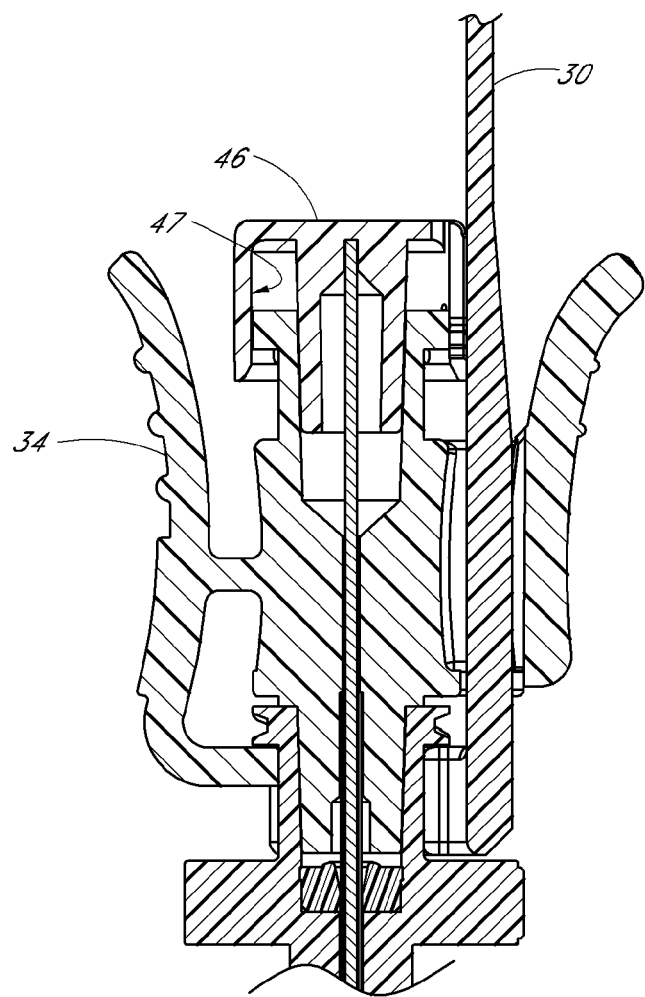
FIG. 9C is a cross-sectional view of the embodiment depicted in FIG. 9B.

FIG. 9B is an enlarged side view of the portion of the embodiment illustrated in FIG. 9A which is circled by line 9B-9B. FIG. 9C is a cross-sectional side view of the embodiment depicted in FIG. 9B. FIG. 9C illustrates the locking mechanism between the guidewire hub 46 and the needle hub 34. Preferably, the guidewire hub 46 is configured to mechanically fit and releasably or irreversibly interlock with the needle hub 34. The guidewire hub can lock onto the needle hub 34 in any of a number of ways, including the various locking mechanisms described herein for other components of access device 20. In the illustrated embodiment, the guidewire hub 46 can lock to the needle hub 34 via corresponding threaded elements 47, positioned, for example, on an inner surface of guidewire hub 46 (FIG. 9C). PCT International Patent Application No. PCT/US2011/ 024097, filed Feb. 8, 2011, previously incorporated by reference in its entirety herein, and PCT International Patent Application No. PCT/US2009/037198, filed Mar. 13, 2009, and incorporated by reference in its entirety herein, disclose additional locking mechanisms, including a nub on the inner surface of a guidewire hub that engages with a groove on the lip of a needle hub 46.

FIG. 10A is a side view of the embodiment depicted in FIG. 1A that illustrates another operational step of the access device 20. FIG. 10A depicts the dilator shaft 36 and the sheath body 40 advanced in a distal direction into a vessel 148. This can be achieved by releasing the dilator hub 38 from the needle hub 34 and advancing the dilator 24 and sheath 26 in a distal direction relative to the needle hub 34 along the guidewire and needle. FIG. 10A further illustrates the proximal movement of the needle 22 and guidewire section 28 relative to the dilator 24 and the sheath 26. The needle hub 34 will lock to the track 30 when the needle hub 36 reaches the second position 123.

FIG. 10B is an enlarged bottom view of the portion of the embodiment illustrated in FIG. 10A which is circled by line 10B-10B, and with handling portion 59 not shown for clarity. As depicted in FIG. 10B, the needle hub 34 locks onto the track 30 via the locking mechanism 128 in the second position 123. The needle hub tangs 68 slide in a proximal direction over the track fingers 138 and the tangs 68 can lock into place between the track fingers 138 and the track section of increasing width 134. This configuration hinders and, in some embodiments substantially irreversibly prevents axial movement of the needle body 32 at least in the distal direction when the needle hub 34 is in the second position 123. In the illustrated embodiment, the locking mechanism 128 hinders the needle hub 34 from moving in either the proximal or distal directions once engaged. Furthermore, the distal tip 54 of the needle 22 is drawn into the dilator 24 to sheath the distal tip 54 when the needle hub 34 is in the second position 123. Thus, this locking mechanism 128 inhibits the bevel tip 54 disposed on the distal portion 50 of the needle body 32 from being advanced beyond the distal end of the dilator shaft 36 once the dilator shaft 36 has been advanced over the needle body 32 during use. The dilator shaft 36 thus sheaths the sharp bevel tip 54 of the needle body 32 to inhibit accidental needle sticks from occurring.

Figure 11B:
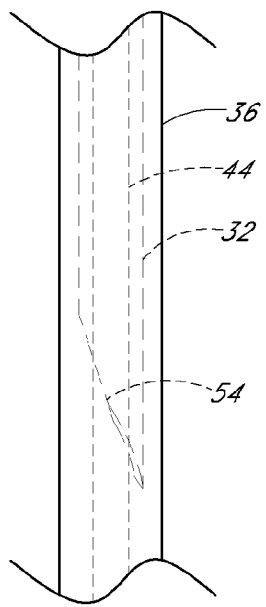
FIG. 11B is an enlarged view of the portion of the embodiment illustrated in FIG. 11A showing the needle tip covered by the dilator during removal of the guidewire, needle body, and dilator from the sheath.
Figure 11A:
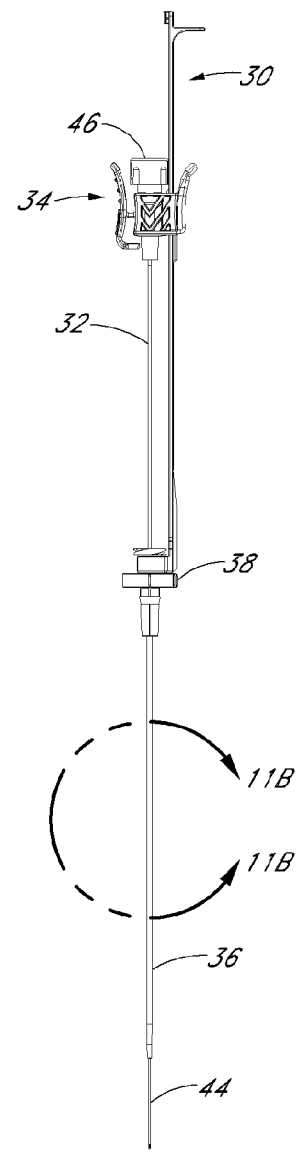
FIG. 11A is a side view of the embodiment depicted in FIG. 1A illustrating the removal of the guidewire, needle body, and dilator from the sheath.
Figure 11A:
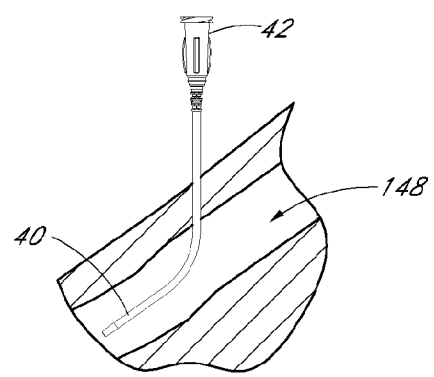

FIG. 11A is a side view of the embodiment depicted in FIG. 1A that illustrates one of the final operational steps of the access device 20. FIG. 11A illustrates the removal of the guidewire 44 and the dilator shaft 36 from the vessel leaving the sheath body 40 properly inserted within the vessel 148. FIG. 11B is an enlarged plan view of the portion of the embodiment illustrated in FIG. 11A which is circled by line 11B-11B. As clearly shown in FIG. 11B, the distal end of the dilator shaft 36 and the guidewire 44 extend beyond the sharp bevel tip 54 of the needle body 32 to inhibit accidental needle sticks from occurring.

As described further herein, the access device includes a fluid flash-back space defined between the shaft of the needle and the shaft of the dilator (e.g., FIGS. 8C-8E). In this mode, the flash-back space preferably vents to the atmosphere and more preferably vents independent of the sheath. In particular, as described above, a vent passage can be formed through the dilator, through the needle, or between the dilator and the needle.

Figure 12A:
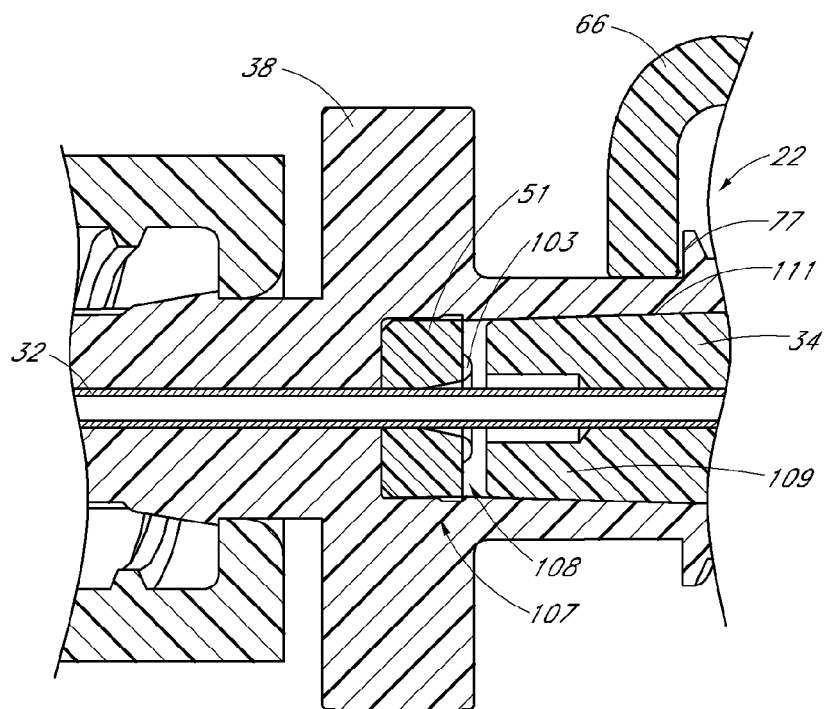
FIG. 12A is an enlarged cross-sectional view of another embodiment of an access device showing portions of a needle hub, a dilator hub, and an insert.
Figure 12B:
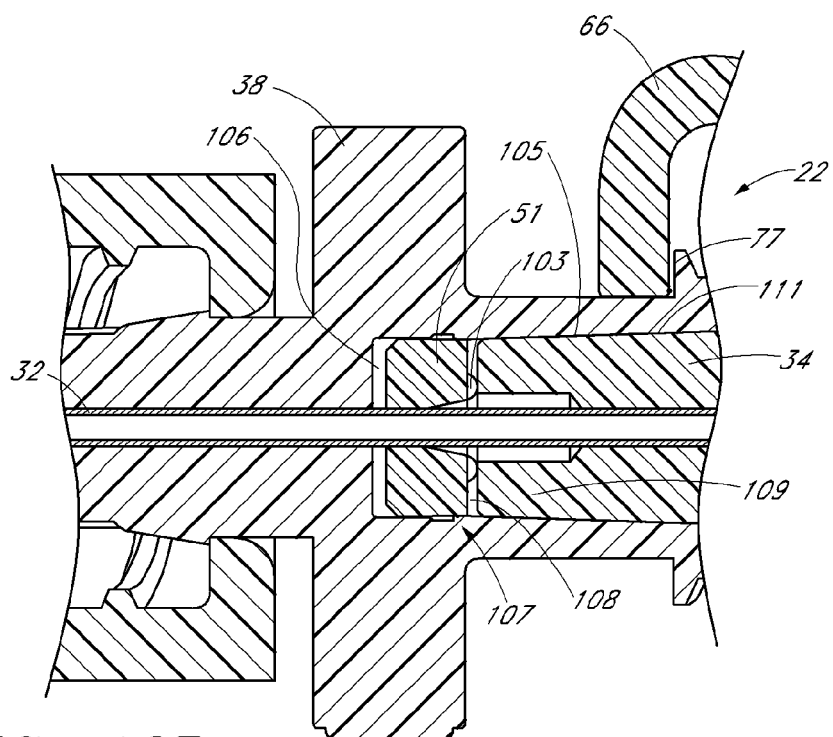
FIG. 12B is an enlarged cross-section view of the access device of FIG. 19A, wherein an insert is not fully inserted.

In even further embodiments, the venting can be provided at least partially through an insert 51 between a dilator hub 38 and needle hub 34, as best shown in FIGS. 12A, 12B. In some embodiments, an additional piece such as the insert 51 can facilitate the provision of certain desirable dimensions, materials, and other design features that might not be otherwise possible or economical. For example, in the embodiment discussed above regarding FIGS. 8C-8E, it may be desirable for a middle portion of the dilator shaft 36 to have an inner diameter substantially larger than the outer diameter of the needle body 32 near a needle fenestration. This difference in diameters can create a space that allows a body fluid to flow between the two (such as in the channel 256) from the fenestration. However, as will be discussed above, in some embodiments it may also be desirable to provide the dilator shaft 36 with a smaller inner diameter near the dilator's distal tip. In further embodiments (such as those described above) it may be desirable to provide a proximal portion of the dilator 424 that also has a smaller diameter to hinder the flow of a body fluid such as blood proximally while still allowing the venting of gases. As discussed above, this venting can facilitate the drawing of a body fluid into the space, cavity, or channel. However, it may be difficult to manufacture a dilator 24 with small inner diameters at its proximal and distal ends, and a large inner diameter in a middle portion.

Figure 12C:
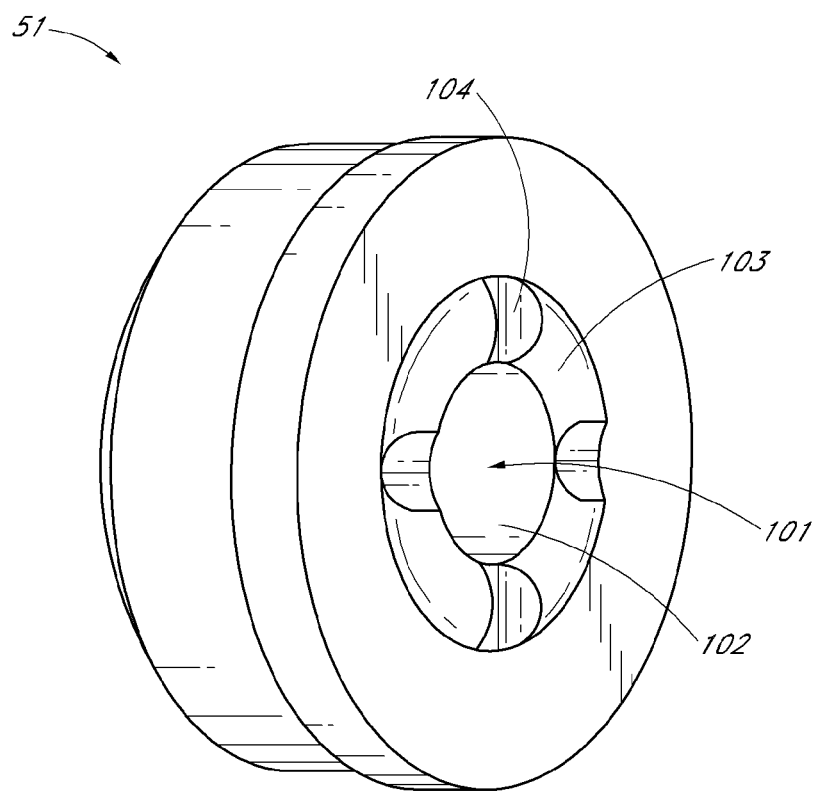
FIG. 12C is an enlarged view of an insert of the access device of FIG. 19A.

The embodiment depicted in FIGS. 12A-12C provides venting with the assistance of an insert 51. The insert 51 can be disposed within a proximal opening 107 of the dilator hub 38. The proximal opening 107 can be configured to also receive a distally protruding portion 109 of the needle hub 34, as described in similar embodiments above (e.g., the portions forming a luer fitting between the needle and dilator hubs). In some embodiments the insert 51 can be press-fit into the dilator hub 34, while in other embodiments it can be loosely slid onto the needle body 32 (e.g., prior to combination with the dilator 424).

As best depicted in FIG. 12C, the insert 51 defines a through-hole 101 that can slidingly receive the needle 22 (or another needle described herein), e.g. along the needle body 32. Further, as depicted, the insert 51 can be substantially circular, or donut-shaped, allowing flexibility in its rotational position within the dilator hub 38. However, in other embodiments the insert 51 can be rotationally fixed within the dilator hub 38, i.e., with a non-circular insert and a corresponding non-circular receiving portion in the dilator hub 38.

Even further, the insert 51 can have particular dimensions to facilitate the release of gases while hindering the release of body fluids. For example, the diameter of the insert's through-hole 101 can be only slightly greater than the outer diameter of the needle body 32, creating a space or gap (not shown) between insert 51 and needle body 32, the gap sized to allow the release of gases but hinder the release of a body fluid. As best shown in FIGS. 12A, 12B, the gases can then flow proximally within the gap between insert 51 and needle body 32 and enter a space 107, 108 between the needle hub 34 and the insert 51 within the receiving portion or opening 107 of the dilator hub 38. From this space, the gases can then proceed to the ambient atmosphere in a passage 111 defined between the needle hub 34 and the dilator hub 38. Notably, although in some embodiments the needle hub 34 and the dilator hub 38 can connect via a luer connection that may prevent the passage of gases, additional mechanisms known in the art or described herein can also attach the two hubs. For example, in the depicted embodiment the needle hub 34 can include latch element 66 that can releasably hook to a ledge portion or lip 77 of the dilator. Thus, components that might otherwise form a luer connection between the two hubs can also be sufficiently separated to allow the escape of gases without compromising a connection between the hubs.

Further, the outer edge of the insert 51 can be shaped to substantially match the receiving portion of the receiving portion of the dilator hub 38 to form a seal between the two that at least hinders the escape of a body fluid therethrough. In some embodiments, a taper 105 within the dilator hub 38 (also used for a luer connection with a needle, as discussed above) can facilitate a seal between the insert 51 and the dilator hub. In some embodiments, the seal between the outer edge of the insert 51 and the receiving portion 107 of the dilator hub 38 can also be impermeable to gases, forcing their passage through the through-hole 101, as described above.

During assembly, when the insert 51 is inserted into the dilator hub 38, the insert can sometimes enter slightly off-angle from the receiving portion and thus be stuck slightly askew. Due to the size of the pieces and the depth of the receiving portion 107, it may be difficult to detect when the insert 51 is askew. Thus, the insert 51 can be configured to provide tolerances for such off-angle insertion. For example, as depicted the through-hole 101 can include a proximally-tapered portion 102 (FIG. 12C). The proximally tapered portion 102 can help preserve a venting space between the needle body 32 and the insert 51 through which gases can escape but the escape of a body fluid can be hindered.

The insert 51 can also include a proximally projecting portion depicted as a ridge 103 along its proximal face, which can be of particular relevance as shown in FIG. 12B. For example, if the insert 51 is askew, it may not completely insert into the dilator hub 38, leaving a gap 106 between the insert 51 and a distal portion of dilator hub 38 within opening 107, as depicted in FIG. 12B. Gap 106 could allow the insert 51 to come into contact with the needle hub 34, potentially forming a seal, preventing the escape of gases through the insert's through-hole 101. Thus, in some embodiments, the insert can also include a ridge 103 with one or more grooves 104. The needle hub 34 can contact the ridge 103 before contacting the rest of the proximal end of the insert 51, preserving a space therebetween. The one or more grooves 104 provide an opening or channel in the ridge 103 for gases to pass through, to the passage 111 between the hubs 34, 38. In the depicted embodiment, more than one groove can be provided to advantageously allow gases to pass through in multiple directions. Thus, if sealing contact between the insert 51 and the needle hub 34 is made on one side, gases can still escape on the other side.

In other embodiments, the proximally projecting portion on the insert 51 can take other forms. For example, in some embodiments the insert 51 can have one or more distinct projections to maintain separation from the needle hub 34. In further embodiments, the insert 51 can include one or more grooves that allow the escape of gases despite contact with the needle hub 34. Even further, in some embodiments similar structures can be provided on the needle hub instead of or in addition to the structures on the insert.

The passages described herein that allow ventilation of gases and that may inhibit passage of a liquid such as blood (e.g., passage 111, groove 104) may be sized to filter blood or other liquid or may include a filter or other. For example, the sheath or dilator itself may include one or more passages in the form of small openings, pores or porous material. Depending on the size of the one or more passages and the expected size of the fluid molecules and formed elements (e.g. red blood cells), the one or more small openings, pores or porous material in the sheath can form a porous vent that allows air to pass yet retain blood.

FIGS. 13A-13C depict another embodiment of a dilator 24B that includes additional elements to enhance the fluid flash-back feature of the access device 20. One additional element involves at least one wiper or seal that interacts with a needle (e.g., the needle 22 described in connection with the embodiment illustrated in FIGS. 1-7 above) about which the dilator 24B is coaxially disposed to inhibit fluid uptake thorough a space occurring between the needle exterior (e.g., needle exterior surface 154 of FIG. 8D) and the dilator interior (e.g., dilator interior surface 152 of FIG. 8D). The seal feature can be incorporated into any of the previously described embodiments of the access device 20, along with or separate from the other elements depicted in FIGS. 12A-12C. For example, the seal feature can have a smaller inner diameter and be on a dilator body associated with the dilator hub 38 depicted in FIGS. 12A-12C. While the illustrated embodiment describes this additional element in connection with a single seal, the dilator can include multiple seals located along the length of the dilator. Such seals can be located in series to the proximal side of the dilator fenestration and/or the needle fenestration. Additional seals can be located on the distal side of such fenestration as well in some embodiments; however, in the illustrated embodiment, the seal is depicted to the proximal side of both the dilator and needle fenestrations.

With reference to FIGS. 13A and 13C, the dilator 24B includes a sealing portion 250 that lies slightly proximal of a fenestration 56 on the needle body 32 when the dilator 24B is disposed within the needle body 32 (see, e.g., FIG. 8C). The sealing portion 250 is depicted as an inward protrusion that creates a narrowed region in the interior of the dilator 24B. At this sealing portion 250, the dilator 24B can form a seal with a needle (not shown) to separate the space between the dilator 24B and the needle into proximal and distal sections each lying to one side of the seal. One potential result is that, in embodiments where a fluid is intended to advance from the needle bore to a space between the needle body 32 and the dilator 24B (e.g., as described in connection with the embodiment illustrated in FIGS. 8C-8E above), fluid leakage into the proximal space between the dilator 24B and the needle is reduced, as the body fluid is inhibited from passing proximally beyond the sealing portion 250. Thus, flow can be further directed into the channel 256 between the needle body 32 and the dilator (e.g., dilator 24; FIGS. 8D-8E) to hasten viewing of a flash-back response. Further, in some embodiments the sealing portion 250 can serve as a wiper, removing fluid (e.g., blood) from the surface of the distal portion of a needle as it is retracted into the dilator 24B. The one or more sealing portions 250 can also provide radial support between dilator 24B and needle body 32, increasing the axial strength of the dilator shaft 36, providing advantages substantially similar to the configurations (e.g., diameters) of needle body 32 and dilator shaft 36, described further herein with reference to FIG. 8I.

The sealing portion 250 can take a variety of cross-sectional shapes, including triangular (an example of which is illustrated in FIG. 13C), rounded or rectangular. In the illustrated embodiment depicted in FIG. 13C, the sealing portion 250 has a generally triangular cross-sectional shape formed in part by a tapering surface 252 that slopes inward preferably in a proximal direction. The tapering surface 252 intersects with a ledge 251 of the sealing portion 250. The ledge 251 lies generally perpendicular to a longitudinal axis of the dilator 24B; however, in other embodiments, the ledge 251 can lie at various angles relative to the longitudinal axis so that an angle formed between the tapering surface 252 and the ledge 251 can be acute, right or obtuse. Advantageously, the tapering surface 252 on the sealing portion 250 can assist movement of the needle through the dilator 24B in a proximal direction. The ledge 251 allows the sealing portion 250 to deflect proximally as a needle is passing through. The dimension of the inward projection of the sealing portion 250 preferably is not significantly less than, and is more preferably greater than half of the difference in diameters between the exterior of the needle and the interior of the dilator at the point of the fenestrations.

As further depicted in FIG. 13A, in some embodiments the dilator 24B can include an expanded portion 260, formed with a taper 262 proximal of the sealing portion 250. The expanded portion 260 can provide space for the channel 256 between the needle body 32 and dilator shaft 36 (FIGS. 8D-8E), and can reduce contact and friction between the dilator 24B and a needle (or other article for that matter) passing through the dilator 24B. Additionally, in some embodiments a needle or other article passing through the dilator 24B can include a stop portion extending radially outward to engage the taper and inhibit further advancement of the article. Thus, the expanded portion 260 and its coinciding taper can limit axial and/or radial movement between the dilator 24B and a corresponding needle or other article, providing advantages substantially similar to the configurations (e.g., diameters) of needle body 32 and dilator shaft 36, described further herein with reference to FIG. 8I.

The sealing portion 250 can be formed on the dilator in any of a wide variety of ways readily known to those skilled in the art. For example, in some embodiments, the sealing portion 250 can be formed during a dilator tipping process after the dilator has been extruded. An internal mandrel can be cut with an annular groove that has the inverse image of the sealing portion 250. The mandrel is then placed within dilator. As the material of the dilator's distal end is heated during the tipping process and then pressed into the desired exterior shape, the material will also be forced into the annular groove on the mandrel to form the sealing portion 250. After sufficient cooling, the dilator can be withdrawn.

In other embodiments, a sealing portion can take a different form. For example, a needle can have an expanded exterior portion, forming an enlarged external diameter on the proximal side of its fenestration, similar to the enlarged internal diameter of the expanded portion 260 of the embodiment depicted in FIGS. 13A-13C. As such, the needle can have a smaller external diameter at a distal portion and a larger external diameter at a distal portion. The enlarged diameter portion can engage or abut against the internal surface of the dilator (e.g., against taper 262) to form a sealing portion similar to that described above. In some embodiments, the contact between the needle and dilator, forming a sealing portion, can be formed between matching tapers such as the taper 262 on the dilator 24B and a similar external taper on the needle. In other embodiments the contact between the needle and the dilator can be on other surfaces, such as surfaces generally parallel with the longitudinal axis of the needle and dilator.

Further, as depicted in FIG. 13A, the dilator tip can be beveled to provide a smoother dilation and to ensure further that the dilator tip does not deform upon entrance into the patient's body. As indicated, the tip can have a taper or bevel at an angle φ on each side (it is noted that the indicated angle φ's opposite angle is equal to φ, and thus they are treated as the same herein). The beveled tip can reduce axial forces on the dilator 24B upon passage through tissue (e.g., skin). In some embodiments, the angle φ can be approximately 30 degrees. In other embodiments, the angle φ can be between approximately 40 and 20 degrees. After this initial bevel, the dilator tip can taper at a shallower angle, as depicted in FIG. 13C. For example, in some embodiments the dilator can then taper at approximately 3 degrees, or alternatively at an angle less than approximately 3 degrees.

Figure 14A:
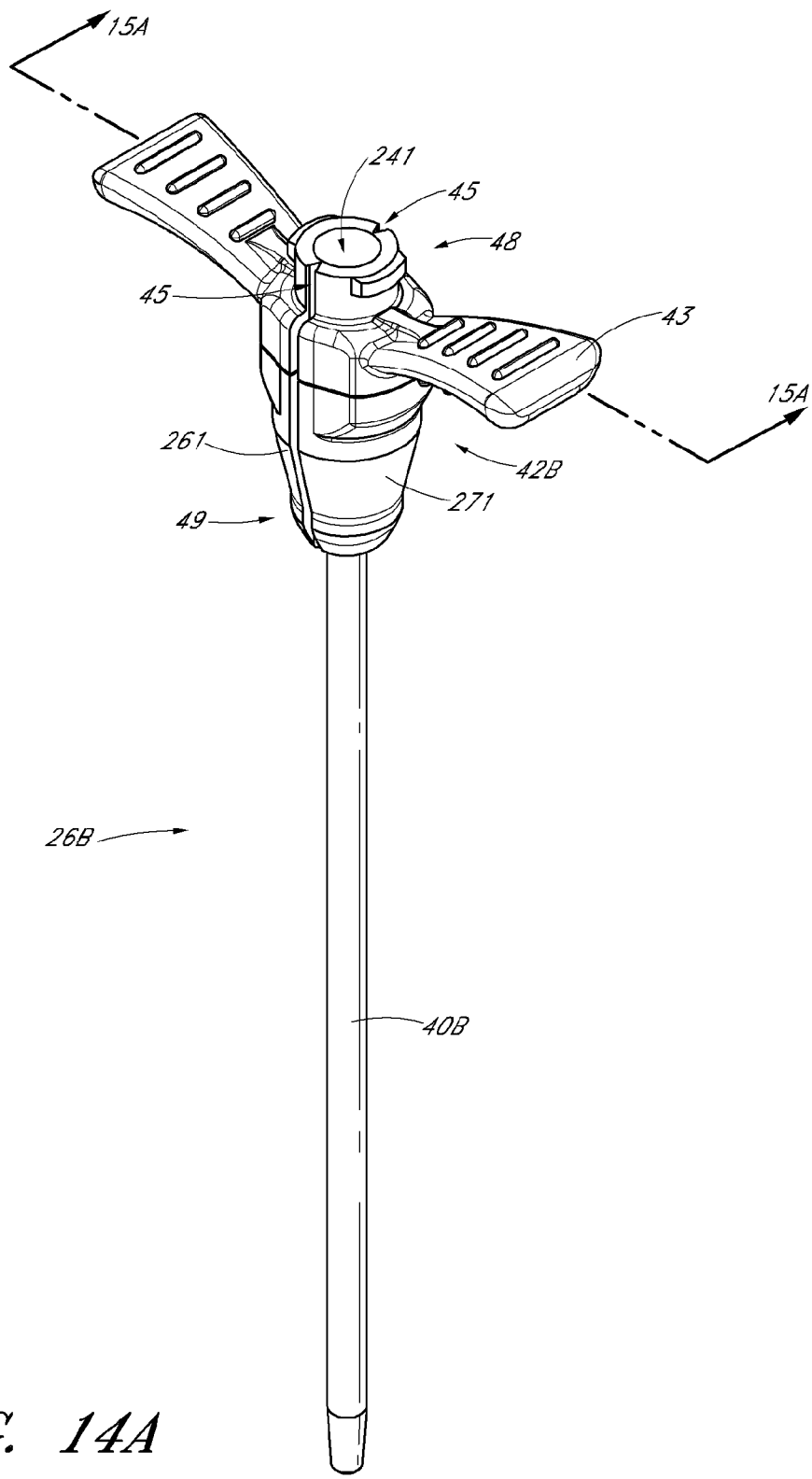
FIGS. 14A and 14B are a side isometric view and an exploded side isometric view, respectively, of an embodiment of a sheath.
Figure 14B:
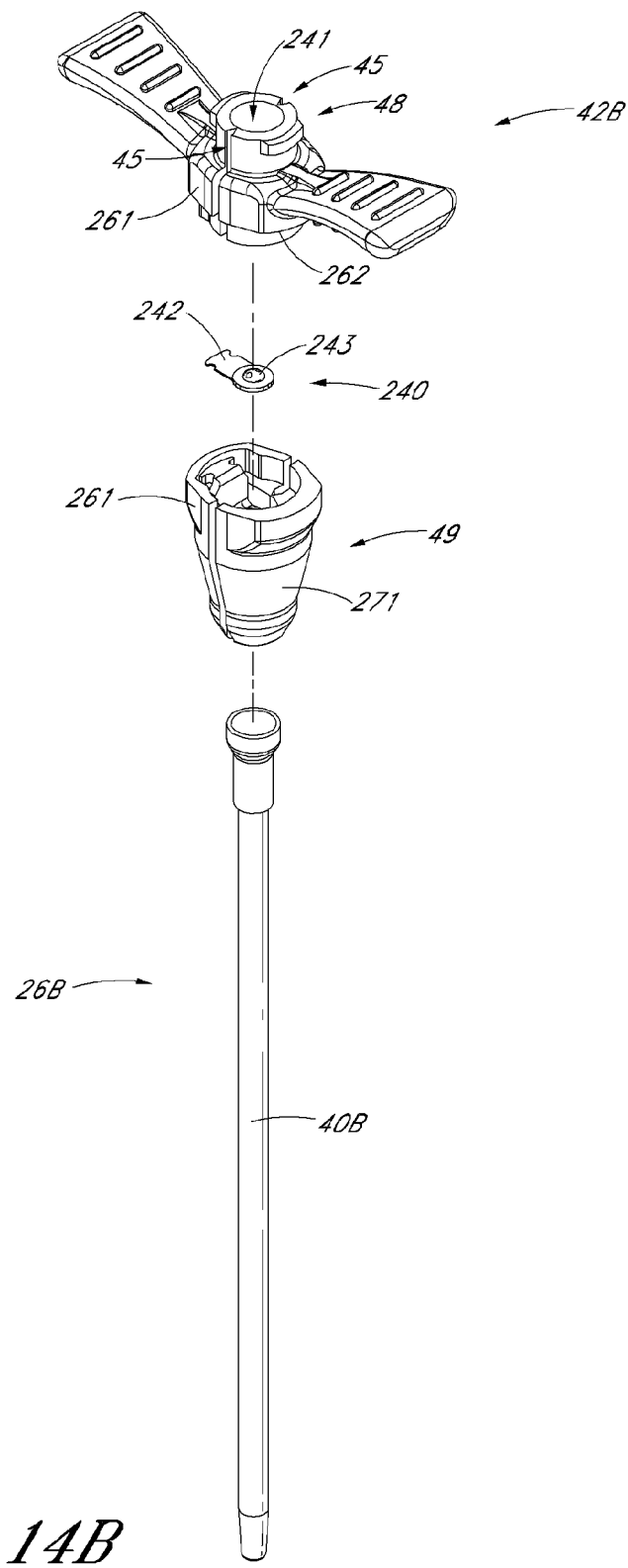

FIGS. 14A and 14B are a side isometric view and an exploded side isometric view, respectively, of an embodiment of a sheath 26B, that can optionally be used with the above described dilators, needles, guidewires, and other elements in a similar manner to the previously described sheaths. Sheath 26B can include a sheath body 40B and a sheath hub 42B, with an inner cavity 241 extending through or along a portion of sheath body 40B and/or sheath hub 42B (e.g., along one or more longitudinal axes thereof). Sheath hub 42B can extend from a proximal end of sheath body 40B. Sheath body 40B and/or sheath hub 42B can be optionally splittable along one or more split lines 45. In some embodiments, sheath body 40B and/or sheath hub 42B can be splittable along two or more split lines 45, to form two or more separable sections or halves, such as sheath hub sections 261 and 271. The embodiments of sheath 26B, including body 40B and hub 42B, can be generally similar to the embodiments of sheaths, sheath bodies, and/or sheath hubs discussed elsewhere herein (e.g., as shown in FIGS. 4J and 4K), with optional differences discussed below.

Referring, for example, to FIGS. 14B and 15A-15C, sheath 26B can include a valve element 240 configured to substantially seal a portion of inner cavity 241. Valve element 240 can include a resilient plate 242 supporting a sealing element 243. The resilient plate 242 can be supported by a portion of the sheath body 40B and/or hub 26B such that a portion (e.g., a sealing portion 264) of the resilient plate 242 can extend (e.g., radially inwardly) into and substantially seal the inner cavity 241. Valve element 240 can be positioned between a proximal portion 244 of inner cavity 241 and a distal portion 245 of inner cavity 241, such that proximal portion 244 and distal portion 245 can be substantially sealed with respect to each other. Portions 244, 245 can comprise any of a variety of sizes and shapes, and are shown with an approximately circular cross-sectional shape for illustrative purposes only. In the depicted embodiment, proximal portion 244 of inner cavity 241 comprises at least a region having a cross-sectional area that is less than distal portion 245, to facilitate sealing of valve 240 against portion 244, while allowing valve 240 to flex and move distally into distal portion 241, as described further herein. In this arrangement, the valve 240 can be configured to substantially inhibit flow through the inner cavity 241 in a proximal direction, while not substantially inhibiting the passage of articles such as a dilator or needle through the cavity, as further discussed below.

Valve element 240 can be adapted to flex or move between a closed, or substantially sealed position (e.g., FIGS. 15A and 15B), and an open, or substantially unsealed position (e.g., FIG. 15C), through flexation of resilient plate 242. Valve element 240 can move between an open and closed position through passage of a fluid (or gas), a device, or through an operation by a user (for example, using an external lever or other device attached to resilient plate 242). In the closed position, a sealing surface 266 on a proximal surface of the sealing element 243 can contact or otherwise engage with a corresponding sealing surface 267 on a distal surface of at least one of the splittable sheath body and hub. The interaction of the sealing surfaces 266 and 267 can inhibit passage through the cavity 241 in the proximal direction. Notably, pressure against the valve element 240 in a proximal direction can press the sealing surfaces 266 and 267 further together. In some embodiments, this mechanism can be sufficiently resilient to withstand pressures associated with human blood vessels, so as to prevent a loss of blood through the valve.

In some embodiments, the resilient plate 242 is configured such that the sealing surface 266 of the sealing element 243 is biased or preloaded against sealing surface 267 of the splittable sheath body and/or hub such that valve 240 is preloaded in the closed position. This biasing can enhance the above-described inhibition of passage in the proximal direction. Additionally, the biasing can help the valve element 240 inhibit passage such as the flow of fluid or gas (e.g., blood flash, or air) or passage of a device in a distal direction (e.g., longitudinally) within cavity 241. For example, the bias towards the closed position can be strong enough to resist a force (or cracking pressure) in the distal direction to open the valve element 240. In some embodiments, the preload or bias of valve element 240 can be sufficient to prevent gas from being drawn distally through cavity 241, and into a patient due to, for example, negative pressure created by a human during a normal pulse. Notably, drawing gas into a blood vessel can cause serious health effects such as an embolism.

In some embodiments, the amount of contact, engagement, or bias between sealing surfaces 266, 267 can affect the amount of cracking pressure or force required to allow such flow of fluid or passage of device within cavity 241. Additionally, the configuration of sheath 26B, valve 240, and sealing surfaces 266, 267, can be varied such that the amount of cracking pressure or force to allow fluid flow or the movement of a device in one direction (e.g., distally) within cavity 241 can be the same or different than the amount of cracking pressure or force to allow fluid flow or device movement in another direction (e.g., proximally). Additionally, it will be understood that "cracking pressure" as used herein can refer to both positive pressure in a first direction within cavity 241, or negative pressure, back flow or vacuum, in the opposed direction within cavity 241. For example, valve 240 can be configured with a cracking pressure that can hold valve 240 in a closed position for a vacuum greater than approximately 160 mmHg, and even as high as 180 mmHg, for example, to reduce the aforementioned likelihood of an embolism.

In the open position, sealing surfaces 266 and 267 can be separated by a gap or be angled with respect to each other, allowing fluid flow through cavity 241. In some embodiments, surfaces 266 and 267 can be separated by a gap or angle sufficient to allow passage of a needle, dilator or other device 263 through cavity 241, as best shown in FIG. 15C. As such, valve element 240 can allow inner cavity 241 to selectively receive fluid or a needle, dilator, or any other item 263 desired to pass through the cavity 241 and into a body space. It will be understood that the needles, dilators, guidewires, and other devices described herein can be used in combination with the embodiment depicted in FIG. 15C in a manner similar to the representative device 263.

Resilient plate 242 can comprise any of a variety of materials with sufficient rigidity to support sealing element 243 and substantially seal inner cavity 241, and with sufficient flexibility to allow valve element 240 to flex or move between the open and closed positions described herein. Resilient plate 242 can comprise a bio-compatible metal or plastic, or various composites or combinations thereof. Preferably, resilient plate 242 can comprise a material with reduced susceptibility to cold-setting, such that a needle, dilator, catheter, or other medical article can be extended through cavity 241, with valve element 240 in an open position, as described above, and packaged together for a period of time within the sheath 26B, without compromising the valve features (e.g., its flexibility and ability to seal cavity 241 when in a closed position). In some embodiments, resilient plate 242 can comprise, Nickel, Titanium, and/or steel (e.g., stainless steel, spring steel, etc.), or various alloys or combinations thereof. In some embodiments, resilient plate 242 comprises NiTi (Nitinol), or NiTi SE. In some embodiments, the resilient plate 242 can comprise a shape-memory alloy to facilitate its movement between an opened and closed position and to prevent cold-setting for extended periods of time such as 2 years.

Sealing element 243 can comprise any of a variety of materials that can substantially seal inner cavity 241 when in contact with or biased against sealing surface 267. In some embodiments, sealing element 243 can comprise metal, plastic, rubber, or other suitable biocompatible materials such as polyisoprene, silicone, polyurethane, or other elastic polymers. In some embodiments, the Shore A hardness of sealing element 243 can be within a range of approximately 5 to 90, or in some embodiments, 10 to 70, or in some embodiments, approximately 15 to 50, or in some embodiments, approximately 30. In some embodiments, the sealing element 243 can be coated or include other surface treatments, such as a siliconized surface to facilitate low-friction sliding of various elements along its surface (such as device 263). Even further, in some embodiments the resilient plate 242 and the sealing element 243 can be formed of the same material, such that the valve element 240 can optionally be a single unitary piece.

Resilient plate 242 and/or element 243 can be formed in a number of different ways, such as molding (e.g., injection), stamping and the like, and can be formed separately or integrally. Resilient plate 242 and sealing element 243 can be attached to each other in a variety of ways, such as with adhesive, bonding (e.g., ultrasonic, thermal, etc.), fasteners, overmolding, and the like. A primer or non-stick coating or surface treatment can be applied to plate 242 and/or sealing element 243 to facilitate their attachment to each other during the manufacturing thereof. In some embodiments, a plurality of plates 242 and/or elements 243 can be formed in a single molding or stamping step, with severable tabs to allow the plates 242 and/or elements 243 to be used individually. With respect to the bending properties of the resilient plate 242, described above, in some embodiments the resilient plate 242 can be pretreated to have certain mechanical characteristics prior to its combination with the sealing element 243.

The valve element 240, as depicted by way of the resilient plate 242, can attach to the sheath 26B by a variety of means. In some embodiments it can be glued or bonded to the sheath 26B. In other embodiments, the resilient plate 242 can attach to the sheath 26B by molding or overmolding. In further embodiments, the resilient plate 242 can be molded integrally with the sheath 26B (or a portion thereof such as the sheath hub half). When formed integrally, it may be desirable to give the hub 42B or body 40B a substantially greater thickness than the resilient plate 242, such that the hub or body maintains a higher rigidity. In other embodiments the resilient plate 242 can attach to the sheath 26B by a mechanical compression, such as where the sheath hub 42B or body 40B includes a groove that receives the plate, and allows it to be press-fit into position.

Figure 16A:
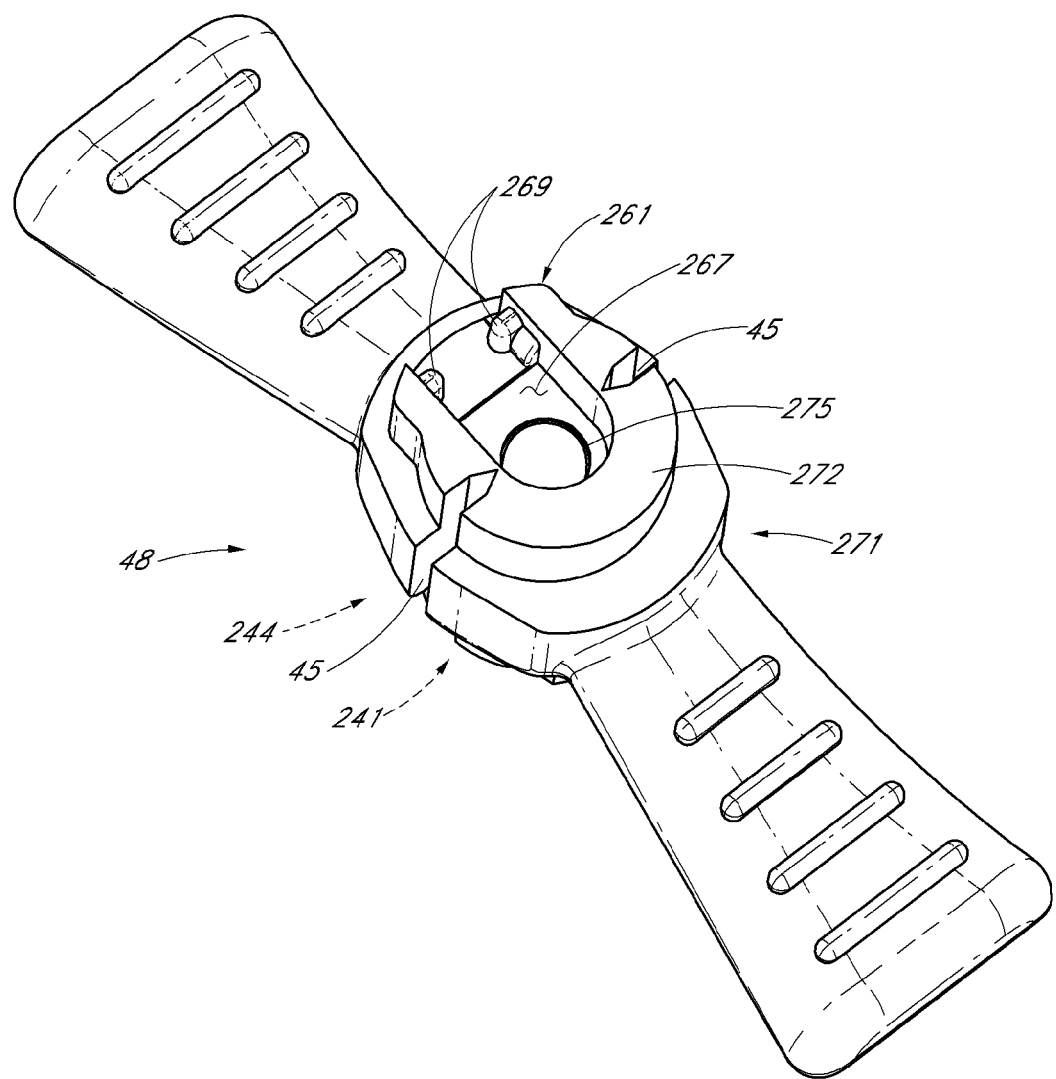
FIG. 16A is a lower isometric view of a proximal portion of the sheath hub shown in FIGS. 14A-14B.
Figure 16B:
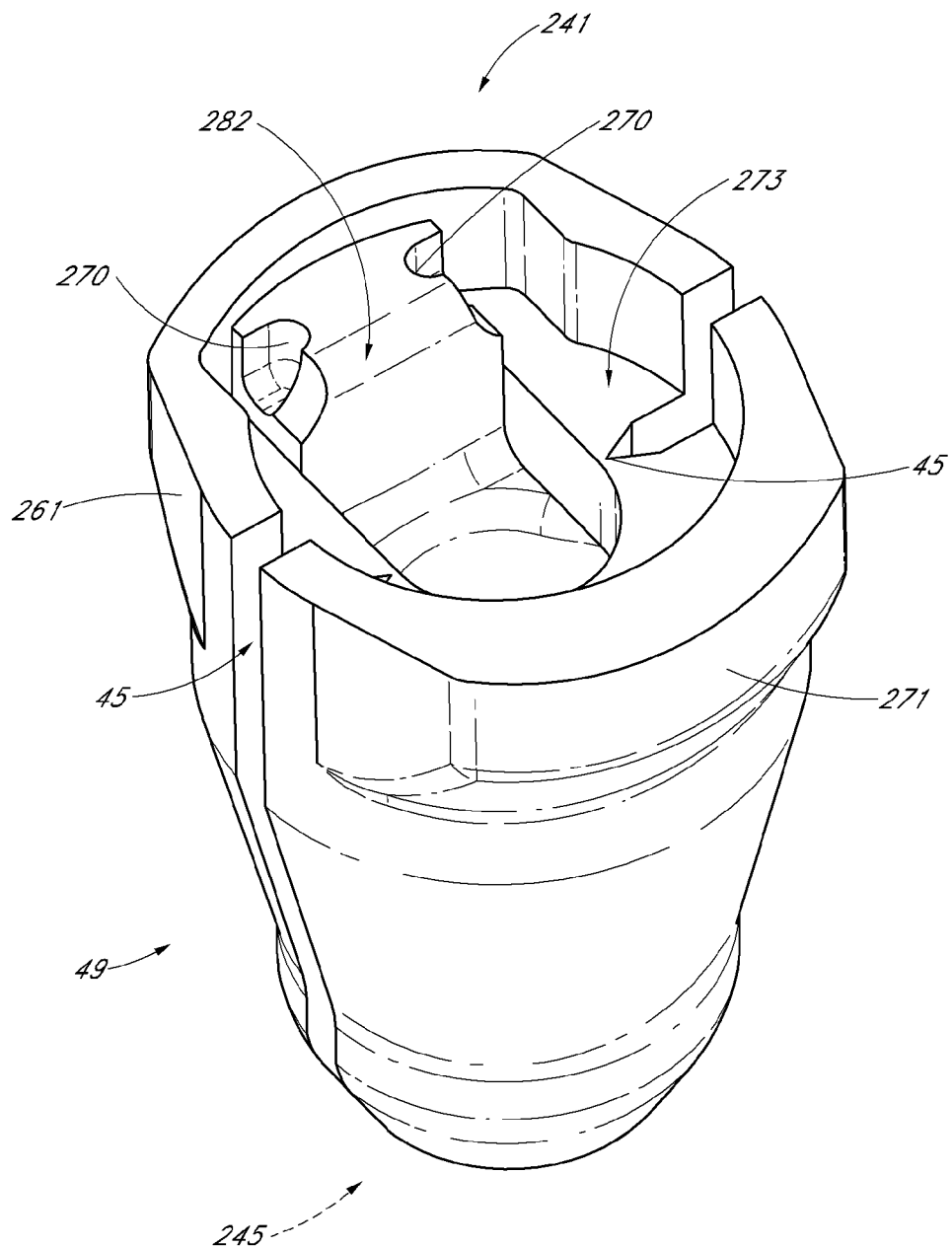
FIG. 16B is an upper isometric view of a distal portion of the sheath hub shown in FIGS. 14A-14B.

Resilient plate 242 can be attached to various portions of sheath hub 42B and/or body 40B. In some embodiments, the sheath hub 42B and/or body 40B can comprise two or more separate pieces that are positioned and attached with respect to each other such that a portion of resilient plate 242 is clamped between a portion of sheath hub 42B and/or body 40B. As best shown in FIGS. 14B, 16A and 16B, sheath hub 42B can comprise a proximal portion 48 and a distal portion 49, configured to engage with each other such that the valve element 240, by way of a mounting portion 265 of the resilient plate 242, can be supported or clamped therebetween within a groove or gap 274 (FIG. 15C). As shown in FIGS. 15A through 15C, the mounting portion 265 of the resilient plate 242, in some embodiments, can be supported within a hub wall 283 of the sheath hub 42B between an inner surface 284 of the hub wall 283 and an outer surface 285 of the hub wall 283. Portions 48, 49 can comprise any of the materials described herein generally for sheath 26B and other components thereof, such as sheath hub 42B and sheath body 40B. In one embodiment, portion 48 comprises ABS plastic. In one embodiment, portion 49 comprises a K resin. Portions 48, 49 can engage with each other using any of a variety of attachment means and methods known or described herein, such as bonding, adhesive (e.g., solvents), and the like. For illustrative purposes, portion 48 comprises a longitudinally-extending flange or protrusion 272 (FIG. 16A) configured to be received by a corresponding recession or shoulder 273 in portion 49 (FIG. 16B). Portions 48, 49 can be configured with an optional gap 280 (FIG. 15C) to allow portions 48, 49 to move longitudinally towards each other and to ensure clamping of resilient plate 242 within gap 274.

The valve element 240, and resilient plate 242, can be attached to one or more sections of sheath hub 42B and/or body 40B that separate along line(s) 45. Preferably, resilient plate 242 is attached to only one separable section of sheath 26B, such as sheath hub section 261, to facilitate the separation of valve 240 from sheath hub section 271 during the splitting of sheath 26B. Additionally, plate 242 can be attached to only one separable section of sheath 26B to facilitate the flexing and movement of resilient plate 242 and sealing element 243 within inner cavity 241. In other embodiments, where the valve element 240 is attached to multiple separable portions of the sheath hub 42B and/or body 40B, the valve element 240 can also be separable by similar structures.

FIGS. 17A-22 show various views of an embodiment of valve element 240. Although resilient plate 242 is depicted as being an approximately rectangular strip, it can comprise any of a variety of regular or irregular shapes to support sealing element 243 and substantially seal inner cavity 241, while providing sufficient flexibility to allow valve element 240 to flex or move between the open and closed positions described herein. One or more portions (e.g., mounting portion 265) of resilient plate 242 can be shaped to conform to and/or attach to a portion of sheath hub 42A and/or body 40A. One or more portions (e.g., the sealing portion 264) of resilient plate 242 can be shaped to conform to and/or attach to a portion of sealing element 243.

Valve element 240 can be configured in a number of different ways that can affect its sealing and/or engagement with other portions of sheath 26B. For example, one or more surfaces of resilient plate 242 can be approximately planar or non-planar, and/or can comprise approximately planar or non-planar portions, depending on the desired sealing and mounting configuration. In some embodiments, the resilient plate 242 can comprise an approximately continuous, planar, surface as shown in FIGS. 17A-22. In some embodiments, mounting portion 265 and the sealing portion 264 of resilient plate 242 can be bent, curved, or otherwise configured at an orthogonal or substantially non-orthogonal angle with respect to each other, and/or with respect to a portion of sheath 26B (e.g., a longitudinal axis extending through cavity 241). In some embodiments, portions of resilient plate 242 can comprise an approximately planar surface when not subjected to external forces, and can be angled, bent, or curved when preloaded or biased (e.g., when valve element 240 is in the closed position), or vice versa.

Referring to FIG. 15B, mounting portion 265 can engage with a portion of sheath 26B (e.g., between sheath hub portions 48 and 49) at an angle θ1 with respect to a plane that extends approximately orthogonally through a longitudinal axis 301 of sheath 26B and cavity 241 (e.g, such that mounting portion 265 extends proximally with respect to sheath 26B). Angle θ1 can be provided, for example, such that sealing element 243 is biased toward the corresponding sealing surface on the sheath 26B (e.g., the sealing surface 267, shown in FIGS. 15C and 16A. In a preferred embodiment, angle θ1 comprises a range of approximately 1-20 degrees, or more preferably, 3-15 degrees, or even more preferably, 5-10 degrees. In an embodiment, angle θ1 comprises approximately 8 degrees. It will be understood that although angle θ1 is defined with respect to mounting portion 265 and an orthogonal plane, a similar, or in some embodiments, increased, range of angles may be implemented that are defined with respect to mounting portion 265 and sealing portion 264, as described further below.

In some embodiments, resilient plate 242 can include an attachment element 268 (e.g., on mounting portion 265) configured to attach or engage resilient plate 242 to a corresponding attachment element on sheath hub 42A and/or body 40A, such as an attachment element 269 on proximal portion 48 (FIG. 16A) and/or similar attachment elements on distal portion 49. In the depicted embodiment, the distal portion 49 can include an attachment element 270 similar to the resilient plate's attachment element 268, to also attach to the proximal portion's attachment element 269. Attachment elements 268-270 can comprise any of a variety of shapes, such as a dimple, groove, tab, protrusion, recession, anchor and the like extending from, on, through, or into a portion of resilient plate 242 and sheath 26B. In some embodiments, one or more of the paired attachment elements 268-270 can comprise a first attachment element that is a different size and/or shape relative to a second, opposed attachment element, so that resilient plate 242 can only be installed one way, or in a single orientation, within sheath hub 42A and/or body 40A. In the illustrated embodiment, attachment element 268 comprises a notch extending into resilient plate 242, configured to engage with a corresponding protrusion 269 on sheath hub section 261. Attachment elements 268 and 269 can prevent or restrict movement of the resilient plate 242 with respect to sheath 26B in one or more directions. In a preferred embodiment, attachment elements 268, 269 can restrict both or at least one of radial and rotational movement of plate 242 with respect to sheath hub 26B about the longitudinal axis extending through sheath 26B. Attachment element 270 can be shaped similar to attachment element 268, such that element 270 on sheath hub portion 49 can engage with element 269 on sheath hub portion 48, to similarly restrict movement of sheath hub portions 48, 49 with respect to each other. Attachment elements 268-270 can also provide alignment between portions 48, 49 of sheath hub 42B, and/or between valve 240 and portions of sheath 26B. For example, elements 268-270 can improve the alignment between a raised portion of the sealing element (described further below) and portions of cavity 241. Additional embodiments of anchors that can be employed to attach valve 240 to a portion of sheath 26B are shown and described, for example, in FIGS. 25D-25F, and the corresponding supporting text (e.g., paragraphs [0214]-[0243]), of PCT International Patent Application No. PCT/US2010/034609, filed May 12, 2010, and previously incorporated by reference in its entirety herein.

Sealing element 243 can comprise any of a variety of shapes that can form a sealing surface 266 that can substantially seal inner cavity 241 when in contact with or biased against sealing surface 267. For example, sealing element 243 can comprise an approximately round, square, rectangular, ovular, or any other regular or irregular shape that can optionally substantially match a shape of the inner cavity 241. In the illustrated embodiment, sealing element 243 comprises an approximately round or circular shape.

Sealing element 243 can attach to resilient plate 242 using any methods known or described herein for attaching resilient plate 242 to sheath 26B. In an embodiment, sealing element 243 is attached to resilient plate 242 such that a portion of element 243 covers, surrounds or encloses a substantial portion of one or more sides, or in some embodiments, two or more sides of resilient plate 242. In some embodiments, element 243 covers a portion of a top and bottom and/or sides of the sealing portion 264 of plate 242. In some embodiments, element 243 covers both the top and bottom surface of resilient plate 242 such that plate 242 is "sandwiched" or positioned between two portions of sealing element 243 (see, e.g., FIGS. 15B, 20, 21). Such embodiments can reduce the wear on sheath 26B caused, for example, by the movement described herein of resilient plate 242, which is generally more rigid than sealing element 243. In some embodiments, sealing element 243 can be attached to resilient plate 242 through an overmolding process. Resilient plate 242 can include one or more apertures 276 extending therethrough (e.g., through sealing portion 264; FIG. 15C), to provide additional strength in an overmolding attachment between the resilient plate 242 and the sealing element 243. In some embodiments, sealing element 243 can include one or more alignment elements (e.g., apertures 277; FIGS. 17A-19) that can be configured to facilitate the alignment or attachment of sealing element 243 to resilient plate 242.

Referring, for example, to FIGS. 16A, 17A-17B and 19-22, sealing surfaces 266, 267 can comprise any of a variety of shapes, and are shown with an approximately circular cross-sectional shape (in the longitudinal direction) for illustrative purposes only. In the illustrative embodiment, sealing surface 267 is positioned on a shoulder or flange 279 extending inwardly (e.g., radially) from a side of inner cavity 241 (FIG. 15B). Sealing surfaces 266, 267 can extend around some, most, or substantially the entirety of the perimeter of the inner cavity 241. Surfaces 266, 267 can include substantially planar or non-planar portions, and can be a substantially regular or irregular shape.

Surface 266 and/or 267 can include one or more protrusions, recessions, or other structural elements configured to interlock and/or provide other sealing function therebetween. Referring to FIGS. 15B, 15C and 16A, sealing surface 267 can include an optional rib, ring or lip 275 extending partially or substantially completely around cavity 241. As such, rib 275 can extend longitudinally and/or radially with respect to cavity 241. Rib 275 can extend along a portion of flange 279 (FIG. 15B) or another portion of a side of cavity 241. Rib 275 can comprise the same or different material than the remainder of sealing surface 267; for example rib 275 can comprise a material with decreased hardness, increased flexibility, tackiness, or other sealing properties than the remainder of surface 267. Rib 275 can reduce the cross-sectional area of contact between surfaces 266 and 267, and thus provide increased sealing pressure for a given pressure within cavity 241 and/or bias provided by valve 240. In some embodiments, rib 275 comprises a tapered or pointed cross-sectional shape to further improve such increased sealing pressure. Rib 275 can be configured to provide the primary sealing contact between valve 240 and the sheath body 20B or hub 20A, or rib 275 can be used to provide additional sealing contact in combination with the remainder of sealing surfaces 266, 267.

The surfaces 266, 267 and/or their associated rib 275 can extend around cavity 241 approximately orthogonally with respect to the longitudinal axis 301 extending through cavity 241, or, referring to FIG. 15B, at an angle θ2 with respect to an orthogonal plane extending through the longitudinal axis 301 of cavity 241. As such, sealing portion 264 of resilient plate 242 can extend distally within cavity 241 at an angle θ2+θ1 with respect to mounting portion 265 (e.g., the angle at its pivot point about fold line 279; FIG. 15C). Positioning surfaces 266, 267 at angle θ2 can provide a more uniform seal along the entire length of sealing portion 264, including the portions of sealing portion 264 that are a greater distance from fold line 279 and mounting portion 265.

Positioning surfaces 266, 267 at an angle θ2 can also facilitate the movement of valve 240 from a closed to an open position when device 263 is inserted into or extended through cavity 241 (FIGS. 15B-C). Angling the raised portion or dome 278 to extend slightly downwardly, or distally, within cavity 241 at angle θ2 will increase the tendency of device 263 to slide towards the end of raised portion 278 away from mounting portion 265 and fold line 279, when the device 263 is extended through cavity 241. This will prevent device 263 from binding or jamming between raised portion 278 and mounting portion 265.

Positioning surfaces 266, 267 at an angle can also increase the preload between the valve element 240 and sealing surface 267, separately, or in combination with the aforementioned preload that can be provided through angle θ1. In a preferred embodiment, angle θ2 comprises a range of approximately 1-15 degrees, or more preferably, 1-10 degrees, or even more preferably, 1-5 degrees. In an embodiment, angle θ2 comprises approximately 2 degrees.

It will be understood that in some embodiments, portions of the valve element 240 can be formed or pre-bent at an angle similar to those ranges described herein for angles θ1, θ2, or θ1+θ2 prior to the valve element 240 being installed within sheath hub portions 48 and 49. For example, sealing portion 264 can be formed or pre-bent at an angle in a first direction relative to mounting portion 265, and bent in the opposite direction to preload valve element 240 when installed within sheath hub 48 and 49. Such preloading can provide bias and improved sealing between valve element 240 and the corresponding sealing surface on sheath 26B, similar to, and as an addition or alternative to, those other embodiments described above. In a preferred embodiment, sealing portion 264 and mounting portion 265 are pre-bent at an angle less than 180 degrees with respect to each other, such that, when installed within sheath hub portions 48 and 49, resilient plate 242 is substantially flat and at an angle of approximately 180 degrees, while still being preloaded and providing improved sealing and an increased cracking pressure as described further herein.

In some embodiments, sealing element 243 can include a raised portion, such as substantially dome-shaped portion 278, configured to extend a height H with respect to surface 266 (FIG. 21; e.g. approximately longitudinally and/or proximally with respect to sheath body 40B within cavity 241; see also FIG. 15B). Sealing surface 266 can at least partially surround some, most, or substantially the entirety of the perimeter of raised portion 278. In some embodiments, the raised portion 278 can engage (e.g., through an interference fit) with an inner wall of cavity 241, to provide additional sealing of cavity 241. In some embodiments, the raised portion can be shaped and sized to prevent interference with the inner wall of cavity 241, to prevent restriction of the movement of valve element 240 between an open and closed position, except as otherwise described herein. The raised portion 278 can extend a height H that is sufficient to prevent or reduce the likelihood of contact between the sealing surface 266 and a device 263, when the device 263 is extended through cavity 241 (FIG. 15C). Additionally, during the aforementioned period of time when the sheath 26B is stored with a device 263 extended through the cavity 241, if the device 263 sets or sticks to another portion of the sheath 26B, it will do so to the raised portion 278, and not to a portion of the sealing surface 266. As such, the raised portion 278 can prevent damage to the sealing surface 266 of the sealing element 243 by extended forceful contact with the device 263, and thus extend the sealing capability and life of the valve element 240. Raised portion 278 can comprise any of the materials described herein for sealing element 243, and/or can comprise the same or different material as the remainder of element 243. In some embodiments, raised portion 278 comprises one or more coatings to provide a moisture barrier, lubrication, or other properties, such as silicone or chemical vapor deposited poly(p-xylylene) polymers such as Parylene™.

As described above, bending of the resilient plate 242 can be encouraged in a number of ways. For example, in some embodiments, the material properties of the resilient plate 242 can facilitate bending. In other embodiments, the resilient plate 242 can have a fold line 279 along which it can bend (see, e.g., FIGS. 15C and 17A). It may be preferable for this fold line to correspond to a portion of resilient plate 242 proximate to the inner wall of cavity 241, and/or the portion of the sheath hub 42B and/or sheath body 40B to which the valve 240 is attached. In some embodiments, the fold line 279 can extend across resilient plate 242 at the transition between sealing portion 264 and mounting portion 265. Fold line 279 can facilitate bending through regions of thinner/weaker material that allow the resilient plate 242 to bend (but not break). For example, in some embodiments the resilient plate 242 can be substantially rigid in all except a designated folding region that is resiliently flexible. The fold line or folding region can be formed from perforations, grooves, or some other structure. In some embodiments, an additional shape-memory structure can define a bending area or region. The ease or difficulty with which resilient plate 242 can be bent (e.g., along fold line 279) can affect the cracking pressure of valve 240. For example, one or more optional apertures 281 (e.g., FIGS. 17A-B) can be extended through resilient plate 242 proximate to fold line 279, to decrease the cracking pressure of valve 240. In some embodiments, a portion of sheath 26B can be radiused, tapered, or chamfered relief to facilitate a smooth bend of resilient plate 242 along fold line 279. For example, referring to FIG. 15B, sheath hub 42B (e.g., portion 49) can include a radiused or tapered relief 282 proximate to the point of attachment of resilient plate 242 to sheath 26B.

In use, an operator can insert a medical article 263 through the sheath hub, such as a needle, dilator, catheter, or the like. The article can enter the cavity 241 from a proximal end (e.g., from cavity portion 244), until it contacts dome 278. It can then press against dome 278 (e.g., without substantially contacting surface 266), and move valve 240 from a closed to an open position. The article can then continue to move longitudinally within cavity 241 (e.g., into cavity portion 245), while valve 240 is in an open position, and still without substantially contacting surface 266. The above steps can be reversed to remove article 263 from cavity 241, with valve 240 returning to a closed position, and without contacting surface 266 with the article. Other articles can be inserted and removed in a similar manner.

When the sheath is splittable, it can beneficially be split with the medical article inside, without disturbing the medical article. Advantageously, when an operator actuates the tabs 43 to split the sheath, the sheath can break such that it sheath splits into two or more sections (e.g., sheath hub sections 261, 271), and the valve 240 remains with one of the two or more sections (e.g., section 261). Accordingly, the sheath and the corresponding seal can be split without disturbing a medical article inside. It will be clear from the disclosure herein that a similar procedure can be performed with other embodiments of the sheath.

The embodiments herein described are comprised of conventional, biocompatible materials. For example, the needle preferably consists of ceramic, a rigid polymer, or a metal such as stainless steel, nitinol, or the like. The other elements can be formed of suitable polymeric materials, such as polycarbonate, nylon, polyethylene, high-density polyethylene, polypropylene, fluoropolymers and copolymers such as perfluoro (ethylene-propylene) copolymer, polyurethane polymers or co-polymers. For example, in some embodiments the dilator can be formed from nylon.

As noted above, the present access device can be used to place a catheter at other locations within a patient's body. Thus, for example, but without limitation, the access device can be used as or with a variety of catheters to drain fluids from abscesses, to drain air from a pneumotorax, and to access the peritoneal cavity. In such applications, body fluids flow into the viewing space to indicate when the needle has been properly placed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. For example, the general shape of the needle hub depicted in FIG. 8F differs in additional ways from the needle hub depicted in FIG. 2F. However, these general needle hub shapes can be interchanged between the described and depicted embodiments. Additionally, it will also be understood that although many of the embodiments herein describe the use of an access device that includes a needle, dilator, sheath, guidewire section, track, cover, and other components, the invention can include one or more of these or other components described herein, supplied separately, or in combination. For example, the components described herein can be supplied in an assembled form, or can be supplied as a kit or other packaged configuration that is supplied separately and then assembled by the user. Additionally, the invention can include an instruction for using any of the embodiments described herein, wherein the instruction is provided in a tangible medium, such as paper, audio and/or visual recording, computer or other electronic memory, and the like.

Thus, it is intended that the scope of the present invention herein disclosed should not be limited by the particular disclosed embodiments described above, but should be determined only by a fair reading of the disclosure and the claims that follow.

What is claimed is:

1. A medical article comprising: a sheath comprising:
a splittable sheath hub comprising a cylindrical, longitudinally extending hub wall, the longitudinally extending hub wall having an inner surface and an outer surface, the longitudinally extending hub wall defining a longitudinal axis and forming an inner cavity through which the longitudinal axis extends; and a valve element comprising:
a resilient plate comprising a mounting portion and a sealing portion,
the mounting portion being supported within the longitudinally extending hub wall on an oblique surface formed between the inner surface and the outer surface at a first oblique angle relative to the longitudinal axis and extending inwardly from the inner surface of the longitudinally extending hub wall, and
the sealing portion extending into the inner cavity; and a sealing element comprising a first sealing surface and being supported by the resilient plate,
wherein the first oblique angle biases the sealing element toward a position against a second sealing surface on the splittable sheath hub to substantially seal at least a portion of the inner cavity.

2. The medical article of claim 1, wherein at least one of the first and second sealing surfaces extends around the substantial entirety of an inner perimeter of the inner cavity.

3. The medical article of claim 1, further comprising a flange extending inwardly from a side of the inner cavity, the flange forming at least a portion of the second sealing surface.

4. The medical article of claim 3, further comprising a rib extending longitudinally within the inner cavity from the flange, wherein the second sealing surface comprises at least a portion of the rib.

5. The medical article of claim 1, wherein the resilient plate comprises a flexible material with properties inhibiting cold-setting when held in a flexed position for extended periods of time.

6. The medical article of claim 5, wherein the resilient plate comprises Nitinol.

7. The medical article of claim 1, further comprising a splittable sheath body having a proximal end, a distal end, and a tubular structure extending therebetween, the sheath body defining a longitudinal axis and being splittable into two portions along two pre-determined split lines generally parallel to the longitudinal axis, wherein the splittable sheath hub extends from the proximal end of the splittable sheath body and the inner cavity extends along the longitudinal axis of the sheath body.

8. The medical article of claim 7, wherein the sealing element further comprises a raised portion with respect to the first sealing surface, wherein the raised portion projects away from the sheath body.

9. The medical article of claim 8, wherein the raised portion has a height sufficient to inhibit contact between the first sealing surface and a device extended through the cavity.

10. The medical article of claim 8, wherein the first sealing surface forms a perimeter surrounding the raised portion.

11. The medical article of claim 8, wherein the raised portion comprises a substantially dome-like shape.

12. The medical article of claim 7, wherein the tubular structure is generally flexible.

13. The medical article of claim 7, wherein the sheath hub is splittable into two sheath hub portions along the two pre-determined split lines, wherein the mounting portion of the resilient plate is supported by a first of the two portions such that the valve element is separable from and movable with respect to a second of the two sheath hub portions.

14. The medical article of claim 13, wherein the sheath hub comprises a distal portion and a proximal portion coupled together with the mounting portion of the resilient plate supported between the distal portion and the proximal portion of the sheath hub.

15. The medical article of claim 14, wherein the sheath hub and the resilient plate comprise a pair of corresponding attachment elements configured to restrict at least one of radial and rotational movement of the resilient plate relative to the longitudinal axis.

16. The medical article of claim 13, wherein the resilient plate has a weakened portion at which the resilient plate can bend such that the sealing portion moves with respect to the mounting portion.

17. The medical article of claim 16, wherein the resilient plate is bent at the weakened portion to be substantially non-planar to preload the first sealing surface against the second sealing surface.

18. The medical article of claim 14, wherein the mounting portion is supported between the distal portion and proximal portion of the sheath hub at the first oblique angle with respect to the longitudinal axis, wherein the distal portion and the proximal portion of the sheath hub each comprise a circular cross-sectional shape such that the longitudinally extending hub wall has an annular shape, and wherein the second sealing surface extends around the inner cavity at a second oblique angle with respect to the longitudinal axis.

19. The medical article of claim 13, wherein at least a portion of the second sealing surface is formed on the second of the two sheath hub portions.

20. The medical article of claim 13, wherein the two pre-determined split lines are parallel to the longitudinal axis of the sheath hub.

21. An access device, comprising:
a needle; a dilator; and a splittable sheath comprising:
a splittable sheath body;
a splittable sheath hub extending from a proximal end of the sheath body, the splittable sheath hub comprising a longitudinally extending hub wall having an inner surface and an outer surface, wherein the sheath body and sheath hub forming an inner cavity along a longitudinal axis defined by the sheath body and sheath hub; and a valve element comprising:
a resilient plate comprising a mounting portion and a sealing portion,
the mounting portion being supported within the longitudinally extending hub wall on an oblique surface formed between the inner surface and the outer surface at a first oblique angle relative to the longitudinal axis and extending inwardly from the inner surface of the longitudinally extending hub wall, and
the sealing portion extending into the inner cavity; and a sealing element comprising a first sealing surface and being supported by the resilient plate;
wherein the first oblique angle biases the sealing element toward a first position against a second sealing surface on at least one of the splittable sheath body and the splittable sheath hub to substantially seal the inner cavity, and wherein the sealing element is movable from the first position to a second position when at least one of the needle and dilator is extended through the cavity, without substantial contact between the at least one of the needle and dilator and the first sealing surface.

22. The access device of claim 21, wherein the sheath hub comprises a distal portion and a proximal portion coupled together with the mounting portion of the resilient plate supported between the distal portion and the proximal portion of the sheath hub.

23. The access device of claim 22, wherein the mounting portion is supported between the distal portion and the proximal portion of the sheath hub at the first oblique angle with respect to the longitudinal axis, wherein the distal portion and the proximal portion of the sheath hub each comprise a circular cross-sectional shape such that the longitudinally extending hub wall has an annular shape, and wherein the second sealing surface extends around the inner cavity at a second oblique angle with respect to the longitudinal axis.

24. The access device of claim 21, wherein the resilient plate comprises a flexible material with properties inhibiting cold-setting when held in a flexed position for extended periods of time.

25. The access device of claim 21, wherein the sealing element further comprises a raised portion with respect to the first sealing surface, wherein the raised portion projects away from the sheath body.

26. The access device of claim 25, wherein the raised portion comprises a substantially dome-like shape.

27. The access device of claim 21, wherein the resilient plate has a weakened portion at which the resilient plate can bend such that the sealing portion moves with respect to the mounting portion.

28. The access device of claim 21, wherein the sheath body is splittable into two portions along two pre-determined split lines generally parallel to the longitudinal axis.

* * * * *